(12) United States Patent
Gustafsson et al.

(10) Patent No.: US 11,395,808 B2
(45) Date of Patent: Jul. 26, 2022

(54) DELAYED RELEASE PHARMACEUTICAL FORMULATIONS COMPRISING VALPROIC ACID, AND USES THEREOF

(71) Applicant: Cereno Scientific AB, Gothenburg (SE)

(72) Inventors: Nils Ove Gustafsson, Loddekopinge (SE); Hans Roger Marcus Martensson, Malmo (SE); Niklas Bergh, Askim (SE); Jonas Faijerson Saijo, Gothenburg (SE); Sverker Jern, Ljungskile (SE)

(73) Assignee: Cereno Scientific AB, Gothenburg (SE)

( * ) Notice: Subject to any disclaimer, the term of this patent is extended or adjusted under 35 U.S.C. 154(b) by 0 days.

(21) Appl. No.: 16/090,664

(22) PCT Filed: Apr. 10, 2017

(86) PCT No.: PCT/GB2017/051002
§ 371 (c)(1),
(2) Date: Oct. 2, 2018

(87) PCT Pub. No.: WO2017/175013
PCT Pub. Date: Oct. 12, 2017

(65) Prior Publication Data
US 2019/0111011 A1    Apr. 18, 2019

(30) Foreign Application Priority Data
Apr. 8, 2016   (GB) .................................. 1606197

(51) Int. Cl.
| A61K 31/19 | (2006.01) |
| A61K 9/28 | (2006.01) |
| A61K 9/48 | (2006.01) |
| A61K 31/20 | (2006.01) |
| A61K 9/20 | (2006.01) |
| A61P 7/02 | (2006.01) |
| A61P 9/10 | (2006.01) |

(52) U.S. Cl.
CPC ............ *A61K 31/19* (2013.01); *A61K 9/2013* (2013.01); *A61K 9/284* (2013.01); *A61K 9/2846* (2013.01); *A61K 9/2886* (2013.01); *A61K 9/4891* (2013.01); *A61K 31/20* (2013.01); *A61P 7/02* (2018.01); *A61P 9/10* (2018.01)

(58) Field of Classification Search
None
See application file for complete search history.

(56) References Cited

U.S. PATENT DOCUMENTS

| 5,049,586 | A | 9/1991 | Ortega et al. | |
| 2004/0043026 | A1 | 3/2004 | Tuan et al. | |
| 2004/0170684 | A1* | 9/2004 | Baichwal | A61K 9/167 |
| | | | | 424/468 |
| 2004/0224006 | A1 | 11/2004 | Raffaniello | |
| 2005/0276848 | A1 | 12/2005 | Podhipleux et al. | |
| 2005/0276850 | A1* | 12/2005 | Podhipleux | A61K 9/2072 |
| | | | | 424/468 |
| 2006/0178437 | A1 | 8/2006 | Mishra et al. | |
| 2009/0048156 | A1 | 2/2009 | Brodie et al. | |
| 2009/0048300 | A1 | 2/2009 | Chen et al. | |
| 2009/0088410 | A1 | 4/2009 | Zeldis | |
| 2009/0270497 | A1 | 10/2009 | Buggy | |
| 2013/0022676 | A1* | 1/2013 | Mullen | A61K 9/282 |
| | | | | 424/465 |
| 2014/0051716 | A1 | 2/2014 | Larsson et al. | |
| 2017/0020874 | A1 | 1/2017 | Larsson et al. | |
| 2018/0177751 | A1* | 6/2018 | Jern | A61K 31/19 |
| 2019/0111011 | A1 | 4/2019 | Gustafsson et al. | |
| 2020/0179381 | A1 | 6/2020 | Bergh et al. | |

FOREIGN PATENT DOCUMENTS

| CN | 101947209 B | 7/2012 | |
| DE | WO 2001039747 A2 * | 6/2001 | .......... A61K 9/2013 |
| EP | 1743654 | 1/2007 | |
| EP | 1815850 B1 * | 11/2008 | .......... A61K 9/2054 |
| IN | 236664 B | 11/2009 | |
| WO | 2002/055017 | 7/2002 | |
| WO | 2003/013493 | 2/2003 | |
| WO | 2005/105066 | 11/2005 | |
| WO | 2006/1177165 | 11/2006 | |
| WO | 2007/030697 | 3/2007 | |
| WO | 2007/084775 | 7/2007 | |
| WO | 2007/115287 | 10/2007 | |
| WO | 2008027993 A2 | 3/2008 | |
| WO | 2011/113013 | 9/2011 | |
| WO | 2011107749 A2 | 9/2011 | |
| WO | 2012/120262 | 9/2012 | |
| WO | 2016/055797 | 4/2016 | |

OTHER PUBLICATIONS

FDA (https://www.accessdata.fda.gov/drugsatfda_docs/label/2011/018081s046_18082s031lbl.pdf, 2011). (Year: 2011).* Angleton et al. "Diurnal variation of tissue-type plasminogen activator and its rapid inhibitor (PAI-1)" Circulation, 79(1):101-106 (1989).
Cho et al. "Valproic Acid Induces Astrocyte-Dependent Neurite Outgrowth from Cultured Rat Primary Cortical Neuron Via Modulation of tPA/PAI-1 Activity", Feb. 4, 2013, Wiley Online Library, 694-709.
Christiansen et al. "Inflammatory Cytokines as Risk Factors for a First Venous Thrombosis: A Prospective Population-Based Study" PLoS Medicine, 3(8):1414-1419 (2006).
Collen et al. "Tissue-type plasminogen activator: a historical perspective and personal account" Journal of Thrombosis and Haemostasis, (2004) pp. 541-546.

(Continued)

*Primary Examiner* — Celeste A Roney
(74) *Attorney, Agent, or Firm* — Myers Bigel, P.A.

(57) ABSTRACT

There is provided herein a pharmaceutical formulation having one or more component comprising valproic acid (VPA) and/or a pharmaceutically acceptable salt thereof; and one or more secondary acid, and optionally comprising one or more pharmaceutically acceptable excipient. There is also provided uses of such formulations.

18 Claims, 7 Drawing Sheets

(56) References Cited

OTHER PUBLICATIONS

Cugno et al. "Antibodies to tissue-type plasminogen activator in plasma from patients with primary antiphospholipid syndrome" British Journal of Haematology, 108:871-875 (2000).
Falanga et al. "Deep vein thrombosis in cancer: the scale of the problem and approaches to management" Annals of Oncology, 16:696-701, 2005.
Final Office Action corresponding to U.S. Appl. No. 14/955,922, dated Feb. 2, 2018, 13 pages.
Final Office Action Corresponding to U.S. Appl. No. 14/003,780; dated Jul. 1, 2015; 16 pages.
Galli et al. "A phase II multiple dose clinical trial of histone deacetylase inhibitor ITF2357 in patients with relapsed or progressive multiple myeloma" Ann. Hematol (2010), 89:185-190.
Goldenberg et al. "Markers of Coagulation and Angiogenesis in Cancer-Associated Venous Thromboembolism", Journal of Clinical Oncology. vol. 21. No. 22, Nov. 15, 2003, pp. 4194-4199.
http://medical-dictionary.thefreedictionary.com/prevention accessed on Nov. 21, 2014.
International Search Report and Written Opinion corresponding to International Application No. PCT/GB2012/000229, dated May 18, 2012 (11 pages).
International Search Report and Written Opinion Corresponding to International Application No. PCT/GB2015/052950 dated Apr. 19, 2016; 23 Pages.
Larsson et al. Poster Entitled, "Valproic Acid Stimulates t-PA Expression in Human Endothelial Cells," Epigenetics, 2009 Australian Scientific Conference, Melbourne, Australia, Dec. 1-4, 2009.
Leoni et al. "The Histone Deacetylase Inhibitor ITF2357 Reduces Production of Pro-Inflammatory Cytokines In Vitro and Systemic Inflammation in Vivo", Molecular Medicine, 11:1-15 (2005).
Non Final Office Action Corresponding to U.S. Appl. No. 14/003,780; dated Nov. 25, 2014, 16 pages.
Non-Final Office Action Corresponding to U.S. Appl. No. 14/955,922; dated Apr. 27, 2017; 13 pages.
Non-Final Office Action Corresponding to U.S. Appl. No. 14/955,922; dated Jan. 7, 2019; 10 pages.
Novotny-Diermayr et al. "SB939, a Novel Potent and Orally Active Histone Deacetylase Inhibitor with High Tumor Exposure and Efficacy in Mouse Models of Colorectal Cancer", Mol. Cancer Ther; 9(3):642-652, Mar. 9, 2010.
Ojemann et al., "Fibrinogen and Valproic-Acid," Epilepsia, 22(2):242-243 1981.
Rambaldi et al. "A pilot study of the Histone-Deacetylase inhibitor Givinostat in patients with JAK2V617F positive chronic myeloproliferative neoplasms" British Journal of Haematology, 150:446-455 (2010).
Ren et al. "Valproic acid reduces brain damage induced by transient focal cerebral ischemia in rats: potential roles of histone deacetylase inhibition and heat shock protein induction" Journal of Neurochemistry, 2004, 89:1358-1367.
Saluveer et al. "Profibrinolytic Effect of the Epigenetic Modifier Valproic Acid in Man" PLOS ONE, (2014), 9(10) 7 pages
Steinbrugger et al. "Analysis of inflammation- and atherosclerosis-related gene polymorphisms in branch retinal vein occlusion", Mol Vis., 15:609-618 (2009).
Sutor et al., "Influence of dipropylacetic acid (Ergenyl) on blood clotting," Medizinische Welt, vol. 25, No. 11, 1974, pp. 447-449 English translation.

Svennerholm et al., "Histone Deacetylase Inhibition Enhances Tissue Plasminogen Activator Release Capacity in Atherosclerotic Man" PLOS ONE, (Mar. 2015), vol. 10, No. 3; 13 pages.
Tabrizi et al. "Tissue Plasminogen Activator (tPA) Deficiency Exacerbates Cerebrovascular Fibrin Deposition and Brain Injury in a Murine Stroke Model: Studies in tPA-Deficient Mice and Wild-Type Mice on a Matched Genetic Background" Arterioscler Thromb Vasc Biol., 1999, 19:2801-2806.
Tsunaka et al "Cell-based laboratory evaluation of coagulation activation by antineoplastic drugs for the treatment of lymphoid tumors", SAGE Open Med., vol. 4: 1-9, 2016.
Wang et al. "Beneficial effects of mood stabilizers lithium, valproate and lamotrigine in experimental stroke models", Review. Acta Pharmacologica Sinica, (2011) 32: 1433-1445.
Wang at al. "Histone Deacetylase Inhibitors Suppress TF-kB-dependent Agonist-driven Tissue Factor Expression in Endothelial Cells and Monocytes", The Journal of Biological Chemistry, 282:28408-28418 (2007).
WebMD, "How to Prevent Deep Vein Thrombosis (DVT)", http://www.webmd.com/dvt/deep-vein-thrombosis-prevent-dvt#1 accessed on Apr. 24, 2017.
Woyach et al. "Lack of Therapeutic Effect of the Histone Deacetylase Inhibitor Varinostat in Patients with Metastatic Radioiodine-Refractory Thyroid Carcinoma" J Clin Endocrinol Metab., 94(1):164-170 2009.
Yong et al. A phase I dose escalation study of oral SB939 when administered thrice weekly (every other day) for 3 weeks m a 4-week cycle in patients with advanced solid malignancies. Eur J Cancer, 6 (2008) abstract.
Zeller et al "Influence of Valproate Monotherapy on Platelet Activation and Hematologic Values" Epilepsia 40(2):186-189 (1999).
Diaz "Inflammation and Acute Venous Thrombosis" US Oncology & Hematology, 7(1):68-71 (2011).
Guidance for Industry: Estimating the Maximum Safe Starting Dose in Initial Clinical Trials for Therapeutics in Adult Healthy Volunteers, Pharmacology and Toxicology (2005) 30 pages.
International Search Report and Written Opinion corresponding to International Application No. PCT/GB2017/051002, dated Jul. 13, 2017, 16 pages.
Bruce et al. "Properties of Enteric Coated Sodium Valproate Pellets", International Journal of Pharmaceutics, Elsevier, 264(1/02):85-96 (2003) Abstract.
Final Office Action corresponding to U.S. Appl. No. 14/955,922, dated Oct. 16, 23 pages.
International Search Report and Written Opinion corresponding to International Patent Application No. PCT/GB2017/050997, dated Sep. 22, 2017, 19 pages.
"U.S. Appl. No. 16/135,639; Office Action dated Feb. 4, 2021".
"U.S. Appl. No. 16/135,639; Office Action dated Jul. 31, 2020".
"U.S. Appl. No. 16/135,639; Office Action dated Oct. 30, 2019".
"Valproic Acid", NHS reviewed: Sep. 24, 2018. (Year: 2018).
Scheer, Frank A.J.L, et al., "Human circadian system causes a morning peak in prothrombotic plasminogen activator inhibitor-1 (PAI-1) independent of the sleep/wake cycle", Blood 123(4):590-593 (Jan. 23, 2014).
"U.S. Appl. No. 16/090,661; Office Action dated Sep. 1, 2021".
"U.S. Appl. No. 16/135,639; Office Action dated Sep. 15, 2021".
"U.S. Appl. No. 17/477,248; Office Action dated Jan. 21, 2022".
Furlan, Antonio , et al., "Pharmacokinetics, Safety and Inducible Cytokine Responses during a Phase 1 Trial of the Oral Histone Deacetylase inhibitor ITF2357 (Givinostat)", Mol Med 17(5-6):353-362 (May-Jun. 2011).

* cited by examiner

DELAYED RELEASE PHARMACEUTICAL FORMULATIONS COMPRISING VALPROIC ACID, AND USES THEREOF

STATEMENT OF PRIORITY

This application is a 35 U.S.C. § 371 national phase entry of International Application No. PCT/GB2017/051002, filed Apr. 10, 2017, which claims the benefit, under 35 U.S.C. § 119(a) of United Kingdom Application No, 1606197.0, filed Apr. 8, 2016, the entire contents of each of which are incorporated herein by reference herein.

FIELD OF THE INVENTION

The present invention generally relates to new pharmaceutical compositions and medical uses thereof. More specifically, it relates to specific pharmaceutical formulations comprising valproic acid (VPA) and/or pharmaceutically acceptable salts thereof, and their use in the treatment or prevention of thrombus formation and in improving or normalizing endogenous vascular fibrinolysis.

BACKGROUND OF THE INVENTION

The listing or discussion of an apparently prior-published document in this specification should not necessarily be taken as an acknowledgement that the document is part of the state of the art or is common general knowledge.

Cardiovascular disease is the leading cause of morbidity and mortality in the western world and during the last decades it has also become a rapidly increasing problem in developing countries. An estimated 80 million American adults (one in three) have one or more expressions of cardiovascular disease (CVD), such as hypertension, coronary heart disease, heart failure, or stroke. Mortality data show that CVD was the underlying cause of death in 35% of all deaths in 2005 in the United States, with the majority related to myocardial infarction, stroke, or complications thereof. The vast majority of patients suffering acute cardiovascular events have prior exposure to at least one major risk factor, such as cigarette smoking, abnormal blood lipid levels, hypertension, diabetes, abdominal obesity and low-grade inflammation.

Pathophysiologically, the major events of myocardial infarction and ischemic stroke are caused by a sudden arrest of nutritive blood supply due to a blood clot formation within the lumen of the arterial blood vessel. In most cases, formation of the thrombus is precipitated by rupture of a vulnerable atherosclerotic plaque, which exposes chemical agents that activate platelets and the plasma coagulation system. The activated platelets form a platelet plug that is armed by coagulation-generated fibrin to form a blood clot that expands within the vessel lumen until it obstructs or blocks blood flow, which results in hypoxic tissue damage (so-called infarction). Thus, thrombotic cardiovascular events occur as a result of two distinct processes, i.e. a slowly progressing long-term vascular atherosclerosis of the vessel wall, on the one hand, and a sudden acute clot formation that rapidly causes flow arrest, on the other. Without wishing to be bound by theory, it is thought that the present invention solely relates to the latter process.

Recently, inflammation has been recognized as an important risk factor for thrombotic events. Vascular inflammation is a characteristic feature of the atherosclerotic vessel wall, and inflammatory activity is a strong determinant of the susceptibility of the atherosclerotic plaque to rupture and initiate intravascular clotting. Also, autoimmune conditions with systemic inflammation, such as rheumatoid arthritis, systemic lupus erythematosus and different forms of vasculitides, markedly increase the risk of myocardial infarction and stroke.

Traditional approaches to prevent and treat cardiovascular events are targeted: 1) to slow down the progression of the underlying atherosclerotic process; 2) to prevent clot formation in case of a plaque rupture; or 3) to direct removal of an acute thrombotic flow obstruction. In short, antiatherosclerotic treatment aims at modulating the impact of general risk factors and includes dietary recommendations, weight loss, physical exercise, smoking cessation, cholesterol- and blood pressure treatment etc.

Prevention of clot formation mainly relies on the use of antiplatelet drugs that inhibit platelet activation and/or aggregation, but also in some cases includes thromboembolic prevention with oral anticoagulants such as warfarin. Post hoc treatment of acute atherothrombotic events requires either direct pharmacological lysis of the clot by thrombolytic agents such as recombinant tissue-type plasminogen activator or percutaneous mechanical dilation of the obstructed vessel.

Despite the fact that multiple-target anti-atherosclerotic therapy and clot prevention by antiplatelet agents have lowered the incidence of myocardial infarction and ischemic stroke, such events still remain a major population health problem. This shows that in patients with cardiovascular risk factors these prophylactic measures are insufficient to completely prevent the occurrence of atherothrombotic events.

Likewise, thrombotic conditions on the venous side of the circulation, as well as embolic complications thereof such as pulmonary embolism, still cause substantial morbidity and mortality. Venous thrombosis has a different clinical presentation and the relative importance of platelet activation versus plasma coagulation are somewhat different, with a preponderance for the latter in venous thrombosis. However, despite these differences, the major underlying mechanisms that cause thrombotic vessel occlusions are similar to those operating on the arterial circulation. Moreover, although unrelated to atherosclerosis as such, the risk of venous thrombosis is related to general cardiovascular risk factors, such as inflammation and metabolic aberrations.

Taken together, existing therapy and general risk factor management offers insufficient protection against thrombotic events, both in the arterial and venous circulations, and cannot reverse the severe consequences of such events. This creates a need for development of novel preventive and therapeutic targets, especially more effective approaches that could prevent hazardous tissue ischemia, and ideally at such an early stage that symptoms have not yet occurred.

Interestingly, it has been found that, in an otherwise healthy individual, there is a natural "last line of defense" system, which can be activated if a clotting process, despite preventive measures, should occur in the vasculature. In brief, initiation of a thrombotic mechanism both on the arterial and venous sides of the circulation leads to activation of the innermost cell layer of the blood vessel (the endothelium), and as a response the cells rapidly release large amounts of the clot-dissolving substance tissue-type plasminogen activator (t-PA). This raises luminal t-PA levels to similar levels as with clinical thrombolytic therapy (i.e. administration of recombinant t-PA), but the potency of this endogenous response is 100-fold greater due to the extremely rapid onset of action.

Accumulating clinical, epidemiologic, and experimental data support the notion that if this thromboprotective function of the blood vessel wall is intact, it offers a powerful defense against formation of flow-arresting thrombi. Unfortunately, however, the capacity for acute t-PA release is impaired in several conditions with increased susceptibility to thrombotic events. These include atherosclerosis, hypertension, abdominal obesity, smoking, sedentary lifestyle, and low-grade inflammation. This impairment is most likely due to a diminished synthesis and thereby reduced availability of the fibrinolytic activator in the endothelial cells.

In addition, we and others have shown that the efficiency of the endogenous fibrinolytic response is reduced in patients with increased risk for an atherothrombotic event, such as in atherosclerosis (Osterlund, B., et al. *Acta Anaesthesiol Scand* 52, 1375-1384 (2008), Newby, D. E., et al. *Circulation* 103, 1936-1941 (2001)). Recent data suggest that inflammation may be an underlying pathogenetic mechanism behind the suppressed t-PA production in this state. We have shown that prolonged exposure to the inflammatory cytokines tumor necrosis factor alpha (TNF-alpha) and interleukin-1 beta (IL-1b) causes a marked suppression of the transcription of t-PA (Ulfhammer, E., et al. *Journal of Thrombosis and Haemostasis* 4, 1781-1789 (2006), Larsson, P., et al. *Thromb Res* 123, 342-351 (2008)). Interestingly, it is known that the atherosclerotic plaque is associated with a local, potentially severe, inflammatory activation in the vessel wall and it is conceivable that this inflammatory milieu hampers the fibrinolytic response in the specific areas of the vasculature where it is pivotal to retain a high fibrinolytic capacity, thus increasing the risk of thrombotic events. Similarly, it is also likely that the increased incidence of thrombotic events in patients with systemic inflammatory conditions (e.g. autoimmune diseases and the metabolic syndrome), could also be related to a suppressive effect of circulating pro-inflammatory cytokines on t-PA synthesis and/or increased levels of plasminogen activator inhibitor 1 (PAI-1).

Against this background, an alternative fourth approach to reduce the incidence of clinical thrombotic events should be to restore the capacity of the fibrinolytic 'last line of defense' system in patients with an impairment of its function. Extensive efforts have been made to find a feasible means for enhancing basal as well as stimulated endogenous fibrinolysis in subjects with a risk factor-associated reduction of fibrinolytic capacity. However, previous attempts to ameliorate t-PA synthesis with e.g. statins and retinoic acid have been disappointing. Other means of increasing fibrinolysis by blocking naturally occurring inhibitors of t-PA activity such as plasminogen activator inhibitor-1 (PAI-1) and carboxypeptidase U (CPU) have also been unsuccessful mainly due to limited drugability, such as poor pharmacokinetic properties of the drug candidates.

The fibrinolytic activity of t-PA is inhibited by plasminogen activator inhibitor 1 (PAI-1) through complex-binding to the t-PA molecule. By virtue of its antifibrinolytic effect, PAI-1 diminishes the ability to dissolve blood clots and thereby increase the risk of clinical thrombotic events (see Hrafnklsdottir et al., *J. Thromb. Haemost.*, 2, 1960-8 (2004)).

PAI-1 circulates in low concentrations in plasma (typically around 5-10 ng/mL in morning samples), but in the population plasma PAI-1 concentration shows a marked right-wardly skewed distribution. Generally, circulating PAI-1 levels increase with age. Elevated PAI-1 levels predispose for thrombotic events. On an individual scale, levels above 100 ng/mL are considered to constitute a significant risk factor for cardiovascular events, even in the absence of other traditional risk factors. Moreover, elevated PAI-1 levels are frequently found in patients with obesity-related metabolic disorders such as Type-2 diabetes mellitus and the metabolic syndrome.

Circulating levels of PAI-1 show a pronounced circadian variation, with peak levels around 06:00 hours and a trough around 16:00 hours as illustrated in FIG. 1 (see also, for example, Scheer and Shea, Blood (2014)). As expected, the morning PAI-1 rise coincides with the temporal peak incidence for thrombotic events, such as myocardial infarction.

Patients with obesity and/or the metabolic syndrome have higher circulating PAI-1 levels and augmented circadian peaks as illustrated in FIG. 1. Plasma concentrations typically range between 15-60 ng/mL in morning samples in these patients, but levels are non-normally distributed with a pronounced positive skewness. Plasma PAI-1 levels between 100-500 mg/mL in morning samples are not infrequently observed in obese patients with the metabolic syndrome. Thus, patients with obesity and/or the metabolic syndrome are at particular risk of suffering thrombotic events resulting from the inhibitory effect of PAI-1 on the action of t-PA.

Therefore, it would be interesting to prevent cardiovascular events by lowering PAI-1, and more specifically to abrogate the early morning rise in its plasma concentration. This approach would theoretically be even more efficient in patients with obesity and/or the metabolic syndrome.

We have now surprisingly found that certain pharmaceutical formulations comprising valproic acid (VPA), and/or pharmaceutically acceptable salts thereof, may allow for delayed release of these active ingredients, which in turns makes such formulations ideally suited for use in treatments based on inhibition of PAI-1.

Thus, administration of such formulations may allow for plasma levels of VPA, and/or pharmaceutically acceptable salts and/or metabolites thereof, to coincide with peak plasma levels of PAI-1, which allows for an advantageous effect in the treatment or prevention of pathological conditions associated with excess fibrin deposition and/or thrombus formation.

WO 2012/120262 discusses the use of HDAC inhibitors, including valproic acid, in improving or normalizing endogenous fibrinolysis impaired by local or systemic inflammation. However, it provides no suggestion that HDAC inhibitors may inhibit the action of PAI-1 and, therefore, does not suggest the development of formulations to counteract (i.e. reduce) peak levels of PAI-1, thus providing a treatment for pathological conditions associated with excess fibrin deposition and/or thrombus formation.

US2007/0232528A1 describes controlled release formulations comprising valproic acid for use in the treatment of disorders such as cancer. These formulations are not designed in a manner than would render them effective for counteracting peak levels of PAI-1.

Description of the Invention

The present invention relates to fibrin degradation or breakdown (also called fibrinolysis), and more particularly compositions and methods for the treatment of pathological conditions associated with excess fibrin deposition and/or thrombus formation.

In particular, the present invention relates to methods of using valproic acid (VPA), or pharmaceutically acceptable salts thereof, in the treatment or prevention of pathological conditions associated with excess fibrin deposition and/or thrombus formation (e.g. thrombus formation).

The present invention also provides pharmaceutical compositions formulated to delay the release of VPA, or pharmaceutically acceptable salts thereof, in a manner suitable for use in such methods.

Medical Treatments

As described herein, it has been found that VPA, or pharmaceutically acceptable salts thereof, is able to inhibit the activity of PAI-1 (e.g. through reduction of PAI-1 levels), which itself is an inhibitor of t-PA. As a consequence, VPA, or pharmaceutically acceptable salts thereof, is able to increase the effects of t-PA and, therefore, is of use in the treatment or prevention of pathological conditions associated with excess fibrin deposition and/or thrombus formation.

In particular, it has been unexpectedly found that human subjects treated with VPA had reduced circulating levels of PAI-1. In healthy men circulating plasma levels of PAI-1 were significantly reduced by more than 50% after VPA treatment and in patients with coronary atherosclerosis by about 45%, which results are further described in Example 1 as provided herein.

The finding that VPA treatment lowers plasma levels of PAI-1 in man was unexpected given that in vitro data from cultured endothelial cells (one of the believed producers of plasma PAI-1) did not show a decrease of PAI-1 mRNA levels after VPA treatment, rather a slight but significant 30% increase in PAI-1 production. These studies also did not detect any effects of VPA on plasma PAI-1 in the in vivo models in pig (see Svennerholm et al., PLoS One. 2014 May 12; 9(5):e97260. doi: 10.1371/journal.pone.0097260. eCollection 2014) or in mouse (Larsson, Alwis et al, J Thromb Haemost. 2016 Dec, 14 (12):2496-2508).

In a first aspect of the invention, there is provided valproic acid (VPA), or a pharmaceutically acceptable salt thereof, for use in treating or preventing a pathological condition associated with excess fibrin deposition and/or thrombus formation, wherein said treatment comprises administering at least one dose of VPA, or a pharmaceutically acceptable salt thereof, to a patient such that the maximum plasma concentration (Cmax) of VPA, or a salt and/or metabolite thereof, in the patient occurs during a time period that is from four hours before to one hour after the maximum plasma concentration (Cmax) of PAI-1 in the patient.

In an alternative first aspect of the invention, there is provided the use of VPA, or a pharmaceutically acceptable salt thereof, in the manufacture of a medicament for use in treating or preventing a pathological condition associated with excess fibrin deposition and/or thrombus formation, wherein said treatment comprises administering at least one dose of VPA, or a pharmaceutically acceptable salt thereof, to a patient such that the maximum plasma concentration (Cmax) of VPA, or a salt and/or metabolite thereof, in the patient occurs during a time period that is from four hours before to one hour after the maximum plasma concentration (Cmax) of PAI-1 in the patient.

In a further alternative first aspect of the invention, there is a method of treating or preventing a pathological condition associated with excess fibrin deposition and/or thrombus formation in a patient in need thereof comprising administering at least one dose of a therapeutically effective amount of VPA, or a pharmaceutically acceptable salt thereof, to a patient such that the maximum plasma concentration (Cmax) of VPA, or a salt and/or metabolite thereof, in the patient occurs during a time period that is from four hours before to one hour after the maximum plasma concentration (Cmax) of PAI-1 in the patient.

The skilled person will understand that references herein to embodiments of particular aspects of the invention will include references to all other embodiments of those aspects of the invention. As such, any one or more embodiments of any aspect of the invention may be combined with any one or more other such embodiments in order to form more particular embodiments, without departing from the disclosure of the invention as provided herein.

As used herein, references to a pathological condition associated with excess fibrin deposition and/or thrombus formation will refer in particular to pathological conditions associated with thrombus formation.

In a particular embodiment of the first aspect of the invention, the maximum plasma concentration (Cmax) of VPA, or a salt (e.g. a pharmaceutically acceptable salt) and/or metabolite thereof, in the patient occurs during a time period that is from four hours before to the time of the maximum plasma concentration (Cmax) of PAI-1 in the patient.

In another particular embodiment of the first aspect of the invention, the maximum plasma concentration (Cmax) of VPA, or a salt and/or metabolite thereof, in the patient occurs during a time period that is from three hours before (e.g. two hours before) to one hour after the maximum plasma concentration (Cmax) of PAI-1 in the patient.

In a more particular embodiment of the first aspect of the invention, the maximum plasma concentration (Cmax) of VPA, or a salt and/or metabolite thereof, in the patient occurs during a time period that is from three hours before (e.g. two hours before) to the time of the maximum plasma concentration (Cmax) of PAI-1 in the patient.

In a second aspect of the invention, there is provided VPA, or a pharmaceutically acceptable salt thereof, for use in treating or preventing a pathological condition associated with excess fibrin deposition and/or thrombus formation, wherein said treatment comprises administering at least one dose of VPA, or a pharmaceutically acceptable salt thereof, to a patient such that at the time when the patient experiences the maximum plasma concentration (Cmax) of PAI-1, the patient has a plasma concentration of VPA, or a salt and/or metabolite thereof, that is at least about 10 to about 100 μg/ml (such as e.g. at least about 10, about 20, about 30, about 40, about 50, about 60, about 70, about 80, about 90 or about 100 μg/ml).

In an alternative second aspect of the invention, there is provided the use of VPA, or a pharmaceutically acceptable salt thereof, in the manufacture of a medicament for use in treating or preventing a pathological condition associated with excess fibrin deposition and/or thrombus formation, wherein said treatment comprises administering at least one dose of VPA, or a pharmaceutically acceptable salt thereof, to a patient such that at the time when the patient experiences the maximum plasma concentration (Cmax) of PAI-1, the patient has a plasma concentration of VPA, or a salt and/or metabolite thereof, that is at least about 10 to about 100 μg/ml (such as e.g. at least about 10, about 20, about 30, about 40, about 50, about 60, about 70, about 80, about 90 or about 100 μg/ml).

In a further alternative second aspect of the invention, there is provided a method of treating or preventing a pathological condition associated with excess fibrin deposition in a patient in need thereof comprising administering at least one therapeutically effective dose of VPA, or a pharmaceutically acceptable salt thereof, to a patient such that at the time when the patient experiences the maximum plasma concentration (Cmax) of PAI-1, the patient has a plasma concentration of VPA, or a salt and/or metabolite thereof, that is at least about 10 to about 100 µg/ml (such as e.g. at least about 10, about 20, about 30, about 40, about 50, about 60, about 70, about 80, about 90 or about 100 µg/ml).

As used herein, the reference to an amount per millilitre (/ml) will be understood to refer to an amount per millilitre of plasma (i.e. blood plasma of the patient). As used herein, the reference to molar concentration will be understood to refer to a concentration in plasma (i.e. blood plasma of the patient).

In particular embodiments, the patient may have a concentration of VPA, or a salt and/or metabolite thereof, that is below about 50 to about 170 µg/ml (such as e.g. below about 50, about 70, about 90, about 110, about 130, about 150, or about 170 µg/ml).

In further such embodiments, the patient has a plasma concentration of valproic acid, or a salt and/or metabolite thereof, that is at least about 70 to about 700 µM (such as e.g. at least about 70, about 140, about 210, about 280, about 350, about 420, about 490, about 560, about 630 or about 700 µM).

In yet further such embodiments, the patient has a plasma concentration of valproic acid, or a salt and/or metabolite thereof, that is below about 350 to about 1200 µM (such as e.g. below about 350, about 490, about 630, about 770, about 910, about 1050, or about 1190 µM).

For the avoidance of doubt, the skilled person will understand that references herein to certain maximum amounts and concentrations in plasma may also require a minimum of a therapeutically effective amount in said plasma.

In particular, the skilled person will understand that references to certain maximum (i.e. where values are indicated as being "below") and minimum (i.e. where values are indicated as being "at least") amount and/or concentrations in plasma may be combined to form ranges (i.e. wherein the amount in plasma is in a range that is from the minimum value to the maximum value).

For example, in one embodiment of the second aspect of the invention, the patient has a plasma concentration of valproic acid, or a salt and/or metabolite thereof, that is about 10 to about 170 µg/ml.

In other such embodiments, the patient has a plasma concentration of valproic acid, or a salt and/or metabolite thereof, that is:

from about 10 to about 70 ug/ml (or from about 50 to about 90, about 70 to about 110, about 90 to about 130, about 110 to about 150, about 130 to about 170, or about 150 to about 190 ug/ml);

from about 10 to about 50 ug/ml (e.g. from about 10 and to about 100, about 30 to about 120, about 50 to about 170, or about 70 to about 190 ug/ml); or from about 30 to about 190 ug/ml (e.g. about 50 to about 170, about 70 to about 150, about 90 to about 130, about 30 to about 110, about 50 to about 130, or about 70 to about 170 ug/ml).

The skilled person will understand that references to certain minimum plasma levels herein (e.g. in the second aspect of the invention) will include references to such levels at a time when the patient has reached a steady state of VPA, or a salt and/or metabolite thereof, in plasma. Moreover, the skilled person will understand that references to the patient reaching a steady state may refer to the plasma levels achieved after said patient has been treated with VPA (at a therapeutically-effective dose thereof) for at least two to five days (e.g. at least five days).

The skilled person will also understand that the references to maximum and minimum plasma levels in the second aspect of the invention (including all embodiments and alternative aspects thereof) may also apply to the plasma levels observed for the Cmax of VPA, or a salt and/or metabolite thereof, as referred to in other aspects of the invention (such as the first aspect of the invention).

In a third aspect of the invention, there is provided VPA, or a pharmaceutically acceptable salt thereof, for use in treating or preventing a pathological condition associated with excess fibrin deposition and/or thrombus formation, wherein said treatment comprises administering a dose of VPA, or a pharmaceutically acceptable salt thereof, to a patient during a time period from about 20:00 hours to about 06:00 hours.

In an alternative third aspect of the invention, there is provided the use of VPA, or a pharmaceutically acceptable salt thereof, in the manufacture of a medicament for use in treating or preventing a pathological condition associated with excess fibrin deposition and/or thrombus formation, wherein said treatment comprises administering a dose of VPA, or a pharmaceutically acceptable salt thereof, to a patient during a time period from about 20:00 hours to about 06:00 hours.

In a further alternative third aspect of the invention, there is provided a method of treating or preventing a pathological condition associated with excess fibrin deposition and/or thrombus formation in a patient in need thereof comprising administering a therapeutically effective dose of VPA, or a pharmaceutically acceptable salt thereof, to a patient during a time period from about 20:00 hours to about 06:00 hours.

In a particular embodiment of the third aspect of the invention, the treatment comprises administering a therapeutically effective dose of VPA, or a pharmaceutically acceptable salt thereof, to a patient during a time period from about 21:00 hours to about 05:00 hours (e.g. about 22:00 hours to about 04:00 hours).

In a particular embodiment of the third aspect of the invention (particularly wherein the treatment is administered as a pharmaceutical composition that is not formulated for delayed release of the active ingredient), the treatment comprises administering a therapeutically effective dose of VPA, or a pharmaceutically acceptable salt thereof, to a patient during a time period from about 02:00 hours to about 06:00 hours (e.g. about 03:00 hours to about 05:00 hours, such as about 04:00 hours).

In another particular embodiment of the third aspect of the invention (particularly wherein the treatment is administered as a pharmaceutical composition that is formulated for delayed release of the active ingredient, such as those described in the eight aspect of the invention herein), the treatment comprises administering a therapeutically effective dose of VPA, or a pharmaceutically acceptable salt thereof, to a patient during a time period from about 20:00 hours to about 00:00 hours (e.g. about 21:00 hours to about 23:00 hours, such as at about 22:00 hours). In an alternative such embodiment, the time period is from about 18:00 hours to about 22:00 hours.

In an alternative embodiment of the third aspect of the invention, the treatment comprises administering a therapeutically effective dose of VPA, or a pharmaceutically acceptable salt thereof, to a patient during a time period from about 18:00 hours to about 06:00 hours (e.g. about 18:00 hours to about 00:00 hours, such as about 18:00 hours to about 22:00 hours).

In further alternative embodiments of the third aspect of the invention, the treatment comprises administering a therapeutically effective dose of VPA, or a pharmaceutically acceptable salt thereof, to a patient during a time period determined based on the release profile of that formulation in order to provide a plasma concentration of VPA, or a salt and/or metabolite thereof, as required in the first and/or second aspect of the invention.

As described herein, the skilled person will be able to determine how to administer compounds of the invention in a manner (e.g. during a certain time period) in order to achieve parameters described herein (such as those described in the first and second aspects of the invention).

For the avoidance of doubt, in particular embodiments of the third aspect of the invention, the dose referred to is a single dose, which will indicate that the dose is the only dose of the compound given to the patient during a (e.g. the relevant) 24 hour period.

In a fourth aspect of invention, there is provided VPA, or a pharmaceutically acceptable salt thereof, for use in treating or preventing a pathological condition associated with excess fibrin deposition and/or thrombus formation, wherein said treatment comprises administering a pharmaceutical composition comprising a dose of VPA, or a pharmaceutically acceptable salt thereof, to a patient at a time and in a form such that substantially all of the VPA, or a pharmaceutically acceptable salt thereof, is released from the composition during a time period from about 02:00 hours to about 06:00 hours.

In an alternative fourth aspect of invention, there is provided the use of VPA, or a pharmaceutically acceptable salt thereof, in the manufacture of a medicament for use in treating or preventing a pathological condition associated with excess fibrin deposition and/or thrombus formation, wherein said treatment comprises administering a pharmaceutical composition comprising a dose of VPA, or a pharmaceutically acceptable salt thereof, to a patient at a time and in a form such that substantially all of the VPA, or a pharmaceutically acceptable salt thereof, is released from the composition during a time period from about 02:00 hours to about 06:00 hours.

In a further alternative fourth aspect of invention, there is provided a method of treating or preventing a pathological condition associated with excess fibrin deposition and/or thrombus formation in a patient in need thereof comprising administering a pharmaceutical composition comprising a therapeutically effective dose of VPA, or a pharmaceutically acceptable salt thereof, to a patient at a time and in a form such that substantially all of the VPA, or a pharmaceutically acceptable salt thereof, is released from the composition during a time period from about 02:00 hours to about 06:00 hours.

In a particular embodiment of the fourth aspect of the invention, the treatment comprises administering a pharmaceutical composition comprising a therapeutically effective dose of VPA, or a pharmaceutically acceptable salt thereof, to a patient at a time and in a form such that substantially all of the VPA, or a pharmaceutically acceptable salt thereof, is released from the composition during a time period from about 03:00 hours to about 05:00 hours (e.g. from about 04:00 hours to about 05:00 hours, such as at about 05:00 hours).

The skilled person will understand that timings refered to using the 24-hour system may also be referred to as timings using the 12-hour system (i.e. with AM and PM denoting times before and after 12:00 noon, respectively). For example, 20:00 may also be referred to as 8:00 PM, and 06:00 as 6:00 AM.

In a particular embodiment of the fourth aspect of the invention, the treatment comprises administering a pharmaceutical composition as described in further aspects of the invention as described herein below (including all embodiments thereof).

In a fifth aspect of the invention, there is provided VPA, or a pharmaceutically acceptable salt thereof, for use in treating or preventing a pathological condition associated with excess fibrin deposition and/or thrombus formation in a patient, wherein said treatment comprises:
  (i) monitoring the plasma concentration of PAI-1 in the patient in order to determine the time at, or time period during which, the maximum plasma concentration of PAI-1 occurs;
  (ii) administering at least one dose of VPA, or a pharmaceutically acceptable salt thereof, to the patient such that the maximum plasma concentration (Cmax) of VPA, or a salt and/or metabolite thereof, in the patient occurs during a time period that is from four hours before to one hour after the time at which, or time period during which, the maximum plasma concentration of PAI-1 occurs.

In an alternative fifth aspect of the invention, there is provided the use of VPA, or a pharmaceutically acceptable salt thereof, in the manufacture of a medicament for use in treating or preventing a pathological condition associated with excess fibrin deposition and/or thrombus formation in a patient, wherein said treatment comprises:
  (i) monitoring the plasma concentration of PAI-1 in the patient in order to determine the time at, or time period during which, the maximum plasma concentration of PAI-1 occurs; and
  (ii) administering at least one dose of VPA, or a pharmaceutically acceptable salt thereof, to the patient such that the maximum plasma concentration (Cmax) of VPA, or a salt and/or metabolite thereof, in the patient occurs during a time period that is from four hours before to one hour after the time at which, or time period during which, the maximum plasma concentration of PAI-1 occurs.

In a further alternative fifth aspect of the invention, there is provided a method of treating or preventing a pathological condition associated with excess fibrin deposition and/or thrombus formation in a patient in need thereof comprising the steps of:
  (i) monitoring the plasma concentration of PAI-1 in the patient in order to determine the time at, or time period during which, the maximum plasma concentration of PAI-1 occurs; and
  (ii) administering at least one therapeutically effective dose of VPA, or a pharmaceutically acceptable salt thereof, to the patient such that the maximum plasma concentration (Cmax) of VPA, or a salt and/or metabolite thereof, in the patient occurs during a time period that is from four hours before to one hour after the time at which, or time period during which, the maximum plasma concentration of PAI-1 occurs.

As described herein, plasma concentrations of PAI-1 may be monitored using techniques well-known to those skilled in the art. For instance, PAI-1 levels are generally measured in plasma. Blood may be collected from an antecubital syringe regularly e.g. every hour, every second hour or every third hour throughout 24 hours. The blood samples are immediately centrifuged to separate plasma from the serum. Thereafter PAI-1 levels in plasma are determined by using commercially available ELISA-kits, such as Coaliza® PAI-1 (Chromogenix), TriniLIZE® PAI-1 (Trinity Biotech), Imubind® Plasma PAI-1 (American Diagnostica), Zymutest PAI-1 (Hyphen Biomed), Milliplex PAI-1 (MerckMillipore), Novex PAI-1 human Elisa kit (Life technology), PAI1 (SERPINE1) Human ELISA Kit (Abcam, ab108891).

Alternatively, references to monitoring of the patient may refer to determining the general state of the patient (such as the patient's age, sex and/or general health) and determining the time at, or time period during which, the maximum plasma concentration of PAI-1 occurs by reference to parameters observed in corresponding patient groups.

In a particular embodiment of the fifth aspect of the invention, the maximum plasma concentration (Cmax) of VPA, or a salt and/or metabolite thereof, in the patient occurs during a time period that is from four hours before (e.g. three hours before, such as 2 hours before or 1 hour before or 0.5 hours before) to the time of the maximum plasma concentration (Cmax) of PAI-1 in the patient.

In another particular embodiment of the fifth aspect of the invention, the maximum plasma concentration (Cmax) of VPA, or a salt and/or metabolite thereof, in the patient occurs during a time period that is from three hours before (e.g. two hours before) to one hour after the maximum plasma concentration (Cmax) of PAI-1 in the patient.

In a more particular embodiment of the fifth aspect of the invention, the maximum plasma concentration (Cmax) of VPA, or a salt and/or metabolite thereof, in the patient occurs during a time period that is from three hours before (e.g. two hours before) to the time of the maximum plasma concentration (Cmax) of PAI-1 in the patient.

The skilled person will understand that the timing and level of the Cmax of VPA, or a salt or metabolite thereof, will depend on the dose administered (and, to some extent, the form in which that dose is administered). The skilled person will be able to measure the plasma concentration of VPA, or a metabolite and/or salt thereof, and determine the timing and level of the Cmax (and, if necessary, to adjust the dose and form of VPA administered accordingly). Particular doses (i.e. therapeutic doses) of VPA that may be administered and Cmax levels that may be obtained include those as described herein.

In a sixth aspect of the invention, there is provided VPA, or a pharmaceutically acceptable salt thereof, for use in treating or preventing a pathological condition associated with excess fibrin deposition and/or thrombus formation in a patient, wherein said treatment comprises:
(i) monitoring the plasma concentration of PAI-1 in the patient in order to determine the time at, or time period during which, the maximum plasma concentration of PAI-1 occurs; and
(ii) administering at least one dose of VPA, or a pharmaceutically acceptable salt thereof, to the patient such that at the time when the patient experiences the maximum plasma concentration of PAI-1, the patient has a plasma concentration of VPA, or a salt and/or metabolite thereof, that is that is at least about 10 to about 100 µg/ml (such as e.g. at least about 10, about 20, about 30, about 40, about 50, about 60, about 70, about 80, about 90 or about 100 µg/ml).

In an alternative sixth aspect of the invention, there is provided the use of VPA, or a pharmaceutically acceptable salt thereof, in the manufacture of a medicament for use in treating or preventing a pathological condition associated with excess fibrin deposition and/or thrombus formation in a patient, wherein said treatment comprises:
(i) monitoring the plasma concentration of PAI-1 in the patient in order to determine the time at, or time period during which, the maximum plasma concentration of PAI-1 occurs; and
(ii) administering at least one dose of VPA, or a pharmaceutically acceptable salt thereof, to the patient such that at the time when the patient experiences the maximum plasma concentration of PAI-1, the patient has a plasma concentration of VPA, or a salt and/or metabolite thereof, that is that is at least about 10 to about 100 µg/ml (such as e.g. at least about 10, about 20, about 30, about 40, about 50, about 60, about 70, about 80, about 90 or about 100 µg/ml).

In a further alternative sixth aspect of the invention, there is provided a method of treating or preventing a pathological condition associated with excess fibrin deposition and/or thrombus formation in a patient in need thereof comprising the steps of:
(i) monitoring the plasma concentration of PAI-1 in the patient in order to determine the time at, or time period during which, the maximum plasma concentration of PAI-1 occurs; and
(ii) administering at least one therapeutically effective dose of VPA, or a pharmaceutically acceptable salt thereof, to the patient such that at the time when the patient experiences the maximum plasma concentration of PAI-1, the patient has a plasma concentration of VPA, or a salt and/or metabolite thereof, that is that is at least about 10 to about 100 µg/ml (such as e.g. at least about 10, about 20, about 30, about 40, about 50, about 60, about 70, about 80, about 90 or about 100 µg/ml).

In particular embodiments, the patient may have a plasma concentration of VPA, or a salt and/or metabolite thereof, that is below about 50 to about 170 µg/ml (such as e.g. below about 50, about 70, about 90, about 110, about 130, about 150, or about 170 µg/ml).

In further embodiments, the patient has a plasma concentration of VPA, or a salt and/or metabolite thereof, that is at least about 70 to about 700 µM (such as e.g. at least about 70, about 140, about 210, about 280, about 350, about 420, about 490, about 560, about 630 or about 700 µM).

In yet further embodiments, the patient has a plasma concentration of VPA, or a salt and/or metabolite thereof, that is below about 350 to about 1200 µM (such as e.g. below about 350, about 490, about 630, about 770, about 910, about 1050, or about 1190 µM).

Again, the skilled person will understand that references to certain maximum amounts and concentrations in plasma in the sixth aspect of the invention may also require a minimum of a therapeutically effective amount in said plasma. Moreover, the skilled person will understand that references to certain maximum (i.e. where values are indicated as being "below") and minimum (i.e. where values are indicated as being "at least") amount and/or concentrations in plasma may be combined to form ranges (i.e. wherein the amount in plasma is in a range that is from the minimum value to the maximum value).

For example, in one embodiment of the sixth aspect of the invention, the patient has a plasma concentration of VPA, or a salt and/or metabolite thereof, that is about 10 to about 170 µg/ml. In other such embodiments, the patient has a plasma concentration of VPA, or a salt and/or metabolite thereof, that is:
from about 10 to about 70 ug/ml (or from about 50 to about 90, about 70 to about 110, about 90 to about 130, about 110 to about 150, about 130 to about 170, or about 150 to about 190 ug/ml);
from about 10 to about 50 ug/ml (e.g. from about 10 and to about 100, about 30 to about 120, about 50 to about 170, or about 70 to about 190 ug/ml);

from about 30 to about 190 ug/ml (e.g. about 50 to about 170, about 70 to about 150, about 90 to about 130, about 30 to about 110, about 50 to about 130, or about 70 to about 170 ug/ml).

In a seventh aspect of the invention, there is provided VPA, or a pharmaceutically acceptable salt thereof, for use in treating or preventing a pathological condition associated with excess fibrin deposition and/or thrombus formation, wherein said treatment comprises administering a single dose of VPA, or a pharmaceutically acceptable salt thereof, to a patient in a 24 hour period.

In an alternative seventh aspect of the invention, there is provided the use of VPA, or a pharmaceutically acceptable salt thereof, in the manufacture of a medicament for use in treating or preventing a pathological condition associated with excess fibrin deposition and/or thrombus formation, wherein said treatment comprises administering a single dose of VPA, or a pharmaceutically acceptable salt thereof, to a patient in a 24 hour period.

In a further alternative seventh aspect of the invention, there is provided a method of treating or preventing a pathological condition associated with excess fibrin deposition and/or thrombus formation in a patient in need thereof comprising administering a single, therapeutically effective dose of VPA, or a pharmaceutically acceptable salt thereof, to a patient in a 24 hour period.

Unless otherwise stated or apparent from the context (e.g. when discussed in reference to a specific formulation), references to the dose of compounds of the invention (e.g. the dose of valproic acid or a pharmaceutically acceptable salt thereof) will be understood to refer to a therapeutically effective dose thereof. Moreover, the dose of such compounds may refer to the dose of the compound itself (e.g. the dose of valproic acid itself), or the effective (i.e. equivalent) dose of the compound when administered in the form that includes or consists of one or more salt thereof (e.g. one or more salt of valproic acid).

The skilled person will be able to determine what constitutes a therapeutically effective dose of compounds of the invention by recourse to the scientific literature published in relation to such compounds.

In a particular embodiment of the seventh aspect of the invention (including all alternative aspects and/or embodiments thereof), the dose administered in the 24 hour period is from about 10 mg to about 2000 mg, from about 50 mg to about 1300 mg (such as about 100 mg to about 1200 mg) or from about 50 mg to about 1000 mg (such as about 100 mg to about 800 mg, about 100 mg to about 600 mg, or about 200 mg to about 600 mg, e.g. such as about 100 mg to about 800 mg, or about 200 mg to about 600 mg).

For the avoidance of doubt, the skilled person will understand that doses as described herein may be administered in a single dosage unit or a combination of units each comprising a portion of the required dose. For example, a dose of 520 mg may be administered as two units each comprising 260 mg, four units each comprising 130 mg, or similar combinations.

In a particular embodiment of the seventh aspect of the invention (including all alternative aspects and/or embodiments thereof), the dose administered in the 24 hour period is from about 100 mg to about 600 mg, such as about 120 mg to about 540 mg (e.g. about 130 mg or about 260 mg, or about 390 mg or about 520 mg, which latter two doses may be administered as two separate doses, at appropriate intervals (such as those described herein), such as one dose of about 130 mg and one dose of about 260 mg, or two doses of about 260 mg (which latter dose may be administered as two units comprising each 130 mg)).

Alternatively, where treatment as described herein requires administration of two separate doses during a 24 hour period (e.g. as a morning dose and an evening dose), the evening dose may be from about 100 mg to about 600 mg, such as about 120 mg to about 540 mg (e.g. about 130 mg or about 260 mg, or about 390 mg or about 520 mg, which latter two doses may be administered as two separate doses, at appropriate intervals (such as those described herein), such as one dose of about 130 mg and one dose of about 260 mg, or two doses of about 260 mg (which latter dose may be administered as two units comprising each 130 mg)). In such instances, there may be a corresponding morning dose of about 10 mg to about 500 mg, which may be administered in similar units.

Unless otherwise stated or apparent from the context (e.g. when discussed in reference to a specific formulation), references to the dose of VPA will be understood to refer to the dose of VPA, or the effective (i.e. equivalent) dose of VPA when administered in the form that includes or consists of one or more salt thereof.

In a particular embodiment of the seventh aspect of the invention, the dose is from about 200 mg to about 500 mg, such as about 230 mg, about 280 mg, about 320 mg, about 380 mg, about 450 mg or about 490 mg. In another particular embodiment of the seventh aspect of the invention, the dose is from about 220 mg to about 560 mg, such as about 240 mg to about 530 mg, about 280 mg to about 560 mg, about 240 mg, about 270 mg, about 310 mg, about 370 mg, about 410 mg, about 460 mg or about 530 mg. In another particular embodiment of the seventh aspect of the invention, the dose is from about 300 mg to about 500 mg, such as about 360 mg or about 470 mg. In another particular embodiment of the seventh aspect of the invention, the dose is from about 400 mg to about 600 mg, such as about 450 or about 550 mg. In another particular embodiment of the seventh aspect of the invention, the dose is from about 400 mg to about 800 mg, such as about 575, about 650 or about 700 mg.

In a more particular embodiment, the dose is from about 200 mg to about 400 mg, such as about 400 or about 300 mg. In another particular embodiment, the dose is from about 300 mg to about 500 mg, such as about 350 mg.

Again, for the avoidance of doubt, all references herein to particular aspects of the invention (e.g. the first aspect of the invention) will include references to all alternative such aspects of the invention (e.g. the alternative and further alternative first aspects of the invention).

Moreover, the skilled person will understand that all embodiments, preferences, particular definitions and the like referred to herein may be combined with any one or more other embodiments, preferences, particular definitions and the like also referred to herein.

When used herein in reference to a value or an amount (including an amount of time), the terms "about", "around" and "approximately" will be understood as referring to a value that is within 10% of the value defined. When used herein in reference to a specific point in time (including the start or end of a period of time), the terms "about" and "around" will be understood as referring to a value that is within 30 minutes (e.g. within 20 minutes, such as within 10 minutes) of that specific time. Further, it is contemplated that each reference to the terms "about", "around" and "approximately" (e.g. in relation to times and amounts) may be deleted throughout.

As used herein, the term "compounds of the invention" will refer to VPA and pharmaceutically acceptable salts thereof. The skilled person will understand that references to VPA and pharmaceutically acceptable salts thereof (e.g. references to "valproic acid (VPA), or a pharmaceutically acceptable salt thereof") may include references to mixtures of VPA and different pharmaceutically acceptable salts thereof, and references to mixtures of such salts, all of which may be referred to as compounds of the invention.

As used herein, the skilled person will understand that references to "preventing" a particular condition may also be referred to as "prophylaxis" of said condition, and vice versa. Thus, each reference herein to "preventing" a condition may be replaced with a reference to "prophylaxis" of said condition.

The skilled person will understand that the terms "treatment" and "treating" when used herein take their normal meanings in the field of medicine. In particular, these terms may refer to achieving a reduction in the severity of one or more clinical symptom associated with the relevant condition.

The skilled person will also understand that the terms "prevention" and "preventing" when used herein take their normal meanings in the field of medicine. In particular, these terms may refer to achieving a reduction in the likelihood of developing the relevant condition (for example, a reduction of at least 10% when compared to the baseline level, such as a reduction of at least 20% or, more particularly, a reduction of at least 30%).

As used herein, the terms "prevention" and "preventing" when used in relation to a medical condition may also be referred to as prophylaxis of that condition.

The skilled person will also understand that references to prevention (or prophylaxsis) of a particular condition may also include the treatment of another condition. For example, treatment of a primary condition may also be considered to be a form of prevention (or prophylaxsis) of a secondary condition.

In particular embodiments of the first to seventh aspects of the invention (including all alternative aspects), there are provided compounds for use in (and/or uses in and/or methods for) preventing a pathological condition associated with excess fibrin deposition and/or thrombus formation (particularly, thrombus formation).

As used herein, the term "pathological conditions" will be understood to refer to identifiable diseases or disorders.

As described herein, pathological conditions that may be treated or prevented in accordance with the invention associated with excess fibrin deposition and/or thrombus formation. These include, but are not limited to, atherosclerosis, myocardial infarction, ischemic stroke, deep vein thrombosis, superficial vein thrombosis, thrombophlebitis, pulmonary embolism, disseminated intravascular coagulation, renal vascular disease and intermittent claudication (e.g. atherosclerosis, myocardial infarction, ischemic stroke, deep vein thrombosis, pulmonary embolism, disseminated intravascular coagulation, renal vascular disease and intermittent claudication).

Thus, in particular embodiments of the first to seventh aspects of the invention, the pathological condition associated with excess fibrin deposition and/or thrombus formation is selected from the group consisting of atherosclerosis, myocardial infarction, ischemic stroke, deep vein thrombosis, pulmonary embolism, disseminated intravascular coagulation, renal vascular disease and intermittent claudication.

Thus, in more particular embodiments of the first to seventh aspects of the invention, the pathological condition associated with excess fibrin deposition and/or thrombus formation is selected from the group consisting of myocardial infarction, ischemic stroke and pulmonary embolism.

In other more particular embodiments of the first to seventh aspects of the invention, the pathological condition associated with excess fibrin deposition and/or thrombus formation is selected from the group consisting of myocardial infarction and ischemic stroke (such as myocardial infarction).

The skilled person will understand that references to ischemic stroke include references to major stroke events (i.e. those caused by prolonged impairment of blood flow), minor strokes and transient ischemic attacks (TIAs).

Thus, in more particular embodiments of the first to seventh aspects of the invention, the pathological condition associated with excess fibrin deposition and/or thrombus formation is ischemic stroke, such as a major ischemic stroke, minor ischemic stroke or a TIA.

In even more particular embodiments of the first to seventh aspects of the invention, the pathological condition associated with excess fibrin deposition and/or thrombus formation is ischemic stroke, such as a major ischemic stroke and minor ischemic stroke.

In particular, it is believed that compounds of the invention, when administered in accordance with the dosage regimes defined above (e.g. in the first to seventh aspects of the invention), may be of particular use in preventing a pathological condition associated with excess fibrin deposition and/or thrombus formation (such as ischemic stroke and/or myocardial infarction). Thus, all references to treating and preventing such conditions herein will include particular references to preventing such conditions.

Thus, in yet more particular embodiments of the first to seventh aspects of the invention, treating or preventing a pathological condition associated with excess fibrin deposition and/or thrombus formation will refer to preventing ischemic stroke, such as a major ischemic stroke, minor ischemic stroke or a TIA.

As discussed above, thrombotic cardiovascular events occur as a result of two distinct processes, i.e. a slowly progressing long-term vascular atherosclerosis of the vessel wall, on the one hand, and a sudden acute clot formation that rapidly causes flow arrest, on the other. Particular pathological conditions that may be treated are those relating to the latter process.

In particular embodiments of the first to seventh aspects of the invention, pathological conditions that may be treated or prevented in accordance with the invention are those that are caused wholly or at least in part by an increased fibrin deposition and/or reduced fibrinolytic capacity due to local or systemic inflammation. These include, but are not limited to, myocardial infarction, stable angina pectoris, unstable angina pectoris, acute coronary syndromes, intermittent claudication, ischemic stroke, transient ischemic attack, deep vein thrombosis and pulmonary embolism. These conditions may display elevated PAI-1 levels in plasma.

In particular embodiments of the first to seventh aspects of the invention, the pathological condition may be selected from the group consisting of deep vein thrombosis and pulmonary embolism.

In particular embodiments of the first to seventh aspects of the invention, the pathological condition is deep vein thrombosis.

In particular embodiments of the first to seventh aspects of the invention, the pathological condition may be selected from the group consisting of superficial vein thrombosis and thrombophlebitis.

In particular embodiments of the first to seventh aspects of the invention, the pathological condition may be acute coronary syndromes (including unstable angina, non-ST elevation myocardial infarction, ST-elevation myocardial infarction).

In more particular embodiments of the first to seventh aspects of the invention, the pathological condition is superficial vein thrombosis.

In more particular embodiments of the first to seventh aspects of the invention, the pathological condition is thrombophlebitis.

In addition, pathological conditions that can be treated in accordance with the invention are those that are caused wholly or at least in part by an increased fibrin deposition and/or reduced fibrinolytic capacity due to local or systemic inflammation. These include but are not limited to atherosclerosis, the metabolic syndrome, diabetes, disseminated intravascular coagulation, rheumatoid arthritis, glomerulo-nephritis, systematic lupus erythematosis, vasculitides, autoimmune neuropathies, and granulomatous disease as well as inflammation associated with other conditions (such as the metabolic syndrome, diabetes, disseminated intravascular coagulation, rheumatoid arthritis, glomerulo-nephritis, systematic lupus erythematosis, vasculitides, autoimmune neuropathies, and granulomatous disease as well as inflammation associated with other conditions).

In addition to traditional diagnosis of a systemic or local inflammation by a physician as is known in the art, a local or systemic inflammation can be determined in patients using one or more biomarkers coupled to inflammation. These biomarkers include, but are not limited to, C reactive protein, TNF-alpha, high sensitive C-reactive protein (hs-CRP), fibrinogen, IL-1beta, and IL-6. Particular methods for determining whether a patient has systemic or local inflammation include those described hereinafter.

In addition, atherosclerotic plaques are known to be associated with a very localized inflammatory process. Hence, local inflammation may also be indirectly determined by the presence of atherosclerotic plaques as diagnosed by vascular ultrasound or other imaging techniques.

The skilled person will understand that, to identify a poor level of fibrinolysis in a patient (i.e. reduced fibrinolytic capacity), there are a few different alternatives available. For example, high circulating levels of PAI-1 are generally considered to be indicative of poor fibrinolysis, and this can be measured in plasma by commercially available methods (including but not limited by Coaliza® PAI-1 (Chromgenix), TriniLIZE® PAI-1 (Trinity Biotech), Imubind® Plasma PAI-1 (American Diagnostica), Zymutest PAI-1 (Hyphen Biomed), Milliplex PAI-1 (MerckMillipore), Novex PAI-1 human Elisa kit (Life technology), PAI1 (SERPINE1) Human ELISA Kit (Abcam, ab108891)). Further, low systemic levels of free, active t-PA is also an indicator of general poor fibrinolysis and can also be measured by commercial methods (TriniLIZE® t-PA antigen and activity (Trinity Biotech), as is the presence of a low-producer (T) genotype of the t-PA -7351 C/T polymorphism. Functional assays measuring clot lysis time have also been used to assess global fibrinolysis (Thrombinoscope™ (Synapse, BV, Maastricht, the Netherlands), IL/ROTEM® (Term International GmbH, Munich, Germany), TEG® (Haemoscope, Niles), CloFAL assay (Peikang Biotechnology Co. Ltd. Shanghai, China)).

The skilled person will understand that whether the increased fibrin deposition and/or reduced fibrinolytic capacity is due to "local or systemic inflammation" as used herein can be determined using one or more biomarkers coupled to inflammation, including but not limited to C reactive protein, TNF-alpha, high sensitive C-reactive protein (hs-CRP), fibrinogen, IL-1beta, and IL-6 (e.g. by increased concentration of one or more of these biomarkers in relation to control levels as known in the art). Commercial analytical platforms that can be used to quantify these biomarkers include, but are not limited to, Afinion™ (Medinor AB, Sweden), CA-7000 (Siemens Healthcare Diagnostics Inc., NY, US), Immulite® 2000 Immunoassay System (Siemens Healthcare Diagnostics Inc.).

Particular biomarkers that may identify local or systemic inflammation include high sensitive C-reactive protein (hs-CRP) (at or above 2.0 mg/l serum) and fibrinogen (at or above 3 g/l serum) (Corrado E., et al. An update on the role of markers of inflammation in atherosclerosis, Journal of atherosclerosis and Thrombosis, 2010; 17:1-11, Koenig W., Fibrin(ogen) in cardiovascular disease: an update, Thrombosis Haemostasis 2003; 89:601-9).

Unless otherwise specified, as used herein, the term "patient" includes mammalian patients (such as equines, cattle, swine, sheep, goats, primates, mice, rats, and pets in general including dogs, cats, guinea pigs, ferrets, and rabbits). In particular, the term "patient" refers to humans.

As used herein, the skilled person will understand that references to plasma will refer to the blood plasma of the patient.

As used herein, the skilled person will understand that references to the maximum plasma concentration (or "Cmax") of a particular substances will refer to the maximum concentration of that agent in blood plasma (i.e. the blood plasma of the patient). In the context of the administration of that agent, the Cmax will refer to that occurring as a direct result of such administration (i.e. the Cmax occurring as a result of the absorption of that agent).

As used herein, the time at which the Cmax of a particular substance occurs may also be referred to as the Tmax.

The skilled person will understand that the Cmax may occur at a specific time (i.e. a particular peak in plasma concentration) or for a prolonged period (i.e. where the plasma concentration reaches a plateau), both of which may be referred to as the time at which the Cmax occurs (the Tmax). Where the Cmax occurs for a prolonged period, the time at which the Cmax occurs may also be taken to the mid-point of that period, although it is generally understood that the Cmax will occur as a clearly distinguishable peak at a specific time.

As described herein, the plasma concentration of PAI-1 in a patient (particularly a human) is known to follow a circadian rhythm. Typically, the maximum plasma concentration (Cmax) of PAI-1 is expected to occur at around 06:00 hours.

Thus, references herein to the time at which the Cmax of PAI-1 occurs may be replaced with a reference to about 06:00 hours.

All absolute times (i.e. specific points in time and periods defined as being between specific points in time) indicated herein refer to the actual local time (i.e. the 'clock' time) experienced by the patient. Moreover, said times assume that the patient is adjusted to local time (for example, having had adequate time to adjust to changes in time zone or so-called "daylight savings" time adjustments).

The skilled person will understand that the timing of the maximum plasma concentration of PAI-1 and compounds of the invention (or salts and/or metabolites thereof) may be determined using techniques that are well known to those skilled in the art, such as by monitoring the concentration of PAI-1 and compounds of the invention (or salts and/or metabolites thereof) in plasma during the relevant time period.

As described herein, plasma levels of compounds of the invention (or salts and/or metabolites thereof) may be monitored using techniques well-known to those skilled in the art. For example, valproate plasma levels are determined in clinical routine e.g. by using a homogeneous enzyme immunoassay technique, based on competition of antibodies between valproate in the sample and enzyme-labelled valproate added to the test (e.g. VALP2, Roche/Cobas, art nr 05108438190 (Roche Diagnostics Scandinavia AB). When the enzyme-labelled valproate is bound to the antibody, the enzyme Glucose 6-phosphate dehydrogenase, (G6PDH) is blocked and cannot consume the test enzyme substrate. Conversely, when the enzyme-labelled valproate is not bound to the antibody, the substrate is available to the enzyme and can be consumed. The consumption of the substrate is measured indirectly by formation of NADH from NAD (coenzyme reaction). NADH absorbs UV light selectively at 340 nm. This means that high valproate concentration in the sample gives a large change in absorbance at 340 nm; conversely at low valproate concentration, there may be a small change in absorbance at 340 nm. The consumption of substrate gives rise to a colour change that is measured photochromatically at 340 and 415 nm. The absorbance is directly proportional to the valproate concentration in the sample.

The skilled person will be able to identify compounds present in plasma as being metabolites of compounds of the invention. Particular metabolites of compounds of the invention that may be mentioned include the valproate anion (e.g. metabolites that comprise a valproate anion moiety).

The skilled person will understand that references to monitoring the plasma concentration (i.e. the blood plasma concentration in the patient) of PAI-1 may refer to monitoring over at least one (e.g. one) 24 hour period (e.g. prior to the beginning of treatment with compounds of the invention). Such monitoring may be continuous or may involve the taking of measurements at set intervals during this period (which may mean that, particularly in the latter case, the time between the first and last measurement is less than 24 hours, such as around 20 hours).

The skilled person will also understand that such monitoring may instead be conducting for a period of time that is expected to include the Cmax of PAI-1, as estimated by a person skilled in the art. For example, where the Cmax of PAI-1 is expected to occur at around 06:00 hours, such monitoring may take place at from 04:00 hours to 08:00 hours (e.g. from 05:00 hours to 07:00 hours).

The timing and size of the dose of compounds of the invention administered will also result in low plasma concentrations of VPA, or a salt and/or metabolite thereof, at specific times.

In a particular embodiment of the first to seventh aspects of the invention, administration of the compounds of the invention is such that the plasma concentration of VPA, or a salt and/or metabolite thereof, during the period from about 14:00 hours to about 18:00 hours (e.g. from about 15:00 hours to about 17:00, such as at about 16:00 hours) is less than about 350 µM (such as less than about 300 µM, for example less than about 250 µM or, more particularly, less than 200 µM, such as less than about 150 µM or less than about 100 µM).

In a more particular embodiment of the first to seventh aspects of the invention, administration of the compounds of the invention is such that the plasma concentration of valproic acid, or a salt and/or metabolite thereof, during the period from about 15:00 hours to about 17:00 hours (such as at about 15:30 hours or about 16:30 hours) is less than about 300 µM (such as less than about 200 µM (e.g. less than about 150 µM, or less than about 100 µM).

Further, the skilled person will be able to adjust both the timing and dose of administration of compounds of the invention in order to meet the requirements of the timing of the Cmax and/or the presence of a maximum or minimum concentration in plasma at a specified time.

As used herein, the terms "therapeutically effective amount" and "therapeutically effective dose" refer to an amount of the active agent (i.e. the compounds of the invention) which confers the required pharmacological or therapeutic effect on the patient, preferably without undue adverse side effects. It is understood that the therapeutically effective amount may vary from patient to patient.

In particular, a therapeutically effective dose of a compound according to the present invention is an amount sufficient to treat or prevent the relevant pathological condition and its complications, particularly where selected to minimise side effects (i.e. adverse events brought about by the action of the therapeutic agent). In view of the disclosures herein, the skilled person will be able to adjust the dose of compounds of the invention administered in order to achieve the desired biological effect using techniques known to those skilled in the art.

The skilled person will understand that the dose of the compounds of the invention may be titrated such that a dose is determined that will achieve a reduction in PAI-1 plasma levels of at least about 20% (such as at least about 30%).

In particular embodiments of the invention (for example, particular embodiments of the first to seventh aspects of the invention), the dose of the compounds of the invention is sufficient to achieve a reduction in PAI-1 plasma levels of at least about 20% (such as at least about 30%), i.e. the dose is titrated to achieve the required reduction in plasma levels of PAI-1.

In more particular embodiments of the invention (for example, particular embodiments of the first to seventh aspects of the invention), the dose is sufficient to achieve a reduction in PAI-1 plasma levels of at least about 40% (such as at least about 50%, e.g. at least about 60%).

Similar dose titrations are known in the art and both starting dose, increments and intervals for PAI-1 measurements (generally from morning samples), desired reduction in PAI-1 and potential dose increments may be chosen by the person skilled in the art.

In certain embodiments, the starting doses for such dose titrations may be in the range of e.g. 50, 60, 70, 80, 90 100, 110, 120, 130, 135, 140 150, 160, 180, 190, 195, 200, 220, 240, 250, 260, 270, 280, 300, 350 or 400 mg and dose increments may be 20-180 mg (e.g. about 40, 60, 65, 70, 80, 120, 140 and 160 mg) every 7-28 days following a new PAI-1 measurement. For example, in one such embodiment the starting dose for a dose titration is 50 mg and the dose is raised in increments of 50 mg every 7 days until a 20% reduction in circulating PAI-1 levels is achieved (i.e. the patient displays a reduction in circulating PAI-1 levels of at least 20%). In another such embodiment, the starting dose for a dose titration is 100 mg and the dose is raised in increments of 100 mg every 14 days until a 20% reduction in circulating PAI-1 levels is achieved.

In one particular embodiment, the starting dose for a dose titration is about 55-95 mg (e.g. about 55, 60, 65, 70, 75, 80, 85, 90 or 95 mg) and the dose is raised in increments of about 55-95 mg (e.g. about 55, 60, 65, 70, 75, 80, 85, 90 or 95 mg) every 7 days to 8 weeks (e.g. 7-28 days or 2-8 weeks) until a 20% reduction in circulating PAI-1 levels is achieved. In another such embodiment, the starting dose for a dose titration is about 60-80 mg and the dose is raised in increments of 60-80 mg every 7 days to 8 weeks until a 20% reduction in circulating PAI-1 levels is achieved.

In another particular embodiment, the starting dose for a dose titration is about 110 to 190 mg (e.g. about 110, 120, 130, 140, 150, 160, 170, 180 or 190 mg) and the dose is raised in increments of about 55-95 mg (e.g. about 55, 60, 65, 70, 75, 80, 85, 90 or 95 mg) every 7 days to 8 weeks (e.g. 7-28 days or 2-8 weeks) until a 20% reduction in circulating PAI-1 levels is achieved. In another such embodiment, the starting dose for a dose titration is about 120-160 mg and the dose is raised in increments of about 60-80 mg (e.g. about 60, 65, 70, 75 and 80 mg) every 7 days to 8 weeks (e.g. 7-28 days or 2-8 weeks) until a 20% reduction in circulating PAI-1 levels is achieved.

In another particular embodiment, the starting dose for a dose titration is about 110 to 190 mg (e.g. about 110, 120, 130, 140, 150, 160, 170, 180 or 190 mg) and the dose is raised in increments of about 110 to 190 mg (e.g. about 110, 120, 130, 140, 150, 160, 170, 180 or 190 mg) every 7 days to 8 weeks (e.g. 7-28 days or 2-8 weeks) until a 20% reduction in circulating PAI-1 levels is achieved. In another such embodiment, the starting dose for a dose titration is about 120-160 mg (e.g. about 120, 130, 140, 150 or 160 mg) and the dose is raised in increments of about 120-160 mg (e.g. about 120, 130, 140, 150 or 160 mg) every 7 days to 8 weeks (e.g. 7-28 days or 2-8 weeks) until a 20% reduction in circulating PAI-1 levels is achieved.

In another particular embodiment, the starting dose for a dose titration is about 210 to about 290 mg (e.g. about 210, 220, 230, 240, 250, 260, 270, 280 or 290 mg) and the dose is raised in increments of about 110 to 190 mg (e.g. about 110, 120, 130, 140, 150, 160, 170, 180 or 190 mg) every 7 days to 8 weeks (e.g. 7-28 days or 2-8 weeks) until a 20% reduction in circulating PAI-1 levels is achieved. In another such embodiment, the starting dose for a dose titration is about 230-280 mg (e.g. about 230, 240, 250, 260, 270 or 280 mg) and the dose is raised in increments of about 115-140 mg (e.g. about 115, 120,130 or 140 mg) every 7 days to 8 weeks (e.g. 7-28 days or 2-8 weeks) until a 20% reduction in circulating PAI-1 levels is achieved. In another particular embodiment, the starting dose for a dose titration is about 210 to about 290 mg (e.g. about 210, 220, 230, 240, 250, 260, 270, 280 or 290 mg) and the dose is raised in increments of about 210 to 290 mg (e.g. about 210, 220, 230, 240, 250, 260, 270, 280 or 290 mg) every 7 days to 8 weeks (e.g. 7-28 days or 2-8 weeks) until a 20% reduction in circulating PAI-1 levels is achieved. In another such embodiment, the starting dose for a dose titration is about 230-280 mg (e.g. about 230, 240, 250, 260, 270 or 280 mg) and the dose is raised in increments of about 230-280 mg (e.g. about 230, 240, 250, 260, 270 or 280 mg) every 7 days to 8 weeks (e.g. 7-28 days or 2-8 weeks) until a 20% reduction in circulating PAI-1 levels is achieved.

In alternative such embodiments, references to achieving a 20% reduction in circulating PAI-1 levels may be replaced with references to achieving a 30% reduction in circulating PAI-1 levels.

In further alternative such embodiments, references to achieving a 20% reduction in circulating PAI-1 levels may be replaced with references to achieving a 40% reduction in circulating PAI-1 levels.

Similarly, the skilled person will understand that if the increase of dose in such titrations, or the dose first administered, results in unwanted effects (such as an unacceptable level of adverse events) and/or results in a greater than required therapeutic effect, the dose may be decreased in increments, such as those described herein for the increase of doses in dose titration experiments, until acceptable levels (i.e. of adverse events and/or therapeutic effect) are obtained.

Without wishing to be bound by theory, it is thought that the surprising effects resulting from the administration of compounds of the invention as described herein can be obtained through administration of doses that are at a level that is not expected to result in significant levels of adverse events.

Thus, in particular embodiments of the first to seventh aspects of the invention, the treatment may require administering a dose (i.e. a therapeutically effective dose) of VPA or a pharmaceutically acceptable salt thereof (e.g. one such dose in a 24 hour period) that is selected in order to minimise the level of adverse events resulting from such treatment (e.g. is of a sufficiently low level to avoid the occurrence of such adverse events).

In particular embodiments of the first to seventh aspects of the invention, the treatment may require administering a dose of VPA or a pharmaceutically acceptable salt thereof (e.g. one or two such doses in a 24 hour period, such as one such dose in a 24 hour period) that is selected in order to minimise the level of adverse events resulting from such treatment (e.g. is of a sufficiently low level to avoid the occurrence of such adverse events).

Such amounts may vary according to the frequency and mode of administration, the sex, age, weight and general condition of the subject treated, the nature and severity of the condition treated and or other treatments used by the individual, and may be determined by conventional techniques in the field. The amount that is effective for a particular therapeutic purpose will depend on the severity of the condition as well as on the weight and general state of the subject. It will be understood that determination of an appropriate dosage may be achieved, using routine experimentation, by constructing a matrix of values and testing different points in the matrix, all of which is within the ordinary skills of a person skilled in the art.

Notwithstanding the discussion of specific doses as provided herein, the skilled person will understand that the amounts of and dosage regimes of compounds of the invention required for treating or preventing a pathological condition associated with excess fibrin deposition and/or thrombus formation as described herein may be determined using the routine skill of the prescribing physician.

In particular embodiments of the first to seventh aspects of the invention, VPA or pharmaceutically acceptable salt thereof may be administered as a single dose per 24 hour period (i.e. a single daily dose).

For example, in particular embodiments of the first to seventh aspects of the invention, VPA, or a pharmaceutically acceptable salt thereof, may be administered:
(i) as a single dose per 24 hour period (i.e. a single daily dose); and/or
(ii) at a total dose per 24 hour period (i.e. a total daily dose) of about 50 mg to about 1200 mg (particularly about 50 mg to about 1000 mg, such as about 100 mg to about 800 mg, such as about 200 mg to about 600 mg, such as about 300 mg to about 500 mg, such as about 240 mg to about 560 mg, such as about 260 mg to about 520 mg).

More particularly, the single daily doses as described above (e.g. at point (i) directly above) may be administered at a time from about 20:00 hours to about 06:00 hours.

In a more particular embodiment, the single daily dose (e.g. described at point (i) above) may be administered at a time from about 21:00 hours to about 05:00 hours (e.g. about 22:00 hours to about 04:00 hours, such as about 22:00 to about 00.00 hours).

In a yet more particular embodiments (particularly wherein the treatment is administered as a pharmaceutical composition that is not formulated for delayed release of the active ingredient), the single daily dose (e.g. described at point (i) above) may be administered at a time from about 02:00 hours to about 06:00 hours (e.g. about 03:00 hours to about 05:00 hours, such as about 04:00 hours).

In further particular embodiments (particularly wherein the treatment is administered as a pharmaceutical composition that is formulated for delayed release of the active ingredient, such as those described in the eight aspect of the invention herein), the single daily dose (e.g. as described at point (i) above) may be administered at a time from about 20:00 hours to about 00:00 hours (e.g. about 21:00 hours to about 23:00 hours, such as at about 22:00 hours). In an alternative such embodiment, the time period is from about 18:00 hours to about 22:00 hours.

In alternative embodiments (particularly wherein the treatment is administered as a pharmaceutical composition that is formulated for delayed release of the active ingredient, such as those described in the eight aspect of the invention herein), the single daily dose (e.g. as described at point (i) above) may be administered prior to sleep (i.e. immediately before the patient begins to attempt to sleep, which may alternatively be described as "before bed", "before sleep", or the like).

In further alternative embodiments (particularly wherein the treatment is administered as a pharmaceutical composition that is formulated for delayed release of the active ingredient, such as those described in the eight aspect of the invention herein), the single daily dose (e.g. as described at point (i) above) may be administered with (i.e. about the same time as) an evening meal (e.g. with dinner, or the like).

In particular embodiments of the invention (for example, particular embodiments of the first to seventh aspects of the invention), compounds of the invention may be administered in a manner such that the plasma concentration of VPA, or a salt and/or metabolite thereof, during a particular period (e.g. a 24 hour period) mimics the plasma concentration of PAI-1 during the same period.

As used herein, references to a plasma level that "mimics" another will be understood to mean that the relative plasma levels of the two agents follow substantially similar patterns of variation (e.g. the curves obtained by plotting the plasma concentrations of the two agents may be substantially superimposable, although the absolute levels/concentrations of the two agents may be different). The term "mimics" has its ordinary meaning in the art, i.e. to resemble, simulate, approximate, follow or impersonate, but not necessarily replicate exactly or precisely.

The skilled person will understand that, in addition to the evening dose, a lower morning dose may be administered, which dose would be absorbed when the PAI-1 level starts to increase in the late afternoon. For example, in one such treatment, 10-600 mg, such as 10-500 mg (e.g. 50-300 mg, more particularly 100 or 200 mg) of VPA or a pharmaceutically acceptable salt thereof is administered approximately 10-14 hours (such as e.g. 12 hours) after the evening dose.

Thus, in more particular embodiments of the invention, a lower morning dose is administered, in addition to the evening dose, which dose will consist of about 10 to about 500 mg (such as about 50 to about 300 mg, more particularly about 100, about 200 mg or about 270 mg) that is administered during a time period that is about 10 to about 14 hours (such as e.g. about 12 hours) after the evening dose. In a specific embodiment, this morning dose is about 20 to about 50% (such as about 20, about 30 or about 40%) of the evening dose.

In a more particular embodiment, there is provided a once-daily formulation of VPA or a pharmaceutically acceptable salt thereof that provides the same effect as the morning and evening dose described in the embodiment directly above, which may be provided in the form of a dual layer formulation with a core giving a second small peak coinciding with the rise in PAI-1, or with differently coated and/or formulated microparticulates (e.g. granules) formulated for such a release profile.

As described herein, it has been found that VPA may potently reduce plasma PAI-1 levels, with such reduction allowing for an increase in the activity of endogenous t-PA. In particular, administration of VPA such that plasma levels thereof coincide with peak plasma levels of PAI-1 may allow for the treatment or prevention of pathological conditions associated with excess fibrin deposition and/or thrombus formation.

Thus, references herein (e.g. in the first to seventh aspects of the invention) to uses in treating or preventing a pathological condition associated with excess fibrin deposition and/or thrombus formation may also refer to treating or preventing a pathological condition expected to benefit from (i.e. be treated or prevented by) reduced activity of PAI-1.

For the avoidance of doubt, specific conditions referred to as being associated with excess fibrin deposition and/or thrombus formation, as known to the skilled person (in particular, as described herein), may also be understood to be expected to benefit from (i.e. be treated or prevented by) reduced PAI-1 activity, which may be understood to result from reduced levels of PAI-1 in plasma.

In particular, in a further aspect of the invention, there is provided a method of reducing PAI-1 levels (i.e. levels of PAI-1 in plasma) in a patient in need thereof comprising the step of administering a therapeutically effective amount of VPA, or a pharmaceutically acceptable salt thereof (as described herein).

Similarly, specific methods of treating or preventing conditions associated with excess fibrin deposition and/or thrombus formation as referred to herein may also be understood as being methods of reducing PAI-1 levels in a patient in need thereof.

For example, in a yet further alternative first aspect of the invention, there is provided a method of reducing PAI-1 levels in a patient in need thereof comprising administering at least one dose of a therapeutically effective amount of VPA, or a pharmaceutically acceptable salt thereof (as described herein), to a patient such that the maximum plasma concentration (Cmax) of VPA, or a salt and/or metabolite thereof, in the patient occurs during a time period that is from four hours before to one hour after the maximum plasma concentration (Cmax) of PAI-1 in the patient.

As used herein, references to reducing levels of PAI-1 (and, similarly, to reduced (or inhibited) PAI-1 activity, e.g. references to inhibiting PAI-1) may refer to levels of PAI-1 in plasma during treatment with compounds of the invention being at (e.g. reduced to or maintained at) levels lower than (e.g. at least 10% lower than, such as at least 20% lower than, for example at least 30%, at least 40%, at least 50% or at least 60%) levels of PAI-1 occurring prior to treatment with compounds of the invention (i.e. VPA).

Compounds of the Invention

Again, as indicated herein, the term "compounds of the invention" refers to VPA and pharmaceutically acceptable salts thereof, including mixtures thereof (such mixtures with or of pharmaceutically acceptable salts thereof). The skilled person will understand that valproic acid may also be referred to as, inter alia, 2-propylpentanoic acid and VPA.

The compounds presented herein include, where relevant, all diastereomeric, enantiomeric, and epimeric forms. For compounds described herein that exist as tautomers, all tautomers are included within the formulas described herein. Further, the compounds described herein may be formed as, and/or used as, salts (e.g. pharmaceutically acceptable salts). The skilled person will understand that references herein to salts of compounds will include references to pharmaceutically acceptable salts.

Compounds described herein may be prepared using techniques and procedures known to those skilled in the art. Exemplary synthetic methods useful for synthesizing the compounds in the application include, for example, those disclosed in Nogrady (1985) Medicinal Chemistry A Biochemical Approach, Oxford University Press, New York, pages 388-392; Silverman (1992); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989).

Compounds of the invention as described herein may be commercially available and/or may be synthesized in accordance with published procedures, as known to the skilled person and/or as mentioned herein.

In particular, VPA may be commercially available, for example from Sigma-Aldrich (under product number P4543 as at 1 Oct. 2014). Pharmaceutically acceptable salts of VPA (such as sodium salt thereof) may also be commercially available. It will also be appreciated that VPA, or pharmaceutically acceptable salts thereof, may be synthesised using techniques well known to those skilled in the art.

As described herein, VPA may be formulated and/or administered in the form of a pharmaceutically acceptable salt thereof.

Pharmaceutically acceptable salts (and salts in general) that may be mentioned include but are not limited to:
(a) salts formed when an acidic proton is replaced by a metal ion, such as for example, an alkali metal ion (e.g. lithium, sodium, potassium), an alkaline earth ion (e.g. magnesium, or calcium), or an aluminium ion, or is replaced by an ammonium cation ($NH_4^+$);
(b) salts formed by reacting compounds with a pharmaceutically acceptable organic base, which includes alkylamines, such as ethanolamine, diethanolamine, triethanolamine, tromethamine, N-methylglucamine, dicyclohexylamine, tris(hydroxymethyl)methylamine, and salts with amino acids such as arginine, lysine, and the like;
(c) salts formed by reacting compounds with a pharmaceutically acceptable acid, which provides acid addition salts. Pharmaceutically acceptable acids include hydrochloric acid, hydrobromic acid, sulfuric acid, nitric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Additional pharmaceutically acceptable salts that may be mentioned include those described in Berge et al., J. Pharm. Sci. 1977, 66, 1-19; and "Handbook of Pharmaceutical Salts, Properties, and Use", Stah and Wermuth, Ed.; Wiley-VCH and VHCA, Zurich, 2002 (the contents of which are incorporated herein in their entirety).

Particular pharmaceutically acceptable salts of VPA that may be mentioned include those mentioned at point (a) above. More particular pharmaceutically acceptable salts that may be mentioned include those where the carboxylic acid proton is replaced with an alkaline earth ion (e.g. magnesium or calcium) or, more particularly, an alkali metal ion (e.g. lithium, sodium or potassium).

In particular embodiments of each aspect of the invention, the VPA is administered and/or formulated (as appropriate) in the form of the sodium salt thereof (i.e. sodium valproate). In more particular embodiments, the VPA is administered and/or formulated (as appropriate) in the form of a mixture of VPA (i.e. in the non-salt form) and the sodium salt thereof (i.e. sodium valproate), such as an equal mixture thereof.

For instance, in particular embodiments of the invention (i.e. embodiments of each aspect of the invention), the compound of the invention is VPA, wherein the VPA is administered and/or formulated (as appropriate) in the form of a mixture of the sodium salt thereof (i.e. sodium valproate) and valproic acid. Several such mixtures are known in the art, such as: valproate semisodium, also known as divalproex sodium (1:1 molar relationship between valproic acid and sodium valproate), which is marketed, for example, as Depakote and Depakote ER (by AbbVie Inc.); and valproate sodium (1:2.3 ratio between valproic acid and sodium valproate), which is marketed, for example, as Epilex Chrono. For the avoidance of doubt, in particular embodiments the compound of the invention is sodium valproate.

References to "salts" of compounds of the invention will be understood to refer to salt forms that may occur through exchange of anions or cations with compounds of the invention, for example, in blood plasma. In particular, the term "salts" may also refer to pharmaceutically acceptable salts, such as those described herein.

As described herein, VPA may also be formulated and/or administered in the form of a prodrug thereof, or a pharmaceutically acceptable salt of said prodrug.

As used herein, the term prodrug when used in relation to compounds of the invention will be understood to refer a compound that may be converted to a compound of the invention in vivo (i.e. following administration).

Such prodrugs may be identified by a person skilled in the art and may include ester (e.g. methyl or ethyl ester) or amide derivatives of compounds of the invention. Particular prodrugs of VPA that may be mentioned include 2-propyl-pentanamide (also known as valpromide), and pharmaceutically acceptable salts thereof.

When compounds of the invention are administered in the form of a prodrug thereof, the skilled person will be able to adjust the dose administered in order to achieve the equivalent dose of the compounds of the invention as required.

Commercially-available products containing valproic acid and/or sodium valproate, or prodrugs thereof, include but are not limited to:

Depakote (AbbVie Inc.), Absenor (Orion Corporation), Convulex (Pfizer), Convulex CR, Depakene/Depakine/Depalept/Deprakine (AbbVie Inc./Sanofi Aventis), Depakine Chrono (Sanofi), Depakene-R (Kyowa Hakko Kogyo), Selenica-R (Kowa), Encorate (Sun Pharmaceuticals India), Encorate Chrono (Sun Pharmaceuticals), Epival (Abbott Laboratories), Epilim (Sanofi), Epilim Chronospheres modified release granules, Epilim Chrono Controlled release tablets, Epilim Chrono Prolonged release tablets, Stavzor (Noven Pharmaceuticals), Valcote (Abbott Laboratories), Valpakine (Sanofi Aventis), Depamide (Sanofi-Avetis), Dipexil-R (Bial), Eliaxim (Bial), Sodium Valproate Sandoz Tablets (Sanofi), Valpro Tablets (Alphapharm), Valproate Winthrop Tablets (Sanofi), Valprease (Sigma), Epilim EC modified release tablets (Sanofi-Aventis), Oriept (Wockhardt), Epilim Chrono (Sanofi) (1:2.3 ratio of valproic acid and sodium valproate), Epilim EC200 (Sanofi), Valprol CR (Intas Pharmaceutical), Episenta prolonged release (Beacon), Valproic Acid capsules, USP (Teva), Stavzor (Noven), Orfiril (Desitin Pharmaceuticals).

Commercially-available products containing valproic acid and/or sodium valproate, or prodrugs thereof, will also include generic version of the above-mentioned formulations, which may be sold/marketed under a different name.

Administration of the Compounds

The skilled person will understand that there is also provided a pharmaceutical composition comprising the VPA, or a pharmaceutically acceptable salt thereof, and optionally comprising one or more pharmaceutically acceptable excipient, for use in (or use in a method of) treating or preventing a pathological condition associated with excess fibrin deposition and/or thrombus formation as described in first to seventh aspects of the invention (including all embodiments thereof).

Compounds of the invention may be administered to a subject in a convenient manner such as by the oral, intravenous, intramuscular, subcutaneous, intraperitoneal, intranasal, buccal, transdermal, intradermal, or suppository routes as is known in the art. In particular, compounds of the invention may be administered by the oral route; for example, as a pharmaceutical formulation suitable for oral administration (e.g. a tablet, capsule, buccal film, spray or the like).

In particular, pharmaceutical formulations suitable for oral administration may be presented as discrete units, such as capsules or tablets (e.g. tablets or multiparticulates such as minitablets or granules), which each contain a predetermined amount of the active ingredient, and which may include one or more suitable excipients. Furthermore, the orally available formulations may be in the form of a powder, or multiparticulates, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavouring agents, colouring agents and preserving agents in order to provide pharmaceutically elegant and palatable preparations.

As used herein, the term multiparticulates will refer to small discrete units, such as granules, beads, microspheres, microparticles, pellets, spheroids and minitablets. A number of multiparticulates may be combined into a final dosage form. The multiparticulates may each be uncoated or coated units. In particular embodiments, at each instance herein, the term multiparticulates may refer to granules, pellets and/or minitablets.

In particular embodiments, the pharmaceutical composition may be provided in the form of minitablets, pellets or granules (e.g. minitablets or granules), which minitablets, pellets or granules may be coated (e.g. with a delayed release coating) as described herein. Such minitablets, pellets or granules (particularly, minitablets or granules) may be administered as discrete units (i.e. a plurality of separate units that together constitute a single dose) or as comprised within a suitable housing, such as a capsule (e.g. a hard capsule, such as a hard gelatin capsule).

For the avoidance of doubt, where the composition is administered in the form of a capsule containing multiparticulates (e.g. minitablets, pellets or granules, particularly, minitablets or granules), suitable coatings as described herein may be applied to the individual minitablets, pellets or granules.

For the avoidance of doubt, multiparticulates (particularly minitablets, pellets or granules) as described herein may be individually treated in the same manner as is described for tablets, and may be referred to as such.

For example, tablets or multiparticulates may contain the active ingredient(s) in admixture with non-toxic pharmaceutically acceptable excipients which are suitable for the manufacture of the intended dosage form (e.g. tablets or multiparticulates). These excipients may, for example, be: diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets or multiparticulates may be uncoated (with or without release-modifying agents in the tablet) or they may be coated by known techniques to delay disintegration and absorption in the gastrointestinal tract and thereby provide a sustained action over a longer period. In one embodiment, a time delay material such as glyceryl monostearate or glyceryl distearate may be employed. In another embodiment, the tablets or multiparticulates may also be coated by the techniques described in U.S. Pat. Nos. 4,356,108; 4,166,452; and 4,265,874, the contents of which are incorporated herein by reference, to form osmotic therapeutic tablets for controlled release.

Moreover, formulations for oral use may also be presented as hard capsules (e.g. made from gelatine or HPMC) where the active ingredient is mixed with a solid diluent, for example, calcium carbonate, lactose, calcium phosphate or kaolin, or a soft gelatine capsules wherein the active ingredient is mixed with a liquid or semi-solid medium (such as a water miscible liquid e.g. poly ethylene glycol) or an oil medium, for example peanut oil, liquid paraffin, or olive oil. Such hard capsules (e.g. gelatine capsules) may be formulated to contain multiparticulates (such as granules, pellets or minitablets) of the active ingredient, which multiparticulates may be formulated (e.g. coated) in a manner as described herein for tablets.

Further, formulations for oral use may be presented into the form of tablets composed of compressed multiparticulates (e.g. a compressed plurality of discrete granules), which multiparticulates may be individually coated.

Thus, in embodiments wherein the formulation comprises multiparticulates (e.g. in a capsule or tablet, such as a tablet composed of compressed multiparticulates (i.e. a pluarity of particles) or capsules containing multiparticulates such as granules, pellets or mini tablets), such multiparticulates may have different coatings (or formulated for delayed release using polymers as described below), which coatings/formulations may be selected to regulate the release of compounds of the invention; for example, in order to control absorption and render a plasma profile mimicking the PAI-1 plasma profile. The use of such coatings/formulations to control absorption/release of certain drugs is known in the art and can e.g. be based on different polymers e.g. based on acrylic acid or cellulose (including derivatives thereof) and is described more extensively below.

In one embodiment, mini tablets are defined as flat or curved tablets with a 1.0-3.0 mm diameter. As described herein, such minitablets may be administered as a plurality of discrete units or may be provided in a suitable housing, e.g. filled in hard capsules (such as hard gelatin capsules).

Without wishing to be bound by theory, it is thought that multiple unit dosage forms such as e.g. mini tablets, granules or pellets are less dependent on the degree of filling of the stomach and may therefore lead to lower variability in e.g. absorption profiles in different patients.

The single multiparticulates of multiple unit dosage forms can be prepared by commonly known methods including granulation, pelletizing, extrusion, hot melt extrusion, tableting and/or coating techniques. For examples on the production of tablets and/or capsules from coated granules/microtablets see e.g. WO 96/01621, WO 96/01624, Siddique, Khanam and Bigoniya, AAPS PharmSciTech 2010. These references also provide information on how different materials can be used to control the release of drug from a tablet or capsule (or from granules in said tablet or capsule).

In particular, the skilled person will be aware that valproic acid is a liquid and sodium valproate is a hygroscopic powder. Suitable excipients and preparation processes for these types of ingredients are known in the art and include e.g. silica gels as liquid carrier and coating of components with a suitable polymer (e.g. methacrylic acid copolymers of different types) and/or water insoluble materials such as waxes/fatty acids etc., in order to achieve reduced hygroscopicity. Such polymers may also be used to delay the release and/or absorption of the drug according to the invention.

For buccal and sublingual use, tablets, patches, creams, ointments, jellies, solutions of suspensions and the like containing the compounds of the invention may be employed.

Pharmaceutical compositions may also be in the form of suppositories, rectal capsules, rectal solutions, emulsions and suspensions, rectal foams and rectal tampons for rectal administration of the compounds of the invention. These suppositories can be prepared by mixing the compounds of the invention with a suitable non-irritating excipient which is solid at ordinary temperatures but liquid at the rectal temperature and will thus melt in the rectum to release the drug. Such materials include, for example, cocoa butter and polyethylene glycols.

Pharmaceutical compositions comprising compounds of the invention may also be provided in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Pharmaceutical forms suitable for injectable use include, but is not limited to, sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, sterile water, ethanol, polyol (for example, glycerol, propylene glycol and liquid polyethylene glycol and the like), suitable mixtures thereof, and vegetable oils. The proper fluidity can be maintained, for example, by the use of a coating such as lecithin, by the maintenance of the required particle size in the case of a dispersion, and by the use of surfactants. The preventions of the action of microorganisms can be brought about by various antibacterial and antifungal agents; for example, parabens, chlorobutanol, phenol, sorbic acid, thiomersal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate, and gelatin.

Sterile injectable solutions are prepared by incorporating the active material in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique, which yield a powder of the active ingredient plus any additional desired ingredient from previously sterile-filtered solution thereof.

In particular, it has been found that compounds of the invention may be conveniently administered to a subject by the oral route, particularly in the form of a tablet or capsule (e.g. a tablet). Moreover, we have found that the particular dosage regimes contemplated in the invention are particularly suited to oral administration in the form of a tablet or capsule (or multiparticulates in said tablet or capsule) that is formulated such the release of compounds of the invention from said tablet or capsule (or multiparticulates in said tablet or capsule) after oral administration is delayed.

As used herein, references to formulations allowing for delayed or controlled released will be understood by those skilled in the art. In this regard, it will be understood that the terms delayed and controlled may be used interchangeably.

In an eighth aspect of the invention, there is provided a pharmaceutical composition comprising VPA, or a pharmaceutically acceptable salt thereof, wherein the composition is in the form of a tablet or capsule for oral administration and is formulated such that substantially all of the VPA, or a pharmaceutically acceptable salt thereof, is released during a period from about four to about eight hours (e.g. about four to about seven hours) after administration.

As used herein, references to a capsule will include capsules filled with the active ingredient in powder form or, particularly, in the form of multiparticulates (e.g. granules, pellets and/or minitablets), which multiparticulates may be coated as described herein, and which capsule may itself be coated. Furthermore, the multiparticulates may be formulated for specific release profiles using e.g. different delayed/controlled release polymers (and/or coating the microparticulates, such as granules or minitablets).

As used herein, references to a tablet will include minitablets, and tablets formed from compressed multiparticulates (such as granules, pellets and/or microparticles), which microparticulates may be coated as described herein, and which tablets may also be coated.

As used herein (particularly in reference to the eight aspect of the invention, including all embodiments thereof), the term "substantially all" will refer to an amount that is at least 60% of the total amount present (i.e. the total amount included in the composition). In particular, the term may refer to an amount that is at least 70% of the total, such as at least 80% of the total. More particularly, the term may refer to an amount that is at least 90% of the total, such as at least 95% (e.g. at least 99%) of the total.

In a particular embodiment of the eighth aspect of the invention, references to substantially all of the VPA, or a pharmaceutically acceptable salt thereof, being released may refer to substantially all of one dose (i.e. at least one therapeutically effective dose) thereof.

The skilled person will understand that the release of the active ingredient may be delayed if the composition is administered with or shortly after food. Thus, references to the time taken for the active ingredient to be released may refer to the time taken for such release when the composition is administered to a patient at least two hours after that patient has consumed food (which may be referred to as administration on an empty stomach, or the like).

It may also be appreciated that it may be beneficial to administer compounds of the invention with food (e.g. to reduce gastrointestinal side-effects). Thus, in a particular embodiment of the first to seventh aspects of the invention, the treatment comprises administering VPA, or a pharmaceutically acceptable salt thereof, with food (e.g. administered to a patient who has consumed food less than two hours prior to administration or who will be directed to consume food within 30 minutes of administration).

As used herein (particularly in reference to the eight aspect of the invention, including all embodiments thereof), references to an active ingredient being "released" (i.e. from a pharmaceutical formulation) will refer to the active ingredient being in a form that is (or would be) available for absorption (i.e. when administered orally, systemic absorption from the gastro intestinal (GI) tract), such as in a form that is dispersed or dissolved in surrounding media. When used in relation to tablets and/or capsules for oral administration, the term will indicate that the active ingredient is not contained in said tablet or capsule (which may include the active ingredient being no longer contained within multiparticulates (e.g. coated granules, pellets or minitablets) contained within said tablets or capsules but is instead distributed in the GI tract.

In a particular embodiment of the eighth aspect of the invention, the pharmaceutical composition is formulated such that substantially all of the VPA, or a pharmaceutically acceptable salt thereof, is released during a period from about six to about eight hours after administration (such as about six to about seven hours after administration, or such as about seven to about eight hours after administration, e.g. about seven hours after administration).

In more particular (and alternative) embodiments of the eighth aspect of the invention, the pharmaceutical composition is formulated such that substantially all of VPA, or a pharmaceutically acceptable salt thereof, is released during a period that is:
 (i) from about three to about five hours after administration (from about four to about five hours after administration);
 (ii) from about four to about six hours after administration;
 (iii) from about five to about seven hours after administration;
 (iv) from about six to about eight hours after administration;
 (v) from about seven to about nine hours after administration;
 (vi) from about eight to about ten hours after administration (e.g. from about eight to about nine hours after administration);
 (vii) from about nine to about eleven hours after administration;
 (viii) from about ten to about twelve hours after administration;
 (ix) from about eleven to about thirteen hours after administration;
 (x) from about twelve to about fourteen hours after administration.

In yet more particular (and alternative) embodiments of the eighth aspect of the invention, the pharmaceutical composition is formulated such that substantially all of the VPA, or a pharmaceutically acceptable salt thereof, is released during a period that is from about four to about six hours after administration.

In another particular (and alternative) embodiment of the eighth aspect of the invention, the pharmaceutical composition is formulated such that substantially all of the VPA, or a pharmaceutically acceptable salt thereof, is released during a period that is from about five to about seven hours after administration.

In another particular (and alternative) embodiment of the eighth aspect of the invention, the pharmaceutical composition is formulated such that substantially all of the VPA, or a pharmaceutically acceptable salt thereof, is released during a period that is from about six to about eight hours after administration.

In another particular (and alternative) embodiment of the eighth aspect of the invention, the pharmaceutical composition is formulated such that substantially all of the VPA, or a pharmaceutically acceptable salt thereof, is released during a period that is from about seven to about ten hours after administration.

In yet another particular (and alternative) embodiment of the eighth aspect of the invention, the pharmaceutical composition is formulated such that substantially all of the VPA, or a pharmaceutically acceptable salt thereof, is released during a period that is from about seven to about nine hours (e.g. about 8 to about 9 hours) after administration.

In another particular (and alternative) embodiment of the eighth aspect of the invention, the pharmaceutical composition is formulated such that substantially all of the VPA, or a pharmaceutically acceptable salt thereof, is released during a period that is from about eight to about ten hours after administration.

In particular embodiments, the pharmaceutical composition may be formulated such that substantially none (e.g.

less than 10%, such as less than 5%, e.g. less than 3%, 2% or 1%) of the VPA, or a pharmaceutically acceptable salt thereof, is released prior to the relevant release window as specified (e.g. prior to about four hours after administration).

As described herein, the release profile of the active ingredient (i.e. VPA, or pharmaceutically acceptable salt thereof) may be characterized by delayed release followed by rapid release (i.e. a rate of release as may be expected in an immediate release formulation), rather than the prolonged, gradual release that may be provided by an extended release formulation.

Thus, in further embodiments, the pharmaceutical composition may be formulated such that the release profile of the active ingredient (i.e. VPA, or pharmaceutically acceptable salt thereof) mimics the example release profile as shown in FIG. 3 herein.

The skilled person will understand that the release profile of pharmaceutical formulations as described herein may be determined using techniques that are well known in the relevant field, such as through the use of standard in vitro models.

For example, determination of the in vitro release profile may be performed by using the USP dissolution apparatus 2 (paddle) as described in Ph. Eur. 2.9.3, wherein standardized conditions such as temperature 37.0±0.5° C. and paddle speed 75 rpm may be used. In perfoming such analyses, acid stage (pH 1, e.g. for 2 hours) with conventional solutions and/or buffer stage (e.g. pH 6.8 or pH 7.0) with conventional buffer solutions may be used; sodium dodecyl sulfate may be included or excluded. Further, an extended in vitro release model by raising pH at multiple occasions may be used. Such a model may include pH 1, 6.4, 6.8 and 7.3 to mimic parts of the gastrointestinal tracts, specifically the stomach and small intestine (see, for example, Fallingborg et al, pH-profile and regional transit times of the normal gut measured by a radiotelemetry device, Aliment Pharmacol Ther. 1989 Dec.;3(6):605-13). In particular, the skilled person will be able to alter the pH of the media utilized in such dissolution tests in order to mimic the pH encountered by an orally administered tablet during GI transit (i.e. in the stomach and intestines) in order to determine the appropriate release profile (e.g. in the case of an enterically coated tablet so administered). Alternatively, the skilled person may begin the dissolution analysis at a pH designed to mimic the pH at the point at which dissolution is expected to begin (e.g. if dissolution is expected to begin when the formulation reaches an environment having pH 7.0, the experiment may begin with that pH).

For the avoidance of doubt, the skilled person will understand that, in the case of tablets, multiparticulates (e.g. granules, pellets or minitablets) or capsules (i.e. capsules comprising solid dosage units, such as granules or pellets) having one or more coatings, the delay between oral administration of a tablet and release of substantially all of the VPA, or a pharmaceutically acceptable salt thereof, may be a combination of the delay caused by the time taken for removal (e.g. by dissolution) of the one or more coatings and the time taken for release from the, then uncoated (i.e. naked), tablet core. For example, in the case of a tablet having an enteric coating, optionally with one or more additional coating, the delay may have as a component thereof the time taken for transit of the tablet through the stomach and then for subsequent dissolution of the coating(s) to expose the naked tablet core, together with the component resulting from the time taken for release of substantially all of the VPA, or a pharmaceutically acceptable salt thereof, from that tablet core.

For example, formulations such as those described in the examples as provided herein may, when tested in such in vitro dissolution assays (starting at pH 7), show the following dissolution times (for release of substantially all (e.g. at least 60%) of the active ingredient):

tablets having a pore forming coating, as described herein: about 2 to about 4 hours, about 4 to about 6 (such as about 6.5 hours), about 6 to about 8 hours (such as about 8.5 hours), particularly about 4 to about 8 hours (or, alternatively, about 3 to about 6 hours, about 3 to about 7 hours, about 4 to about 7 hours);

tablets having an enteric coating only, as described herein: about 1 to about 2 hours, about 1 to about 2.5 hours, about 1 to about 3 hours, about 0.5 to about 1.5 hours, about 0.5 to about 2 hours, about 1.5 to about 2.5 hours, about 1.5 to about 3 hours.

In a particular embodiment of the eighth aspect of the invention, the pharmaceutical composition may further comprise one or more pharmaceutically acceptable excipients (e.g. a pharmaceutically acceptable adjuvant, diluent or carrier), such as those described herein. In such embodiments, the compounds of the invention may be provided in admixture with said one or more pharmaceutically acceptable excipient.

The skilled person will understand that pharmaceutical formulations (i.e. tablets or capsules) comprising compounds of the invention (such as those described in the eight aspect of the invention, including embodiments thereof) will contain all or part of a therapeutically effective dose of the compound(s) of the invention.

For the avoidance of doubt, such a dose may be provided in a single unit of the composition (e.g. a single tablet or capsule), or may be provided by the combined administration of several units of the formulation each comprising a corresponding fraction of the dose (e.g. two tablets each containing half of the required dose, or a plurality of multiparticulates each containing the requisite fraction of the required dose).

In particular, said formulations (e.g. tablets for oral administration) may comprise a single therapeutically effective dose. Thus, in particular embodiments of the eight aspect of the invention, the composition comprises a dose (e.g. a total daily dose) of VPA, or a pharmaceutically acceptable salt thereof, as defined in any one or more of the first to seventh aspects of the invention (including all embodiments thereof).

Depending on the dose required, pharmaceutical formulations that may be mentioned include those in which the active ingredient is present in at least 1% (or at least 10%, at least 30% or at least 50%, or at least 70%, or at least 80%, or at least 90% or at least 95%) by weight. That is, the ratio of active ingredient to the other components (e.g. the pharmaceutically acceptable excipient) of the pharmaceutical composition is at least 1:99 (or at least 10:90, at least 30:70, at least 50:50, at least 70:30, at least 80:20, at least 90:10 or at least 95:5) by weight.

Thus, the skilled person will understand that the invention further provides a process for the preparation of pharmaceutical formulations as described herein (such as those described in the eight aspect of the invention, including embodiments thereof), which process comprises formulating compounds of the invention in a manner as described herein. In particular, such a process may comprise the steps of:

(a) bringing compound(s) of the invention into association with one or more pharmaceutically acceptable excipient (e.g. to form an admixture thereof); and (b) formulating as a tablet or capsule (as described herein).

The skilled person will understand that the term bringing into association means that the relevant components are rendered suitable for administration in conjunction with each other.

As described herein, compounds of the invention may be administered and/or formulated in a form coated by, or administered with, a material to delay release of the active ingredient. In particular, formulations in the form of a tablet may be coated with such a material and/or formulated with polymers that regulate the release. Moreover, formulation in the form of a capsule may be formulated such the capsule is composed of, or comprises an amount (i.e. an effective amount) of, such a material.

In particular embodiments, compositions of the eight aspect of the invention may comprise one or more coatings and/or excipients (e.g. one or more coatings) to delay the release of the active ingredients (i.e. VPA or pharmaceutically acceptable salt thereof).

Thus, pharmaceutical compositions of the eight aspect of the invention may be referred to as "delayed release" or "controlled release" compositions or formulations, or the like.

In such instances, the skilled person will understand that the material to delay release of the active ingredient will be selected and/or formulated in a manner to delay release of the active ingredient for the required time (e.g. for about six or, particularly, for about four hours).

The skilled person will be familiar with materials used to delay (i.e. for delaying) the release of active ingredients, particularly when administered in the form of oral compositions (such as tablets and capsules). Such materials may be described in, for example, Remington's Pharmaceutical Science and U.S. Pharmacopeia (The United States Pharmacopeia—National Formulary (USP—NF)), Remington: The Science and Practice of Pharmacy, 19th Ed. (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, 7th Ed. (Lippincott Williams Wilkins 1999), the contents of which are incorporated herein in their entirety.

For example, materials used to delay the release of active ingredients may include sustained release polymers, such as hydroxypropyl cellulose, hydroxypropyl methylcellulose, carboxymethyl cellulose, chitosan, aloe mucilage, pectin, ethyl cellulose, polyvinyl chloride, polyethylene, polyvinyl alcohol (PVA), acrylic copolymers (such as the polymers known under the tradename Eudragit® and polyvinylpyrrolidone (PVP) (e.g. hydroxypropyl cellulose, hydroxypropyl methylcellulose, carboxymethyl cellulose, chitosan, aloe mucilage, pectin, ethyl cellulose, polyvinyl chloride and polyethylene). Moreover, one way of achieving a sustained release coating is to mix a water soluble polymer such as HPMC with a water insoluble polymer such as ethyl cellulose. The skilled person will understand that different materials used and different ratios thereof will result in different release patterns, and will be able to adjust the formulation accordingly (i.e. to acheive the desired release profile).

The skilled person will understand that where compositions are administered and/or formulated in a form coated by, or administered with, a material to delay release of the active ingredient, said material may be composed of more than one pharmaceutically acceptable substance (e.g. one or more pharmaceutically acceptable coating). For example, where compositions of the eight aspect of the invention are administered in the form of a tablet, said tablet may comprise one or more pharmaceutically acceptable coatings of a material to delay release of the active ingredient.

In such instances, the skilled person will understand that the delay of the release of the active ingredient from the composition (e.g. the tablet) is achieved as a combined effect of these coatings. For example, where a tablet, capsule or multiparticulate (e.g. granule, pellet or minitablet) is coated so as to delay release for a total of six hours after oral administration, it may comprise two layers of coating, each coating delaying release for three hours (or one coating delaying release for two hours and a further coating delaying release for four hours), i.e. with the first coating being removed to expose the second coating, and so on (in other words, said coatings being exposed in a sequential manner).

In particular embodiments of the eight aspect of invention, where compositions of the eight aspect of invention comprise one or more coatings (e.g. are in the form of a coated tablet), one or more of said coatings may be a coating for preventing release of the active ingredient, or preventing exposure of further coatings, in the stomach. In particular, one or more (e.g. one) of said coatings may be an enteric coating. Said enteric coatings will be well known to the person skilled in the art.

In certain embodiments of the eight aspect of invention (particularly those referring to tablets having one or more coating), the core component (e.g. the core component of a coated tablet) may contain one or more components designed to promote disintegration in aqueous media.

Thus, in a particular embodiment of the eight aspect of the invention, the formulation is provided as a tablet (or capsule) for oral administration comprising one or more coated core (e.g. a single coated core, or a plurality of coated multiparticulates (such as mini tablets, pellets or granules) each having such a core), said core(s) containing VPA, or a pharmaceutically acceptable salt thereof, wherein:

(i) said coating is formed of material selected and/or formulated in a manner to delay release of the active ingredient for the required time (e.g. for about six hours); and (ii) said core is formulated to in a manner designed promote disintegration in aqueous media (e.g. comprising one or more disintegrants).

Thus, in particular embodiments, the formulation may be provided in a form (e.g. a tablet or multiparticulates, such as minitablets, granules or pellets) having an inner core containing VPA and/or a pharmaceutically acceptable salt thereof that is coated with an enteric coating layer. In such embodiments, the enteric coating layer may delay the release of the VPA and/or a pharmaceutically acceptable salt thereof until the pH in the GI-tract reaches a pH where the enteric coating dissolves. In such cases, in view of the teachings provided herein, the skilled person will be able to adjust the choice of enteric coating polymers to achive the required release profile.

Thus, in particular embodiments, the formulation may be provided in a form (e.g. a tablet or multiparticulates, such as minitablets, granules or pellets) having an inner core containing VPA and/or a pharmaceutically acceptable salt thereof that is coated with a sustained release coating. In such embodiments, the sustained release coating layer may delay the release of the VPA and/or a pharmaceutically acceptable salt thereof in order to reach the desired release profile. In such cases, the skilled person will be able to adjust the choice of sustained coating polymers to achieve the required release profile.

In further such embodiment, the inner core containing the VPA and/or a pharmaceutically acceptable salt thereof is coated by a mixture of one or more enteric coating polymers and one or more sustained release coating polymers. In such embodiments, the sustained release polymer(s) may delay the dissolution and release of the enteric coating polymer(s) when the pH in the GI-tract reaches a pH where the enteric coating is soluble, thereby further delaying the release of the VPA and/or a pharmaceutically acceptable salt thereof.

In more particular embodiments, the inner core containing the VPA and/or a pharmaceutically acceptable salt thereof is first coated with a sustained release coating and thereafter an enteric coating. In such embodiments, the coatings may delay the release of the VPA and/or a pharmaceutically acceptable salt thereof until the pH in the GI-tract reaches a pH where the enteric coating dissolves and thereafter further sustain the release due to the sustained release coating.

In a yet further embodiment, the core component (i.e. the inner core) may be coated with an enteric film (e.g. of a type and in amount as described herein) and then a sustained release film (e.g. of a type and in amount as described herein).

Suitable disintegrants will be well known to those skilled in the art, including agents designed to swell upon contact with aqueous media.

Similarly, the skilled person will understand that there are several materials that can be used to form an enteric coating on a tablet, capsule and/or multiparticulate unit dosage form. These include but are not limited to shellac, waxes, fatty acids, polymers, plastics and plant fibers.

Examples of such polymers include, but are not limited to, hypromellose phthalate (hydroxypropyl methylcellulose phthalate, HPMCP), hypromellose acetate succinate, cellulose acetate trimellitate, acrylic acid/methacrylic acid copolymers (e.g. poly(methacrylic acid-co-methyl methacrylate), cellulose acetate phthalate (CAT), poly(vinyl acetate phthalate, PVAP) and ethyl acrylate. Other materials for enteric coating include dextrins, amylose starch and starch derivatives, sodium alginate, Zein and Aqua-Zein R.

More particular examples of such polymers include, but are not limited to, hypromellose phthalate (hydroxypropyl methylcellulose phthalate, HPMCP HP-50, HP-55, HP-55S), hypromellose acetate succinate (Aqoat AS-HF/HG, Aqoat AS-LF/LG, Aqoat AS-MF/MG), cellulose acetate trimellitate, enteric polymethacrylates (e.g. poly (methacrylic acid-co-methyl methacrylate), 1:1 (Eudragit® L 100, Eudragit® L 12.5), poly(methacrylic acid-co-ethyl acrylate) 1:1 (Eudragit® L 30 D-55, Eudragit® L 100-55, Acryl-EZE® 93A, Acryl-EZE MP, Kollicoat® MAE 30 DP, Kollicoat® MAE 100 P, Eastacryl 30D,), poly (methacrylic acid-co-methyl methacrylate) 1:2 (Eudragit® S 100, Eudragit® S 12.5), poly(methyl acrylate-co-methyl methacrylate-co-methacrylic acid) 7:3:1 (Eudragit® FS 30 D)), cellulose acetate phthalate (CAP, Aquacoat® CPD), and poly(vinyl acetate phthalate, PVAP, Sureteric®) and ethyl acrylate.

In particular embodiments, the enteric coating polymers are selected from the group of enteric polymethacrylates (e.g. poly(methacrylic acid-co-methyl methacrylate) 1:1 (Eudragit® L 100, Eudragit® L 12.5), poly(methacrylic acid-co-ethyl acrylate) 1:1 (Eudragit® L 30 D-55, Eudragit® L 100-55, Acryl-EZE® 93A, Acryl-EZE MP, Kollicoat® MAE 30 DP, Kollicoat® MAE 100 P, Eastacryl 30D,), poly (methacrylic acid-co-methyl methacrylate) 1:2 (Eudragit® S 100, Eudragit® S 12.5), poly(methyl acrylate-co-methyl methacrylate-co-methacrylic acid) 7:3:1 (Eudragit® FS 30 D)).

Particular enteric coatings that may be mentioned include Eudragit® L 30 D-55 and Eudragit® FS 30 D.

In one embodiment the enteric coating is Eudragit® L 30 D-55 or Eudragit® FS 30 D.

The skilled person will understand that different materials have different properties, such as in relation to the dissolution pH, and can thus be used to control the absorption pattern, such as by delaying release of a drug for a specific time.

Futher information relating to the use of enteric coatings is provided in, for example, Singh Deep Hussan, et al., IOSR Jounal of Pharmacy (2012), and the Handbook of Pharmaceutical Excipients Rowe, Raymond C; Sheskey, Paul J; Cook, Walter G; Fenton, Marian E., Seventh edition, the disclosures of which are incorporated herein by reference in their entirety.

The skilled person will understand that there are several materials that can be used to form a sustained release coating on a tablet, capsule and/or multiparticulate unit dosage form.

For example, the sustained release materials may be selected from the group of sustained release polymers including, but not limited to, ethylcellulose (Aquacoat® ECD, Aqualon® EC, Ethocel™, Surelease®), non-water soluble polymethacrylates (such as poly(ethyl acrylate-co-methyl methacrylate-co-trimethylammonioethyl methacrylate chloride) (e.g. Eudragit® RL 100, Eudragit® RL PO, Eudragit® RL 30 D, Eudragit RL 12.5, Eudragit® RS 100, Eudragit® RS PO, Eudragit® RS 30 D, Eudragit® RS 12.5), non-water soluble acrylates copolymers (such as poly(ethyl acrylate-co-methyl methacrylate) 2:1 (Eudragit® NE 30 D, Eudragit® NE 40 D, Eudragit® NM 30 D), polyvinyl acetate (Kollicoat® SR 30 D).

In a particular embodiment, the sustained release polymers are selected from the group of non-water soluble polymethacrylates (such as poly(ethyl acrylate-co-methyl methacrylate-co-trimethylammonioethyl methacrylate chloride) (e.g. Eudragit® RL 100, Eudragit® RL PO, Eudragit® RL 30 D, Eudragit RL 12.5, Eudragit® RS 100, Eudragit® RS PO, Eudragit® RS 30 D, Eudragit® RS 12.5), poly(ethyl acrylate-co-methyl methacrylate) 2:1 (Eudragit® NE 30 D, Eudragit® NE 40 D, Eudragit® NM 30 D).

Particular sustained release coatings that may be mentioned include Eudragit® RL 30 D, Eudragit® RS 30 D, Eudragit® NE 30 D and Eudragit® NE 40 D.

Commercially available systems for enteric coatings and coatings for sustained release include variants of OPADRY® (Colorcon), Surelease® (Colorcon), Nutrateric® (Colorcon), Kollicoat® (BASF), Eudragit® (Evonic), (e.g. Eudragit® RL, Eudragit® RS, Eudragit® S, Eudragit® L, Eudragit FS and Eudragit® E), Sheffcoat EC and Sheffcoat Ent (Kerry).

The skilled person will understand that some coatings may require the use of one or more plasticizers to obtain the required results, and the use of such agents will be known to those skilled in the art. Such plasticizers may include, for example, citrate esters, glycerol, propylene glycol, diethyl phthalate, dibutyl phthalate, dibutyl sebacate, tributul citrate, acetylated monoglycerides, triacetin and glycerintriacetate.

Pigments, antitacking agents (e.g. talc) and/or plasticizers may be added to, for example, a polymeric coating solution in order to improve the technical properties of, for example, a membrane and/or modify the release characteristics of the formulation.

The skilled person will also understand that other substances can also be included in the polymer coatings in order to control and/or modify the release characteristics of the formulation. Such substances can, for example, be pore forming, soluble substances such as salts, sugars and soluble polymers (e.g. polyethylene glycol, polyvinyl alcohol and hydroxypropyl methylcellulose).

For example, the sustained release coating as described herein may be a coating designed to allow for the formation of pores therein, which may be referred to as pore forming coating.

Many polymer combinations to achieve sustained (which may also be referred to as modified) release, using a pore-forming film as described above, are possible. Suitability is based on the compatibility of the chosen polymers in each system and this is known to a person skilled in the art. Suitable polymer combinations include, but are not limited to, blends of ethyl cellulose and hydroxypropyl methyl cellulose, blends of ethyl cellulose and Eudragit® L, blends of Eudragit® NM 30 D and Eudragit® L 30 D-55, blends of Eudragit® NE and Eudragit® L, blends of Kollicoat® SR and Kollicoat® MAE and blends of Kollicoat® SR 30 D and Kollicoat® IR.

In one embodiment that may be mentioned, the sustained release coating comprises a blend of Kollicoat® SR 30 D and Kollicoat® IR or Eudragit® NM 30 D and Eudragit® L 30 D-55.

In a further embodiment, the sustained release coating comprises a blend of Kollicoat® SR 30 D and Kollicoat® IR.

In a particular embodiment, the sustained release coating comprises a blend of Kollicoat® SR 30 D and Kollicoat® IR and the polymer ratio is from about 75% to about 95% (e.g. about 75% to about 85%, about 85 to about 95, about 75%, about 80%, about 85%, about 90% or about 95%).

For the avoidance of doubt, pore forming coatings may be applied as (i.e. in the place of) sustained release coatings in configurations as described herein.

For example, the core component of the formulation (as described herein) containing the VPA and/or a pharmaceutically acceptable salt thereof is coated with a blend of two polymers (one water soluble and one non-water soluble, resulting in a pore-forming film for sustained release). As described earlier, such sustained release coatings can be combined with an enteric coating, either before or after the sustained release coating (in particular, before the sustained release coating). In such embodiments, the coatings may modify the release of the VPA and/or a pharmaceutically acceptable salt thereof by altering the ratio of these two polymers. Typically, the polymer ratio (expressed as total percentage of non-water soluble polymer by dry weight in a blend of the two polymers) may be 10-99%. More particularly the polymer ratio may be from 20 to 99%, from 30 to 99%, from 40 to 99%, from 50 to 99%, from 60 to 99%, from 70 to 99%, from 80 to 99% or from 90 to 99%. Yet more particularly, the polymer ratio may be from 60 to 70%, from 70 to 80% or from 80 to 90%. In a particular embodiment, the polymer ratio is from about 75% to about 95% (e.g. about 75% to about 85%, about 85 to about 95, about 75%, about 80%, about 85%, about 90% or about 95%).

For the aviodance of doubt, those skilled in the art will understand that there are several ways to combine one or more coating material in order to achieve the desired release profile. For example, materials can be combined in different coating layers, such as a first sustained release coating covered by a second enteric coating, or together (i.e. mixed) in one or more coating layers, such as a combination of a sustained release polymer and an enteric coating polymer wherein, when the enteric coating polymer dissolves, pores are formed in the sustained release polymer. Such combinations of a sustained release polymer and an enteric coating polymer include, for example, the Nutrateric® system marketed by Colorcon®.

The skilled person will understand that coatings mentioned herein (such as enteric and sustained release coatings) may be formed from combinations of suitable polymers, such as those mentioned herein.

Further, the skilled person will also understand that the thickness of the coating layer(s) can also be altered to achieve a specific release pattern. Furthermore, if coated multiparticulates are used, for example, in a capsule or compressed tablet, different coatings (and/or coating thicknesses) can be used in order to mimic the pattern of PAI-1 plasma concentration for the compounds of the invention. More specifically, a combination of several (e.g. 2 to 5) differently coated multiparticulates may be used to achieve the desired effect in mimicing the pattern of PAI-1 plasma concentration for the compounds.

In particular, the skilled person will be able to adjust the amount of the relevant coating(s), such as the enteric coating, in order to obtain the require release profile (or, in the case of the use of separately coated multiparticulates, the required release profiles). The amount of coating applied to a particular dosage form (e.g. a tablet, capsule or multiparticulates (such as e.g. minitablets and granules)) may be expressed as the weight gain observed for that dosage form upon addition of the coating or in $mg/cm^2$.

Typically, the weight gain upon addition of the relevant coating will be from about 1% to about 200% of the weight of the dosage form (e.g. the tablet, capsule, or multiparticulates (such as e.g. minitablets and granules))), such as from about 2% to about 100%, for example about 2% to about 50%. More particularly, the weight gain may be from about 2% to about 30% of the weight of the dosage form, such as about 2%, about 4%, about 6%, about 8%, about 10%, about 12%, about 14%, about 16%, about 18%, about 20%, about 22%, about 24%, about 26%, about 28% or about 30%. Yet more particularly, the weight gain may be from about 2% to about 20% of the weight of the dosage form. Yet more particularly, the weight gain of each coated layer may be from about 2% to about 20% of the weight of the dosage form.

Typically, the applied amount of each of the relevant coating on the core component of the dosage form (e.g. the tablet, capsule, or multiparticulates (such as e.g. minitablets, pellets and granules)) will be from about 1 $mg/cm^2$ to about 110 $mg/cm^2$, such as from about 1 $mg/cm^2$ to about 55 $mg/cm^2$, for example about 1 $mg/cm^2$ to about 30 $mg/cm^2$. More particularly, the weight gain may be from about 1 $mg/cm^2$ to about 25 $mg/cm^2$ of the weight of the dosage form, such as about 1 $mg/cm^2$, about 2 $mg/cm^2$, about 3 $mg/cm^2$, about 4 $mg/cm^2$, about 5 $mg/cm^2$, about 6 $mg/cm^2$, about 7 $mg/cm^2$ about 8 $mg/cm^2$, about 9 $mg/cm^2$, about 10 $mg/cm^2$, about 11 $mg/cm^2$, about 12 $mg/cm^2$, about 13 $mg/cm^2$, about 14 $mg/cm^2$ or about 15 $mg/cm^2$, about 16 $mg/cm^2$, about 17 $mg/cm^2$, about 18 $mg/cm^2$, about 19 $mg/cm^2$, about 20 $mg/cm^2$, about 21 $mg/cm^2$, about 22 $mg/cm^2$, about 23 $mg/cm^2$, about 24 $mg/cm^2$ or about 25 $mg/cm^2$. Yet more particularly, the applied amount may be from about 1 $mg/cm^2$ to about 20 $mg/cm^2$ (e.g. 1-18 $mg/cm^2$).

In particular embodiments that may be mentioned, coatings may be applied in the following amounts:

protective coating (as described herein)—about 1-15 mg/cm$^2$, about 2-10 mg/cm$^2$, about 3-8 mg/cm$^2$, 3-6 mg/cm$^2$ (e.g. about 3-5 mg/cm$^2$, about 4-6 mg/cm$^2$, about 3 mg/cm$^2$, about 4 mg/cm$^2$, about 5 mg/cm$^2$ or about 6 mg/cm$^2$)

enteric (as described herein)—about 3-25 mg/cm$^2$, about 5-20 mg/cm$^2$, about 11-23 mg/cm$^2$, about 6-18 mg/cm$^2$ (e.g. about 8-16 mg/cm$^2$, about 10-18 mg/cm$^2$, about 12-17 mg/cm$^2$ or about 14-17 mg/cm$^2$)

pore forming system (as described herein)—about 2-15 mg/cm$^2$ (e.g. about 2-12 mg/cm$^2$), about 3-12 mg/cm$^2$, about 4-11 mg/cm$^2$ (e.g. about 4-10 mg/cm$^2$, about 4-9 mg/cm$^2$, about 5-8 mg/cm$^2$ or about 5-9 mg/cm$^2$)

Further coating layers can also be added for other purposes, such as protective coating layers (e.g. moisture protection) and coating layers containing acids which controls the solubility of the drug.

In one embodiment an inner protective film (non-functional with regards to the release profile) is used to seal the core and thereby reduce possible interactions between the inner core and an enteric or sustained release (i.e. functional) film applied thereto, such as those described herein.

For example, in particular embodiments that may be mentioned, tablets as described herein (similarly including multiparticulates, such as minitablets, pellets and granules) may be composed of the following (described as beginning with a central core and moving outwards, i.e. in layers, therefrom):

(a) a tablet core, a protective film, an enteric coating, a sustained release coating;

(b) a tablet core, a protective film, a sustained release coating, an enteric coating;

(c) a tablet core, a protective film, a sustained release coating;

(d) a tablet core, a protective film, an enteric coating, (e) a tablet core, an enteric coating, a sustained release coating;

(f) a tablet core, a sustained release coating, an enteric coating;

(g) a tablet core, a sustained release coating;

(h) a tablet core, an enteric coating, wherein suitable tablet cores, protective films, sustained release coatings and enteric coatings (and amounts and methods of application thereof) will be known to those skilled in the art, such as may be described herein.

Particular such embodiments that may be mentioned include those described at points (a) to (d) above.

For the avoidance of doubt, in situations where the secondary acid component (component (b), as described herein) is included as a coating layer (rather than as a component of the core), such a layer may be provided as an additional layer, and at any interval, in the arrangements described as points (a) to (h) above.

Examples of polymers for protective coatings/films (that may provide moisture protection, oxygen protection and/or taste masking) include, but are not limited to, Kollicoat® Protect (polyvinyl alcohol-polyethylene glycol copolymer and polyvinyl alcohol, BASF®), Kollicoat® Smartseal 30 D (methyl methacrylate (MMA) and diethylaminoethyl methacrylate), Opadry® amb II (Colorcon®), Eudragit® E 100, Eudragit® E 12.5, Eudragit® E PO, Hydroxypropylmethylcellulose (e.g. Methocel®, Anycoat®, Pharmacoat®), Hydroxypropylcellulose (e.g. Coatcel® and Klucel®), Hydroxyethylcellulose (e.g. Natrosol®), poly (vinyl pyrrolidone) (e.g. Kollidon®), poly (vinyl pyrrolidone)/poly (vinyl acetate) copolymers, poly (vinyl alcohol)/poly (ethylene glycol) copolymers (e.g. Kollicoat® IR), poly (ethylene glycol), maltodextrines and polydextrose.

In one embodiment the protective film polymer is selected from the group of Kollicoat® Protect, Kollicoat® Smartseal 30 D, Opadry® amb II, Eudragit® E 100, Eudragit® E 12.5, Eudragit® E PO, Hydroxypropylmethylcellulose (e.g. Methocel®, Anycoat®, Pharmacoat®), Hydroxypropylcellulose (e.g. Coatcel® and Klucel®), Hydroxyethylcellulose (e.g. Natrosol®), poly (vinyl pyrrolidone) (e.g. Kollidon®), poly (vinyl pyrrolidone)/poly (vinyl acetate) copolymers, poly (vinyl alcohol)/poly (ethylene glycol) copolymers (e.g. Kollicoat® IR) and poly (ethylene glycol).

In one embodiment the protective film polymer is Kollicoat® IR.

The skilled person will understand that different materials have different properties e.g. when it comes to the dissolution pH and can thus be used to control the absorption pattern, e.g. delaying release of a drug for a specific time, by a person skilled in the art. In addition, the thickness of the coating can also be altered to achieve a specific pattern. Furthermore, if coated multiparticulates are used e.g. in a capsule or compressed tablet, different coatings (and/or coating thicknesses) can be used in order to mimic the pattern of PAI-1 plasma concentration for the compounds of the invention. More specifically, a combination of several (e.g. 2-5) differently coated multiparticulates (such as e.g. minitablets and granules)) may be used to achieve the desired effect in mimicing the pattern of PAI-1 plasma concentration for the compounds of the invention.

As described herein, one way of extending the delay in absorption of an enteric coating is to mix an enteric coating polymer with a smaller amount of a sustained release polymer; as described in e.g. Tirpude and Puranik, J Adv Pharm Technol Res 2011, where 10% of sustained release acrylic polymers (Eudragit NE30D) was mixed with 90% enteric acrylic polymers (Eudragit L 30 D-55). Thus, materials such as polymers with different dissolution characteristics may be combined in different ratios to achieve a desired pattern of absorption according to the invention. Other examples of methods to achieve different absorption patterns by using various grades of hydrophilic polymers and how to make matrix tablets from granules are described in Roy, Brahma, Nandi and Parida, Int J Appl Basic Med Res. 2013.

Different ways to achieve controlled release using matrix tablets and description of different polymers and matrices is also described in http://www.pharmainfo.net/reviews/matrix-tablets-important-tool-oral-controlled-release-dosage-forms, the disclosures of which are incorporated herein by reference in their entirety.

Compounds of the invention may be coated by, or administered with, a material to prevent their inactivation. For example, the active material may be administered in an adjuvant, co-administered with e.g. enzyme inhibitors or in liposomes. Adjuvants contemplated herein include, but are not limited to, resorcinols, non-ionic surfactants such as polyoxyethylene oleyl ether and n-hexadecyl polyethylene ether. Enzyme inhibitors include; but are not limited to, pancreatic trypsin inhibitor, diisopropylfluorophosphate (DFP) and trasylol. Liposomes include water-in-oil-in-water P40 emulsions as well as conventional liposomes. Dispersions can also be prepared in glycerol, liquid polyethylene glycols, and mixtures thereof and in oils. Under ordinary conditions of storage and use, these preparations may also contain a preservative to prevent the growth of microorganisms.

As described herein, the skilled person will understand that when administered orally the active compound may be combined with a diluent or with an edible carrier, or it may be enclosed in hard or soft shell gelatin capsule, or it may be compressed into tablets, or it may be incorporated directly with the food of the diet. For oral therapeutic administration, the active material may be incorporated with excipients and used in the form of ingestible tablets, buccal tablets, troches, capsules, elixirs, suspensions, syrups, wafers, and the like. In addition, the active material may be incorporated into sustained-release preparations and formulations. For example, the active material may be incorporated in entero-tablets/capsules and/or bi-phasic release formulations, which formulations will be known to the skilled person. For example, bi-phasic release formulation may be of the type described in US2007/0232528A1 (the contents of which are incorporated herein in their entirety), which formulations may be suitable for administration during a period from about 22:00 to 00:00 hours (e.g. about 23:00 hours).

As described herein, the pharmaceutical compositions according to present invention may comprise one or more excipients.

As used herein, the term "pharmaceutically acceptable excipient" will include pharmaceutically acceptable adjuvants, diluents and carriers, as known to those skilled in the art. This may include any and all solvents, dispersion media, coatings, antibacterial and antifungal agents, isotonic and absorption delaying agents and the like.

Examples of pharmaceutical excipients suitable for preparation of tablets and multiparticulates such as minitablets and granules include, but are not limited to binders, fillers or diluents, lubricants, glidants and disintegrants.

For the avoidance of doubt, excipients that control the release of the active substance can be included. Further, a combination of excipients may also be used. For example, excipients of the type known as HFE (high functionality excipient), which are co-processed material containing excipients with different functions, can also be employed.

The skilled person will understand that the amount of excipient(s) employed will depend upon how much active agent is to be used. Further, one excipient can perform more than one function.

For example, binders may include, but are not limited to, starches such as potato starch, wheat starch, corn starch; microcrystalline cellulose; celluloses such as hydroxypropyl cellulose, hydroxyethyl cellulose, hydroxypropylmethylcellulose (HPMC), ethyl cellulose, sodium carboxymethylcellulose; natural gums like acacia, alginic acid, guar gum, tragacanth; liquid glucose, dextrin, povidone, copovidone, syrup, polyethylene oxide, poly-N-vinyl amide, polyethylene glycol, gelatin, poly propylene glycol, combinations there of and other materials known to one of ordinary skill in the art and mixtures thereof. In one embodiment, binders are selected from the group consisting of hydroxypropyl cellulose, HPMC, povidone, copovidone and gelatin.

Particular binders that may be mentioned include those selected from the group consisiting of copovidone and HPMC.

Further, fillers or diluents may include, but are not limited to, confectioner's sugar, compressible sugar, dextrates, dextrin, dextrose, fructose, lactitol, mannitol, sucrose, starch, lactose, xylitol, sorbitol, talc, microcrystalline cellulose, calcium carbonate, calcium phosphate dibasic or tribasic, calcium sulphate, and the like.

Particular fillers that may be mentioned include those selected from the group consisting of mannitol, starch, lactose, microcrystalline cellulose and calcium phosphate dibasic (such as microcrystalline cellulose).

Further, lubricants that may be mentioned include, but are not limited to, stearates (such as Mg, Al, Ca or Zn stearate), polyethylene glycol, glyceryl behenate, glyceryl monostearate, mineral oil, sodium stearyl fumarate, stearic acid, hydrogenated vegetable oil and talc.

Particular lubricants that may be mentioned include those selected from the group consisiting of Mg-stearate, Ca-stearate and sodium stearyl fumarate (such as Mg-stearate).

Further, glidants that may be mentioned include, but are not limited to, silicon dioxide; magnesium trisilicate, powdered cellulose, starch, talc and tribasic calcium phosphate, calcium silicate, magnesium silicate, colloidal silicon dioxide, silicon hydrogel, silica gel and other materials known to those skilled in the art.

Particular glidants that may be mentioned include those selected from the group consisting of talc, colloidal silicon dioxide and silica gel (such as colloidal silicon dioxide).

As described herein, formulations according to present invention may also comprise a disintegrant which may be included in all or part of the oral dosage form to ensure rapid disintegration of the dosage form or part of the dosage form (for example, one of the layers in a bilayer tablet) after administration.

Particular disintegrants that may be mentioned include, but are not limited to: microcrystalline cellulose, alginic acid, pregelatinized starch, carboxymethylcellulose calcium, carboxymethylcellulose sodium, croscarmellose sodium, crospovidone, guar gum, magnesium aluminium silicate, sodium alginate, sodium starch glycolate and starches, and other materials known to those skilled in the art and combinations thereof.

Particular disintegrants that may be mentioned include those selected from the group microcrystalline cellulose, pregelatinized starch, croscarmellose sodium, crospovidone and sodium starch glycolate (such as croscarmellose sodium).

As described herein, formulations according to present invention may also comprise a release controlling substance.

Particular release controlling substances that may be mentioned include, but are not limited to, polymers, such as hydroxypropyl cellulose, hydroxypropyl methylcellulose, carboxymethyl cellulose, chitosan, aloe mucilage, pectin, ethyl cellulose, polyvinyl chloride, polyethylene, polyethylene oxide, polyvinyl alcohol (PVA), polymethacrylates (such as the polymers known under the tradename Eudragit®), carbomer and polyvinylpyrrolidone (PVP). Further excipients that can be used for controlling the release of the active ingredient include hydrophobic excipients, such as waxes, fats, fatty alcohols, fatty acid esters and the like.

More particular release controlling substances that may be mentioned include those selected from the group consisting of hydroxypropyl cellulose, hydroxypropyl methylcellulose, carboxymethyl cellulose, ethyl cellulose, polyethylene oxide and acrylic copolymers (such as hydroxypropyl methylcellulose).

For the avoidance of doubt, the skilled person will appreciate that there may be considerable overlap between the above-mentioned excipients in common usage, as a given additive is often classified differently by different practitioners in the field, or is commonly used for any of several different functions. Thus, the above-mentioned additives should be taken as merely exemplary, and not limiting, of the types of excipients that can be included in compositions of the present invention.

One or more of these excipients can be selected and used by the skilled person having regard to the particular desired properties of the dosage form by routine experimentation without any undue burden. Further, the amount of each type of excipients employed may vary within ranges as known to those skilled in the art.

Thus, as described herein, pharmaceutical formulations in the form of tablets, troches, pills, capsules, and the like may also contain the following: a binder such as gum tragacanth, acacia, corn starch, or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye, and flavoring such as cherry or orange flavor. Of course, any material used in preparing any dosage unit form should be pharmaceutically pure and substantially non-toxic in the amounts employed.

The use of excipients is further described in, for example, Remington's Pharmaceutical Science and U.S. Pharmacopeia (The United States Pharmacopeia—National Formulary (USP—NF)), Remington: The Science and Practice of Pharmacy, 19th Ed. (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, 7th Ed. (Lippincott Williams Wilkins 1999), the contents of which are incorporated herein by reference.

In particular, it has been found that pharmaceutical compositions able to release compounds of the invention comprised therein in a delayed manner (as may be required for use in the eight aspect of the invention), may be provided through the preparation of formulations wherein the compound of the invention is present in combination with a further (secondary) acid component.

Thus, in a ninth aspect of the invention, there is provided a pharmaceutical formulation having one or more component comprising:
(a) valproic acid (VPA) and/or a pharmaceutically acceptable salt thereof; and
(b) one or more secondary acid and/or a pharmaceutically acceptable salt thereof.

The skilled person will understand that references to a pharmaceutical formulation having one or more component will indicate that the formulation may be provided as one (solid and discrete) unit or as a combination of such units. For the avoidance of doubt, particular pharmaceutical formulations that may be mentioned include tablets (i.e. solid tablets for oral administration), or alternatively capsules containing solid multiparticulates (e.g. minitablets, pellets or granules), also for oral administration.

Thus, the formulation of the ninth aspect of the invention may also be referred to as a solid pharmaceutical formulation in the form of a tablet, or capsule containing solid multiparticulates, comprising:
(a) valproic acid (VPA) and/or a pharmaceutically acceptable salt thereof; and
(b) one or more secondary acid and/or a pharmaceutically acceptable salt thereof.

As used herein (particularly in relation to the ninth aspect of the invention), references to a secondary acid and/or a pharmaceutically acceptable salt thereof may refer to an acid other than VPA or a pharmaceutically acceptable salt thereof (i.e. a further, additional acid component).

The skilled person will undertand that references herein to secondary acids will refer to protic (i.e. Brønsted-Lowry) acids.

The skilled person will understand that suitable secondary acids and pharmaceutically acceptable salts thereof will be those known in the art as pharmaceutically acceptable acids (such as those described herein as being suitable for the formation of pharmaceutically acceptable salts).

In particular embodiments, component (b) in the formulation of the ninth aspect of the invention is one or more secondary acid, as described herein (i.e. not a salt thereof).

Particular secondary acids (i.e. acids forming component (b)) that may be mentioned include organic acids (i.e. pharmaceutically acceptable organic acids). References to organic acids will be readily understood by those skilled in the art as referring to an organic (i.e. carbon-based) compound having one or more (e.g. one or two, such as two) acidic moieties (i.e. moieties comprising an acidic proton).

For the avoidance of doubt, wherein component (b) is one or more organic acid (i.e. not a salt thereof), the skilled person will understand that suitable components will have at least one carboxylic acid group present in non-salt form (i.e. as the free acid), although additional carboxylic acid groups present in said component may be in salt form, as described herein.

In particular embodiments wherein component (b) is one or more organic acid, each carboxylic acid group present in such acids will be in non-salt (i.e. free acid) form (which, for the avoidance of doubt, will refer to such groups being in free acid form upon preparation of the composition).

More particular secondary acids that may be mentioned, but are not limited to, adipic acid, citric acid, fumaric acid, glycine, lysine, maleic acid, malic acid, lactic acid, sorbic acid, potassium phosphate monobasic, sodium phosphate monobasic, succinic acid, acetylsalicylic acid and tartaric acid.

In a particular embodiment the suitable secondary acid is selected from the group consisting of sorbic acid, acetylsalicylic acid, fumaric acid, adipic acid and succinic acid.

In a particular embodiment the suitable secondary acid is selected from the group consisting of sorbic acid, acetylsalicylic acid, fumaric acid and adipic acid.

In a particular embodiment the suitable secondary acid is selected from the group consisting of sorbic acid, acetylsalicylic acid and fumaric acid.

In a particular embodiment, the suitable secondary acid is selected from the group consisting of acetylsalicylic acid, succinic acid and fumaric acid.

In a more particular embodiment, the suitable secondary acid is fumaric acid.

In particular embodiments, the one or more suitable secondary acid is not (i.e. is other than) acetylsalicylic acid (aspirin).

In alternative embodiments, the one or more suitable secondary acid is acetylsalicylic acid (aspirin).

In particular emboidments that may be mentioned, the suitable secondary acid will have a solubility in water (e.g. in distilled water at 25° C.) of below about 60 g/l (e.g. below about 50, about 40, about 30, about 20, about 10, about 8 or about 5 g/l).

The skilled person will appreciate that, where the one or more suitable secondary acid is acetylsalicylic acid (aspirin), that component may also provide a therapeutic effect, such as a synergistic effect in treatment when combined with VPA, or a pharmaceutically acceptable salt thereof. In such instances, the skilled person will be able to select an amount of acetylsalicylic acid that will provide the required therapeutic effect and will result in a composition having the required release profile.

In particular such embodiments, the amount of acetylsalicylic acid is between about 30 mg to about 500 mg in relation to the dose being administered per 24 hours. In another such embodiment, the amount of acetylsalicylic acid is between about 50 mg to about 350 mg in relation to the dose being administered per 24 hours.

In further such embodiments, the amount of acetylsalicylic acid is between about 75 mg to about 325 mg in relation to the dose being administered per 24 hours, such as about 75 mg, about 160 mg or about 320 mg (e.g. about 75 mg or about 160 mg).

In particular embodiments, references to one or more secondary acid may refer to one or two (e.g. one) secondary acid(s).

The skilled person will be able to select the amount of secondary acid (either in absolute terms or relative to the amount of VPA and/or pharmaceutically acceptable salt thereof) required in the relevant component (i.e. the component comprising the VPA and/or pharmaceutically acceptable salt thereof and secondary acid) in order to obtain the required release profile.

In particular embodiments, the secondary acid (i.e. component (b)) may generally be present in an amount from about 1% to about 200% of the weight of the VPA and/or a pharmaceutically acceptable salt thereof in the relevant component (i.e. in the formulation, such as in the core component of the formulation). Alternatively, the secondary acid (i.e. component (b)) may generally be present in an amount from about 0.1% to about 200% of the weight of the VPA and/or a pharmaceutically acceptable salt thereof.

For example, the secondary acid may generally be present in an amount from about 5% to about 150% (e.g. about 5% to about 100%) of the weight of the VPA and/or a pharmaceutically acceptable salt thereof in the relevant component, such as about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100%.

In particular embodiments, the amount of secondary acid will generally be from about 10% to about 70% of the weight of the VPA and/or a pharmaceutically acceptable salt thereof in the relevant component.

In more particular embodiments, the amount of secondary acid will generally be from about 10% to about 50% of the weight of the VPA and/or a pharmaceutically acceptable salt thereof in the relevant component, such as about 10%, about 15%, about 20%, about 25%, about 30%, about 35%, about 40%, about 45% and about 50%.

In certain embodiments, the amount of secondary acid will generally be from about 80% to about 120% of the weight of the VPA and/or a pharmaceutically acceptable salt thereof in the relevant component, such as about 90% to about 110%.

For the avoidance of doubt, in particular emboidments the secondary acid may be present in an amount from about 1% to about 15% of the weight of the VPA and/or a pharmaceutically acceptable salt thereof in the relevant component, such as about 1% to about 10%, about 1% to about 5%, about 5% to about 15%, about 5% to about 10% (e.g. about 1% or about 5%, or about 2 to about 5%, about 2 to about 7%, about 3 to about 7%, about 4 to about 8%, about 8 to about 12%, or about 7 to about 13%).

In alternative embodiments the secondary acid may be present in an amount from about 0.1% to about 15% of the weight of the VPA and/or a pharmaceutically acceptable salt thereof in the relevant component, such as about 0.5% to about 10% or about 0.5% to about 5% (e.g. (e.g. about 0.1 to about 3%, about 0.5 to about 3%, about 0.1 to about 5%, or about 0.5 to about 5%).

The skilled person will understand that ratios of various components in the pharmaceutical formulation may also be expressed as molar percentages. Thus, each percentage describing the amount of secondary acid by weight as provided herein may also be expressed as a molar percentage.

As described herein (e.g. in relation to the eighth aspect of the invention), pharmaceutical formulations comprising compounds of the invention may comprise one or more coating.

In particular, such a coating may be present on the one or more component comprising VPA and/or a pharmaceutically acceptable salt thereof and the secondary acid, in which cases each such component may be referred to as a core component.

As described herein, such core components may form a single (coated) tablet or may be provided in the form of multiparticulates, which multiparticulates may be individually coated, and which multiparticulates may be delivered as a single dose (e.g. compressed into a tablet or delivered in a capsule, such as a hard capsule, e.g. a hard gelatin capsule).

As described herein, particular coatings that may be employed in such formulations may include enteric coatings and sustained release coatings, such as those described herein (including, for the avoidance of doubt, those described in the eighth aspect of the invention).

For the avoidance of doubt, in particular embodiments, the coating may be an enteric coating (e.g. of a type and in an amount as described herein).

In furthers embodiment, the core component may be coated with a combination of a sustained release coating (e.g. of a type and in an amount as described herein) and an enteric coating (e.g. of a type and in an amount as described herein). For the avoidance of doubt, such coatings may be applied separately (i.e. in distinct layers), such as by providing a core composition which is coated with an enteric coating (i.e. as a first coating layer) and then a sustained release coating (i.e. as a second coating layer), wherein suitable enteric coatings and sustained release coatings include those as described herein.

In a yet further embodiment, the core component may be coated with a sustained release coating (e.g. of a type and in an amount as described herein) and then an enteric coating (e.g. of a type and in an amount as described herein).

In a yet further embodiment, the core component may be coated with an enteric coating (e.g. of a type and in amount as described herein) and then a sustained release coating (e.g. of a type and in amount as described herein).

For the avoidance of doubt, in particular embodiments, the core component may be coated with a protective film, such as is described in the eighth aspect of the invention.

In particular embodiments, the secondary acid component of pharmaceutical formulations of the ninth aspect of the invention as described herein (component (b)) may itself be present as a coating (i.e. a coating layer) on the component comprising VPA or a pharmaceutically acceptable salt thereof (component (a)), which coating layer may be distinct from other coating layers (e.g. enteric and/or sustained release coatings) or combined with (e.g. mixed with) such coatings.

For example, in certain embodiments, the secondary acid component of pharmaceutical formulations of the ninth aspect of the invention as described herein (component (b)) may itself be present as a coating (i.e. a coating layer) on the component comprising VPA or a pharmaceutically acceptable salt thereof (component (a)), which composition is then further coated (e.g. with enteric and/or sustained release coatings). In such instances, formulations may be described as having a core that is component (a), which is coated by a first coating which is component (b) and an optional second (or further) coating (which may be, for example, one or more enteric and/or sustained release coating(s), or mixtures thereof).

For the avoidance of doubt, all types and components of formulations as described in the eighth aspect of the invention (including those described in particular embodiments and combinations of embodiments thereof) may also apply to the formulations of the ninth aspect of the invention.

For example, in a particular embodiment of the ninth aspect of the invention, the pharmaceutical composition may further comprise one or more pharmaceutically acceptable excipients (e.g. a pharmaceutically acceptable adjuvant, diluent or carrier), such as those described herein.

It is also been found that formulations (e.g. tablets or multiparticulates) comprising a secondary acid allow for beneficial dissolution profiles with high loading of the active pharmaceutical ingredient (i.e. valproic acid, or a pharmaceutically acceptable salt thereof; referred to herein as component (a)).

Thus, in particular embodiments, the formulation comprises one or more component having a solid core comprising component (a), wherein component (a) is present in an amount that is at least 30% (e.g. at least 35%, such as at least 40%, at least 45%, at least 50%, at least 55%, at least 60%, at least 65% or at least 70%) by weight thereof, and optionally wherein said solid core further comprises component (b).

In particular embodiments, component (a) may generally be present in an amount that is at least (e.g. greater than) 30% by weight of the core component of the formulation (i.e. the solid core which optional coating layers may be applied to).

In more particular embodiments, component (a) is present in an amount greater than 35% by weight of the core component of the formulation, such as at least 40%, at least 45% or, particularly, at least 50%.

In yet more particular embodiments, component (a) is present in an amount greater than 55% by weight of the core component of the formulation, such as at least 60%, at least 65% or, particularly, at least 70%, at least 75% or at least 80%.

For the avoidance of doubt, the skilled person will understand that references to the core component of the formulation (i.e. in the form of a solid tablet or multiparticulates for oral administration) will refer to a solid portion forming the central component of the formulation, to which coating layers may be applied. For the avoidance of doubt, component (a) forms part of the core component of the formulation. Thus, the core may further comprise, in addition to component (a), excipients as described herein and/or (e.g. and) component (b) as described herein, with the skilled person being able to calculate appropriate amounts of said components in core composition as required.

For the avoidance of doubt, the skilled person will understand that the total amount (as a % by weight) of components in the formulation (e.g. in the core component of the formulation; such as component (a)) must be calculated taking account of the other components of the formulation or particular component thereof, and by definition cannot exceed 100% by weight of the formuluation or particular component thereof.

As described herein, pharmaceutical formulations as described in the ninth aspect of the invention may be useful in providing the release profile as required in the eight aspect of the invention.

Thus, in particular embodiments, the pharmaceutical formulation of the ninth aspect of the invention has a release profile as described in the eighth aspect of the invention (including all embodiments thereof).

For the avoidance of doubt, embodiments described herein as relating to individual features of formulations (e.g. the formulation of the ninth aspect of the invention) may be combined to describe further emboidments relating to the combination of those features in such formulations without departing from the teaching of the invention.

For example, embodiments exists in respect of which one or more of the following features are present:

(I) the formulation having one or more solid core component comprising component (a) and, in particular embodiments, component (b), and optionally comprising one or more pharmaceutically acceptable excipients(s):

(II) component (b) is fumaric acid;

(III) component (a) is present in the solid core component in an amount that is at least 30% (e.g. at least 50%) by weight thereof;

(IV) component (b) is present (e.g. in the core component) in an amount that is about 0.1% (e.g. about 1%) to about 15% (e.g. about 10%) by weight.

In addition, the following features may be present:

(a) a protective coating applied to the core (of a type as described herein);

(b) an enteric coating (such as Eudragit FS 30 D) applied to the protective film;

and optionally (c) a pore forming coating (as described herein), which may be applied between the enteric coating and the protective film or, particularly, on the enteric coating (such as Eudragit L 30 D 55).

In instances where only an enteric coating is used, component (b) may be present (e.g. in the core component) in an amount that is about 5-15% by weight (e.g. about 8-12, about 10% by weight).

In instances where a pore forming coating is used, component (b) may be present (e.g. in the core component) in an amount that is about 1% to about 5% by weight.

Without wishing to be bound by theory, it is thought that the secondary acid component may act to modify the solubility of VPA and/or pharmaceutically acceptable salts thereof. Further, where the core component is coated (e.g. with a suitable enteric coating), the acid component may serve to decrease the pH in the proximity of that coating thus delaying its dissolution, which in turn will serve to further delay the release of the active ingredients (i.e. VPA and/or pharmaceutically acceptable salts thereof).

As described herein, pharmaceutical formulations according to the present invention (such as tablets and/or capsules) formulated to delay the release of compounds of the invention from said tablet after oral administration (as described in the eight aspect of the invention, and embodiments thereof) are particularly suited for use in treating or preventing a pathological condition associated with excess fibrin deposition and/or thrombus formation in accordance with the particular dosage regimes described herein.

Thus, in a tenth aspect of the invention, there is provided a pharmaceutical composition as described in the eight or ninth aspects of the invention (including any one or more embodiments thereof) for use in treating or preventing a pathological condition associated with excess fibrin deposition and/or thrombus formation, wherein said treatment is as described in any one of the first to seventh aspects of the invention (including any one or more embodiments thereof).

In an alternative tenth aspect of the invention, there is provided the use of a pharmaceutical composition as described in the eight or ninth aspects of the invention (including any one or more embodiments thereof) in the manufacture of a medicament for use in treating or preventing a pathological condition associated with excess fibrin deposition and/or thrombus formation, wherein said treatment is as described in any one of the first to seventh aspects of the invention (including any one or more embodiments thereof).

In a further alternative tenth aspect of the invention, there is provided a method of treating or preventing (such as reducing the risk of developing, as described herein) a pathological condition associated with excess fibrin deposition and/or thrombus formation as described in any one of the first to seventh aspects of the invention comprising administering to a patient in need thereof a therapeutically effective amount of a pharmaceutical composition as described in the eight or ninth aspects of the invention (including any one or more embodiments thereof).

In a further alternative tenth aspect of the invention, there is provided a method of treating or reducing the risk of developing a pathological condition associated with excess fibrin deposition and/or thrombus formation as described in any one of the first to seventh aspects of the invention comprising administering to a patient in need thereof a therapeutically effective amount of a pharmaceutical composition as described in the eighth or ninth aspects of the invention (including any one or more embodiments thereof).

As described herein, the skilled person will be able to adjust the formulation and manner of administration of compounds of the invention in order to achieve the desired parameters, such as the desired timing and/or levels of plasma concentrations of specific agents.

For instance, the skilled person will be aware that various formulations of compounds of the invention are commercially available and may be administered in a manner suitable for use in, inter alia, treatments as described in the first to seventh aspects of the invention.

Thus, in particular embodiments of invention (for example, particular embodiments of the first to seventh and ninth aspects of the invention), there is provided the use of the VPA, or a pharmaceutically acceptable salt thereof, in treating or preventing a pathological condition associated with excess fibrin deposition and/or thrombus formation, wherein said treatment comprises administering a pharmaceutical composition comprising a dose of VPA, or a pharmaceutically acceptable salt thereof, to a patient in a form (i.e. a specific formulation), and at a specific dose and time, as indicated in the following table.

| Formulation name | Dose of active agent | Time of administration |
| --- | --- | --- |
| Depakote | 125 to 750 mg (e.g. 250 mg or 500 mg) once daily | Approximately 22:00 hours to 00:00 hours (e.g. about 23:00), or before sleep. If administered with food absorption may be delayed and the drug can be administered from approximately 19:00 to 21:00 hours. |
| Depakote ER | 250 to 750 mg (e.g. 250 or 500 mg) once daily | Approximately 18:00 to 21:00 (e.g. about 19:00), or before sleep. |
| Depakote sprinkle capsules | 125 to 750 mg (e.g. 250 or 500 mg) once daily | Approximately 22:00 hours to 00:00 hours (e.g. about 23:00), or before sleep. If administered with food absorption may be delayed and the drug can be administered from approximately 20:30 to 23:00 hours (e.g. about 22:00). |
| Orfiril enterotablets | 150 to 750 mg (e.g. 300 mg or 600 mg) once daily | 22:00 hours to 00:00 (e.g. about 23.00) or before sleep. |
| Orfiril Long depot granules | 200 to 600 mg (e.g. 500 mg) once daily | 20:00 hours to 00:00 (e.g. about 22:00) or before sleep. |
| Ergenyl enterotablets | 200 to 600 mg (e.g. 300 mg or 500 mg) once daily | 21:00 hours to 00:00 (e.g. about 23:00) or before sleep. |
| Ergenyl Retard depot granules | 100 to 750 mg (e.g. 250 mg or 500 mg) once daily | 22:00 to 01:00 (e.g. about 23.00) or before sleep. |
| Absenor enterotablets | 100-600 (e.g. 300 or 500 mg) once daily | 21:00 to 00:00 (e.g. about 23.00) or before sleep. If administered with food absorption may be delayed and the drug can be administered from approximately 19:00 to 22:00 hours. |

-continued

| Formulation name | Dose of active agent | Time of administration |
|---|---|---|
| Absenor tablets | 300 to 600 mg (e.g. 300 mg) once daily | 23:00 to 01:00 (e.g. about 00.30) or before sleep. |
| Convulex capsules | 150 to 600 mg (e.g. 300 or 500 mg) once daily | 21:00 hours to 00:00 (e.g. about 23:00) or before sleep. |
| Epilim gastroresistant tablets | 100 to 600 mg (e.g. 400 or 500 mg) once daily | 21:00 to 00:00 (e.g. about 23.00) or before sleep. |
| Epilim Chrono/Depakine Chrono | 200 to 800 mg (e.g. 300 or 500 mg) once daily | 20:00 to 00:00 (e.g. about 22.00) or before sleep. |
| Epilim Chronospheres | 100 to 750 (e.g. 250 or 500 mg) once daily | 19:00 to 22:00 (e.g. about 20:30) or before sleep. |
| Valprotek CR | 300 to 600 mg (e.g. 300 or 500 mg) once daily | 19:00 to 22:00 (e.g. about 20.30) or before sleep. |
| Depakene capsules | 250 to 750 mg (e.g. 250 or 500 mg) once daily | 21:00 hours to 00:00 (e.g. about 23:00) or before sleep. |
| Depakene R | 200 to 600 mg (e.g. 400 mg) once daily | 16:00 to 19:00 (e.g. about 17:30) |
| Selenica R | 200 to 600 mg (e.g. 400 mg) once daily | 9:00 to 12:00 (e.g. about 10:30) |
| Episenta Prolonged release capsules | 150 to 750 mg (e.g 300 or 600 mg) once daily. | 21:00 hours to 00:00 (e.g. about 22:00) or before sleep. |
| Episenta Prolonged release granules | 150 to 750 mg (e.g 300 or 600 mg) once daily. | 21:00 hours to 00:00 (e.g. about 22:00) or before sleep. |
| Stavzor delayed release capsules | 150 to 750 mg (e.g 300 or 600 mg) once daily. | 23:00 hours to 01:00 (e.g. about 23:30) or before sleep. If administered with food absorption may be delayed and the drug can be administered from approximately 20:00 to 23:00 hours. |
| Valproic Acid capsules, USP (Teva) | 250 to 750 mg (e.g. 250 mg or 500 mg) once daily | Approximately 22:00 hours to 00:00 hours (e.g. about 23:00), or before sleep. If administered with food absorption may be delayed and the drug can be administered from approximately 19:00 to 21:00 hours. |
| Ergenyl Retard tablets | 100 to 750 mg (e.g. 250 mg or 500 mg) once daily | 22:00 to 01:00 (e.g. about 23:00) or before sleep. |

As used herein, references to the name of certain formulations will refer to the corresponding formulation as sold/marketed in the relevant territory (e.g. in the US, UK or Sweden) as on 1 Oct. 2014.

References in the above table to specific formulations by a specific name will include references to substantially identical formulations that may be referred to by another name (e.g. identical formulations sold and/or marketed using a different product name).

As described herein, the skilled person will understand that administration of a formulation to a patient with or shortly after food may delay release of the active ingredient and will be able to adjust the time of administration accordingly. Unless otherwise stated, references herein to administration of a particular formulation at a particular time (e.g. within a particular time period) will refer to administration to the patient on an empty stomach.

Combination Treatments

Compounds of the invention may also be administered in combination with (e.g in a combined formulation with) other therapeutic agents that are useful in the treating or preventing a pathological condition associated with excess fibrin deposition and/or thrombus formation.

In particular, pharmaceutical compositions as described in the eight aspect of the invention (including embodiments thereof) may comprise compounds of the invention together with one or more pharmaceutically acceptable excipients and one or more other therapeutic agents that are useful in the treating or preventing a pathological condition associated with excess fibrin deposition and/or thrombus formation.

In a particular embodiment of the first to seventh aspects of the invention, the VPA, or pharmaceutically acceptable salt thereof, is administered in combination with one or more (e.g. one) other therapeutic agents that are useful in the treating or preventing a pathological condition associated with excess fibrin deposition and/or thrombus formation.

In a particular embodiment of the eight aspect of the invention, the pharmaceutical formulation further comprises one or more (e.g. one) other therapeutic agents that are useful in the treating or preventing a pathological condition associated with excess fibrin deposition and/or thrombus formation. In such embodiments, the compounds of the invention may be provided in admixture with said one or more other therapeutic agent.

Thus, the skilled person will understand that the invention further provides a process for the preparation of pharmaceutical formulations as described herein (such as those described in the eight aspect of the invention, including embodiments thereof), which process comprises the steps of:

(a) bringing compounds of the invention into association with one or more pharmaceutically acceptable excipient (e.g. to form an admixture thereof) and/or one or more (e.g. one) other therapeutic agents that are useful in the treating or preventing a pathological condition associated with excess fibrin deposition and/or thrombus formation; and (b) formulating as a tablet or capsule (as described herein, e.g. with one or more coating).

As referred to herein, other therapeutic agents that are useful in the treating or preventing a pathological condition associated with excess fibrin deposition and/or thrombus formation include: one or more anti-thrombolytic agents; and/or one or more anticoagulant agents; and/or one or more antiplatelet agents; and/or one or more vasodilators, as known to those skilled in the art.

In particular embodiments, compounds of the invention may administered and/or formulated in combination with:
one or more anti-platelet agents, including but not limited to aspirin, persantin, ticagrelor and clopidogrel;
one or more anticoagulant agents, such as heparin, low molecular weight heparin (LMWH), warfarin, anisindione, phenindone, bishydroxycoumarin, bivalirudin, eptifibatid; one or more vasodilators such as nitriles (for example, amylnitrile, nitroglycerin, sodium nitrile, isosorbide dinitrate), papaverine, nicotinic acid and cyclandelate.
one or more agents preventing cardiovascular events such as, but not limited to statins, beta blockers, angiotensin converting enzyme inhibitors, angiotensin II receptor antagonists or diuretics; and/or
one or more anti-inflammatory agents including steroids and NSAIDs (including but not limited to aspirin, ibuprofen, naproxen and diclofenac);
one or more thrombolytic agents selected from, for example, recombinant t-PA, prourokinase, urokinase or streptokinase.

In more particular embodiments, compounds of the invention may administered and/or formulated in combination with aspirin (i.e. a therapeutically effective amount of aspirin).

In yet more particular embodiments, compounds of the invention may be administered and/or formulated in combination with clopidogrel (i.e. a therapeutically effective amount of Clopidogrel) or ticagrelor (i.e. a therapeutically effective amount of ticagrelor).

For the avoidance of doubt, the skilled person will understand that the term "administered in combination with" includes concomitant, sequential and separate administration. In this regard, sequential administration may refer to administration within the same therapeutic intervention (e.g. within one hour of the compound of the invention).

The skilled person will understand that references to an agent being administered in combination with another agent may also include a kit-of-parts comprising the relevant agents (i.e. as separate components within the same kit).

The skilled person will also understand that references to a first agent being administered in combination with a second agent will also the second agent being administered in combination the first agent, and so forth.

Patient Groups

The skilled person will understand that references herein to a "patient" will refer to living animals who may be subject to the treatment or prevention described herein. In particular, the term patient will refer to a mammal. More particularly, the term patient will refer to a human (such an an adult human).

Compounds of the invention may be particularly useful in the treatment or prevention of (particularly, the prevention of) a pathological condition associated with excess fibrin deposition and/or thrombus formation (such as those described herein) in patients at increased risk of developing one or more such condition.

In a particular embodiment of the first to seventh aspects of the invention (including all embodiments thereof), the treatment or prevention (e.g. the prevention, which may also be referred to as prophylaxsis) is in a patient at increased risk of developing a pathological condition associated with excess fibrin deposition and/or thrombus formation (which the skilled person will understand as referring to reducing the risk of the relevant condition, as described herein).

As described herein, several conditions and risk factors are associated with increased susceptibility to thrombotic events (i.e. thrombus formation). These include atherosclerosis, hypertension, abdominal obesity, smoking, sedentary lifestyle, and low-grade inflammation. Thus, in particular embodiments of the first to seventh aspects of the invention (including all embodiments thereof), the treatment or prevention (e.g. the prevention, which may also be referred to as prophylaxsis) is in a patient having one or more such condition/risk factor.

In more particular embodiments, the patient at increased risk of developing a pathological condition associated with excess fibrin deposition and/or thrombus formation is a patient who:
(i) is suffering from one or more medical condition associated with increased risk of thrombus formation, such as metabolic syndrome (e.g. type II diabetes), oncologic diseases, heart failure, renal failure and/or sepsis;
(ii) has previously experienced one or more incidence of a pathological condition associated with excess fibrin deposition and/or thrombus formation, such as one or more incidence of myocardial infarction, ischemic stroke and pulmonary embolism (e.g. one or more incidence of ischemic stroke, such as a major ischemic stroke, minor ischemic stroke or TIA); and/or
(iii) has one or more lifestyle and/or environmental factors placing them at said increased risk, such the patient being a smoker, obese and/or having decreased mobility (e.g. the patient is bed-ridden, such as a patient in a medical unit or elderly care unit).

Thus, in particular embodiments, references to a patient at increased risk of developing a pathological condition associated with excess fibrin deposition and/or thrombus formation will include references to an obese patient, e.g. a patient with a body mass index (BMI) that is above 25 (e.g. above 30 and above 35).

As used herein, references to a patient at increased risk of developing a pathological condition associated with excess fibrin deposition and/or thrombus formation may also include patients (e.g. human male patients) who are 50 years of age or older (e.g. 60 years of age or older).

In particular embodiments, a patient at increased risk of developing a pathological condition associated with excess fibrin deposition and/or thrombus formation may also be a patient who has elevated PAI-1 levels.

For example, as described herein, a patient at increased risk of developing a pathological condition associated with excess fibrin deposition and/or thrombus formation may also be a patient who is suffering from local or systemic inflammation, such as that associated with elevated PAI-1 levels.

Thus, in particular embodiments, a patient at increased risk of developing a pathological condition associated with excess fibrin deposition and/or thrombus formation may be a patient having PAI-1 levels in morning plasma above about 20 ng/ml (e.g. above about 40 ng/ml, such as above about 60 ng/ml, e.g. above about 80 ng/ml or, more particularly, above about 100 ng/ml).

For example, a patient at increased risk of developing a pathological condition associated with excess fibrin deposition and/or thrombus formation may be a patient having PAI-1 levels in morning plasma above about 20 ng/ml (e.g. above about 40 ng/ml, such as above about 60 ng/ml, e.g. above about 80 ng/ml or, more particularly, above about 100 ng/ml) and having experienced one or more incidence of myocardial infarction, ischemic stroke and pulmonary embolism (e.g. one or more incidence of ischemic stroke, such as a major ischemic stroke, minor ischemic stroke or TIA).

In certain embodiments, the patient is not suffering from a:
  (i) a CNS or psychiatric disorder, such as epilepsy, migraine and/or bipolar disorder; and/or
  (ii) Fragile X syndrome and/or familial adenomatous polyposis.

Thus, in a particular embodiment of the first to seventh aspects of the invention (including all embodiments thereof), the treatment or prevention (e.g. the prevention) is in a patient who is:
  (a) at increased risk of developing a pathological condition associated with excess fibrin deposition and/or thrombus formation (particularly as defined herein); and
  (b) is not suffering from a CNS or psychiatric disorder (as defined herein, particularly epilepsy and/or bipolar disorder).

FIGURES

FIG. 1 shows a schematic representation of the circadian rhythm (i.e. variation) of PAI-1 levels in an adult human during a typical 24 hour period. The lower curve represents the variation of PAI-1 levels in a normal (i.e. healthy) patient. The upper curve represents the variation in PAI-1 levels in a patient having increased levels of PAI-1 (e.g. patients with obesity and/or the metabolic syndrome). The y-axis represents arbitrary plasma levels and is abbreviated to illustrate the positively skewed distribution toward high plasma levels in obesity/metabolic syndrome. The x-axis represents clock time.

FIG. 2 shows the results of the in vitro release profile analysis as described in Example 8 herein below.

FIG. 3 provides an example of a release profile as may be provided by pharmaceutical formulations as described in the eighth aspect of the invention, compared to release profiles as may be provided by corresponding immediate release (IR) and extended release (ER) formulations.

EXAMPLES

Figure 1:
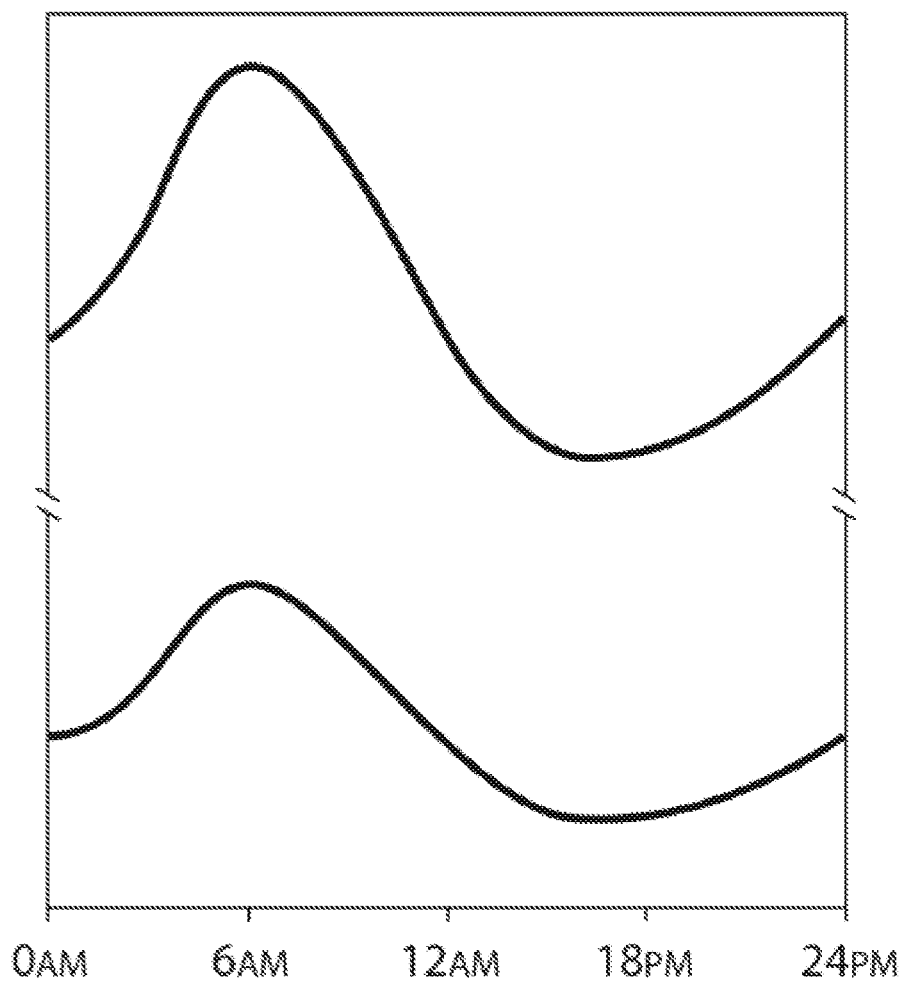

The following examples are included to further illustrate the invention, although the skilled person will understand that the invention is in no way restricted to the specific aspects described therein.

Example 1

VPA and PAI-1

The effects of VPA on PAI-1 were analysed in two different proof-of-concept studies in healthy subjects as well as in patients with manifest atherosclerotic disease. The studies had a randomized cross-over design and PAI-1 levels were investigated before and after treatment with valproic acid. PAI-1 plasma levels were measured in the morning at the first day of the study as well as at the end of the treatment period with VPA (see example 2 for details on the PAI-1 analysis).

In the first study, 10 healthy non-smoking white male subjects (with mean BMI of approximately 26), aged 50-70 years were included and treated with valproic acid 500 mg (Ergenyl Retard, Sanofi) twice daily during 14 days. Unexpectedly we detected a more than 50% reduction (from 22.2 to 10.8 ng/ml, p<0.05) in circulating plasma PAI-1 levels during mid-morning in comparison to the midmorning levels found before treatment with VPA.

In the second study, 16 non-smoking white male patients, aged 50-80 years with a history of a myocardial infarction were included. On top of their ordinary prescription (beta-blocker, ACE-inhibitor, statin, aspirin) they were treated with valproic acid 500 mg (Ergenyl Retard, Sanofi), twice daily during 28 days. In this study we detected a 45% reduction in circulating plasma PAI-1 levels (from 19.6 ng/ml to 11 ng/ml (p=0.01)), during midmorning.

Example 2

Intermediate Endpoint Study: Effects of Valproic Acid on In Vivo PAI-1 in Man

An intermediate endpoint proof-of-concept study is performed in patients with TIA/minor stroke investigated before and after treatment with Valproic acid. Valproic acid is administrated as an enteric-coated tablet with delayed absorption.

The study comprises 20 patients with TIA/minor stroke. Patients are investigated before and after oral treatment with 400 mg valproic acid once time daily at 11 pm for 2 weeks. Plasma PAI-1 levels and plasma concentrations of valproic acid is followed daily during the study period at the following time-points: 3 am, 6 am, 10 am, 16 pm, 22 pm PAI-1 levels are measured by commercially available ELISA-kits (Coaliza PAI-1, Chromogenix AB) and the plasma concentration of valproic acid an metabolites thereof is analyzed according to clinical routine at the Sahlgrenska University laboratory, Gothenburg, Sweden.

The plasma concentration of valproic acid is found to peak between 3 am and 6 am and thereafter declines to very low levels during the trough in PAI-1 concentrations. The peak in plasma valproic acid coincides with the peak level of plasma PAI-1 between 3 am and 6 am. The plasma concentration of valproic acid and plasma PAI-1 levels follow each other with a pronounced circadian elevation with its peak during the early morning hours.

The plasma PAI-1 levels are lowered by approximately 30% after the treatment.

Example 3

Clinical Outcome Study in High-Risk Patients for Prevention of Recurrent Thromboembolic Events Using Valproic Acid A clinical outcome study is performed in high-risk patients who have experienced a recent major atherothrombotic cardiovascular event (myocardial infarction or TIA/ischemic stroke) to investigate the preventive effect of valproic acid treatment on the risk for recurrent events. The annual risk for a recurrent atherothrombotic event in the investigated population is estimated to approximately 7%.

Patients are randomized in a parallel study design to receive double-blind oral treatment with 400 mg valproic acid (as in Example 2) or placebo once time daily at 11 pm, in addition to optimal conventional treatment. The event rate is monitored by Kaplan-Meyer statistics. The primary efficacy endpoint is the composite measure of either mortality, or non-fatal myocardial infarction or ischemic stroke. The study is event-driven to a total of 180 events.

The study is expected to show that long-term valproic acid treatment reduces this risk by approximately 30% in addition to that of conventional therapy, i.e. lowers the annual absolute event rate to approximately 5%. Thus, the study is expected to confirm the clinical efficacy and feasibility of using valproic acid for secondary prevention of cardiovascular disease.

Example 4

Core tablets with a composition according to Table 1 were manufactured at a batch size of 200 g.

TABLE 1

Core tablet formulation.

| Component | Amount, % w/w |
|---|---|
| Sodium valproate | 23.06 |
| MCC | 64.94 |
| Copovidone | 5 |
| Croscarmellose sodium | 5 |
| Silica, colloidal anhydrous | 1 |
| Magnesium stearate | 1 |

Sodium valproate was crushed in a mortar and sieved through a 0.50 mm screen. 46.1 g of the screened material was charged in a 1L-vessel of Turbula T2F together with 129.9 g MCC, 10 g copovidone, 10 g croscarmellose sodium and 2 g silica. After mixing for 4 min at 32 rpm the mixture was sieved through a 0.50 mm screen and mixed for 4 min further. Magnesium stearate 2 g was roughly pre-mixed with a similar volume of the powder mixture in a steel vessel with a spoon and sieved through a 0.50 mm screen, added to the 1L-vessel and mixed with the powder mixture for 2 min at 22 rpm.Tablets were compressed in 5 mm circular punch/die sets with normal cup depth in a rotary press (Fette 52i) at a main compression force of 2 kN. Tablet weight was approx. 65 mg and resistance to crushing approx. 5 kp.

Example 5

Core tablets with a composition according to Table 2 were manufactured at a batch size of 300 g.

TABLE 2

Core tablet formulation.

| Component | Amount, % w/w |
|---|---|
| Sodium valproate | 23.06 |
| MCC | 47.94 |
| Fumaric acid | 16 |
| Copovidone | 5 |
| Croscarmellose sodium | 5 |
| Silica, colloidal anhydrous | 1 |
| Magnesium stearate | 2 |

Sodium valproate was crushed in a mortar and sieved through a 0.50 mm screen. 69.2 g of the screened material was charged in a 2L-vessel of Turbula T2F together with 133.8 g MCC. Fumaric acid 48 g, sieved through a 0.50 mm screen, was added to the mixer vessel, too, together with 15 g copovidone and 15 g croscarmellose sodium. Silica 3 g and MCC 10 g were roughly mixed in a steel vessel with a spoon and sieved through a 0.50 mm screen and added to the 2L-vessel. The powders were mixed for 8 min at 32 rpm. Magnesium stearate 6 g was roughly pre-mixed with a similar volume of the powder mixture in a steel vessel with a spoon and sieved through a 0.50 mm screen, added to the 2L-vessel and mixed with the powder mixture for 2 min at 22 rpm. Tablets were compressed in 5 mm circular punch/die sets with normal cup depth in a rotary press (Fette 52i) at a main compression force of 2 kN. Tablet weight was approx. 75 mg and resistance to crushing approx. 5 kp.

Example 6

Core tablets according to Example 4 were coated with Eudragit® FS3OD (aqueous dispersion 30%)/PlasACRYL™ T20 according to Table 3 using a Hüttlin Kugelcoater HKC005. The batch size was 50 g. The coating was performed with an air inlet temperature of 47° C., resulting in a product temperature of 28-29° C. The air flow was adjusted to achieve an appropriate fluidization of the tablets during the coating. The coating layer was applied to the core tablets so as to obtain a weight gain of 20%. After the coating, the tablets were cured at 40° C. for 2 hours.

TABLE 3

Coating spray suspension for Example 6

| Ingredient | Quantity, % w/w |
|---|---|
| Eudragit ® FS30D | 60.61 |
| PlasACRYL ™ T20 | 9.09 |
| Water | 30.3 |

Example 7

Core tablets according to Example 5 were coated with Eudragit® FS3OD (aqueous dispersion 30%)/PlasACRYL™ T20 according to Table 3 using a Hüttlin Kugelcoater HKC005. The batch size was 50 g. The coating was performed with an air inlet temperature of 47° C., resulting in a product temperature of 28-29° C. The air flow was adjusted to achieve an appropriate fluidization of the tablets during the coating. The coating layer was applied to the core tablets so as to obtain a weight gain of 9%. After the coating, the tablets were cured at 40° C. for 2 hours.

TABLE 3

Coating spray suspension for Example 7

| Ingredient | Quantity, % w/w |
|---|---|
| Eudragit ® FS30D | 60.61 |
| PlasACRYL ™ T20 | 9.09 |
| Water | 30.3 |

Example 8

In Vitro Release

The in vitro release profile of the composition as prepared in Example 7 was analysed using USP dissolution Apparatus 2 (paddle) Ph. Eur. 2.9.3 (as described herein). The following conditions were used: temperature 37.0±0.5° C.; paddle speed 75 rpm. The samples were analyzed for valproic acid by HPLC using a Phenomenex Luna C18 column, 150×4.6 mm, particle size 5 µm, column temperature 40° C., mobile phase acetonitrile/phosphate buffer (pH 3.0) 1:1, flow rate 1 mL/min.

The level of release at particular time points and pH of solution was analysed. pH adjustments and sample pulls are described below. pH adjustments were performed immediately after sample pulls. Time points refer to total running time.

Stomach, pH 1

One tablet was added to a vessel containing 250 mL 0.1 M hydrochloric acid solution and the content was stirred for 1 hour and samples were pulled.

Small Intestine, pH 6.4

181 mL of a solution of potassium phosphate buffer and potassium hydroxide was added to the vessel to give pH 6.4. Samples were pulled after 1.5 and 2.5 hours.

Ilium, pH 6.8

69 mL of a solution of potassium phosphate buffer and potassium hydroxide was added to the vessel to give pH 6.8. Samples were pulled after 3 and 4 hours.

Terminal Ilium, pH 7.3

253 mL of an aqueous potassium hydroxide solution was added to the vessel to give pH 7.3. Samples were pulled after 4.25, 4.5, 4.75, 5, 5.5 and 6 hours.

Figure 2:
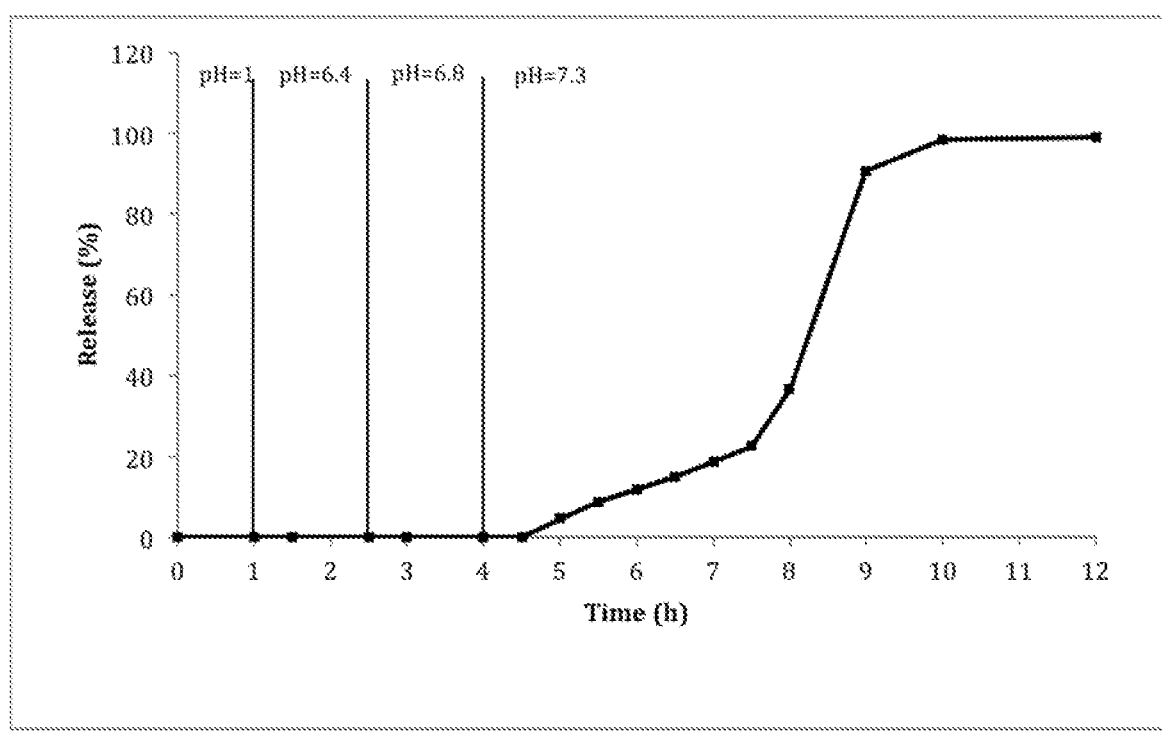
Figure 3:
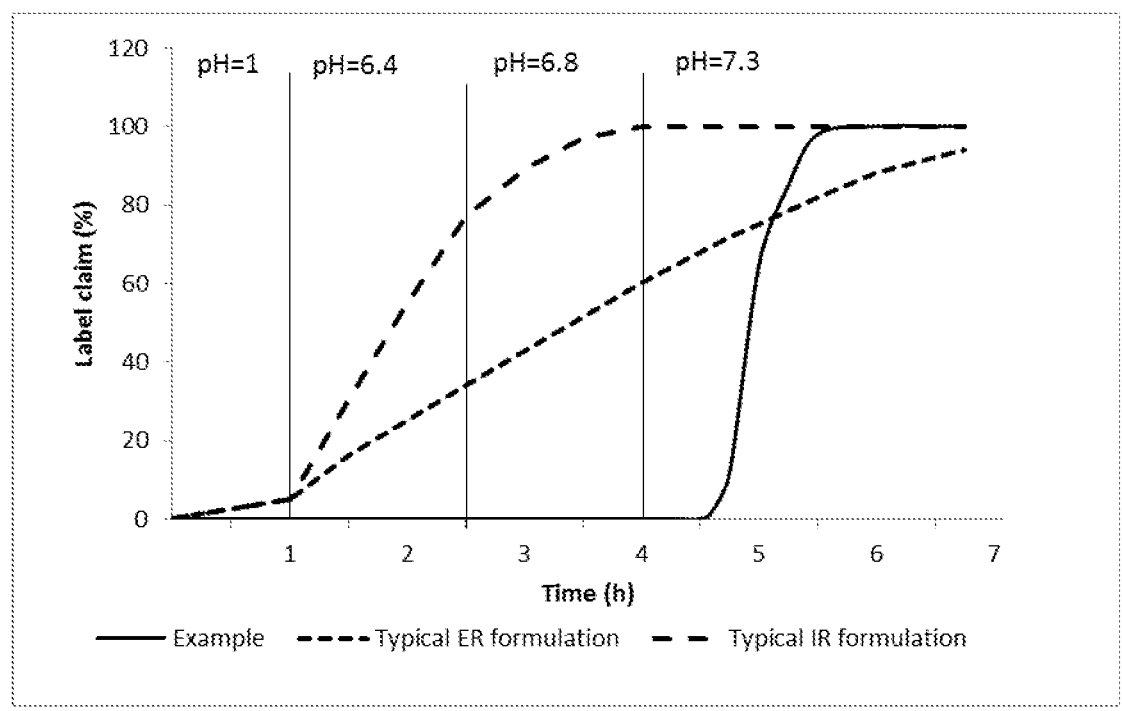

The release profile observed for the composition of Example 7 is shown in FIG. 2 as provided herein.

Example 9

Manufacturing of Tablet Cores

The batch formulas of the granulations and core tablet formulations employed in subsequent coating experiments are displayed in Tables 4 and 5. In Table 5 the actual mean tablet weight (16.1 mg (90% API), 16.5 mg (95% API and 16.3 mg (99% API) was used when calculating the amounts of the components per tablet.

TABLE 4

Batch formulas of granulations

| Component | 90% API, 10% acid, | 95% API, 5% acid | 99% API, 1% acid |
|---|---|---|---|
| Sodium valproate, g | 1350 | 1425 | 1485 |
| Fumaric acid, g | 150 | 75 | 15 |
| Silica, colloidal anhydrous, g | 150 | 150 | 150 |
| Hydroxypropyl cellulose*, g | 28.5 | 28.5 | 28.5 |
| Ethanol, anhydrous**  | 660 | 660 | 660 |
| Silica, colloidal anhydrous***, g | 8.4 | 8.4 | 8.4 |
| Magnesium stearate, g | 16.8 | 16.8 | 16.8 |

*Klucel LF
**Evaporated during the process
***Added at the final mixing

TABLE 5

Core tablet formulations.

| Component | 90% API | 95% API | 99% API |
|---|---|---|---|
| Sodium valproate, mg/tabl (and %) | 12.75 (79.24) | 13.80 (83.64) | 14.21 (87.16) |
| Fumaric acid, mg/tabl (and %) | 1.42 (8.80) | 0.73 (4.40) | 0.14 (0.088) |
| Silica, colloidal anhydrous, mg/tabl (and %) | 1.50 (9.30) | 1.53 (9.30) | 1.52 (9.30) |
| Hydroxypropyl cellulose*, mg/tabl (and %) | 0.27 (1.67) | 0.28 (1.67) | 0.27 (1.67) |
| Magnesium stearate, mg/tabl (and %) | 0.16 (0.99) | 0.16 (0.99) | 0.16 (0.99) |

Granulation was performed with two sub batches of each formulation. These two sub batches were mixed with glidant and lubricant and compressed in a rotary press. Sodium valproate (API) and fumaric acid were sieved through a 1.00 mm screen. A pre-mixture was made of fumaric acid and a part of API in a mortar with pestle for the formulations with 95 and 99% API.

Aerosil (silica colloidal) was roughly mixed with the pre-mixture and remaining API (95 and 99% API) and sieved through a 1.00 mm sieve. For 90% API, Aerosil and API were roughly mixed and sieved through a 1.00 mm screen, i.e. no pre-mixture.

The roughly mixed powders were then mixed in a tumbling mixer—6 L vessel, 8 min, at 32 rpm. This mixture was granulated with an ethanolic solution of hydroxypropyl cellulose in a planetary mixer. The granulation was spread on Al-foil in a tray and left on the bench to evaporate the solvent during the night. On the following day the granulation was dried for 4-6 h at 60° C. The dried granulation was then milled in a Quadro Comil. Silica was mixed with dried, milled granulation—i.e. two sub batches—for 8 min at 32 rpm in a 17 L vessel. Magnesium stearate and a similar volume of the silica-granulation-mixture were roughly mixed and sieved through a 1.00 mm screen and added to the vessel with the remaining silica-granulation-mixture. Mixing for 2 min at 23 rpm was performed. Tablets were compressed in 3 mm 5-tip punch/die sets—10 sets, i.e. complete filling of the turret—at a compression pressure of approx. 200 MPa. Tablet weight was approx. 16 mg.

Example 10

Coatings

Kollicoat® IR Coating

Core tablets according to Example 9 were coated with Kollicoat® IR/talc aqueous dispersion (protective coating) according to the table below using a Hüttlin Kugelcoater HKC005. The batch size was 150 g. The coating was performed with an air inlet temperature of 49° C., resulting in a product temperature of 41-43° C. The airflow was adjusted to achieve an appropriate fluidization of the tablets during the coating. The coating layer was applied to the core tablets so as to obtain a weight gain of 7.9 or 8.5% (4 or 5 mg/cm$^2$, the former for L 30 D-55 and the latter for FS 30 D). After the coating, the tablets were cured and dried to constant weight in the coating equipment at 60° C. These coated cores were used for all coating processes below.

| Ingredient | Quantity, % w/w |
| --- | --- |
| Kollicoat ® IR | 12.00 |
| Talc | 4.29 |
| Water | 83.71 |

FS 30 D Coating

Core tablets according to Example 9 were coated with Eudragit® FS30D (aqueous dispersion 30%)/PlasACRYL™ T20 according to the table below using a Hüttlin Kugelcoater HKC005. The batch size was 80 g. The coating was performed with an air inlet temperature of 48° C., resulting in a product temperature of 37-39° C. The airflow was adjusted to achieve an appropriate fluidization of the tablets during the coating. The coating layer was applied to the core tablets so as to obtain a weight gain of 15, 20 or 29% (9, 12 or 17 mg/cm$^2$). After the coating, the tablets were cured and dried to constant weight in the coating equipment at 48° C.

| Ingredient | Quantity, % w/w |
| --- | --- |
| Eudragit ® FS30D | 60.61 |
| PlasACRYL ™ T20 | 9.09 |
| Water | 30.3 |

Eudragit L 30 D-55 Coating

Core tablets according to Example 9 were coated with Eudragit® L 30 D-55 (aqueous dispersion 30%)/PlasACRYL™ HTP20 according to the table below using a Hüttlin Kugelcoater HKC005. The batch size was 150 g. The coating was performed with an air inlet temperature of 52° C., resulting in a product temperature of 42-43° C. The airflow was adjusted to achieve an appropriate fluidization of the tablets during the coating. The coating layer was applied to the core tablets so as to obtain a weight gain of 15% (9 mg/cm$^2$). After the coating, the tablets were cured and dried to constant weight in the coating equipment at 52° C.

| Ingredient | Quantity, % w/w |
| --- | --- |
| Eudragit ® L 30 D-55 (30% aq. disp) | 57.00 |
| PlasACRYL ™ HTP20 | 14.60 |
| Water | 28.40 |

Kollicoat SR 30 D/Kollicoat IR Coating

Core tablets according to Example 9 (with Eudragit L 30 D-55 as described above) were coated with Kollicoat® SR 30 D (aqueous dispersion 30%)/Kollicoat® IR/triethyl citrate/talc according to the table below using a Hüttlin Kugelcoater HKC005 (resulting in a Kollicoat® SR 30 D/Kollicoat® IR ratio of 9:1 based on dry weight). The batch size was 80 g. The coating was performed with an air inlet temperature of 49-50° C., resulting in a product temperature of 40-42° C. The airflow was adjusted to achieve an appropriate fluidization of the tablets during the coating. The coating layer was applied to the core tablets so as to obtain a weight gain of 6, 9 or 13% (4, 6 or 9 mg/cm$^2$). After the coating, the tablets were cured and dried to constant weight in the coating equipment at 50° C.

| Ingredient | Quantity, % w/w |
| --- | --- |
| Kollicoat ® SR 30 D (30% aq. disp) | 48.00 |
| Kollcoat ® IR | 1.60 |
| Triethyl citrate | 0.80 |
| Talc | 4.80 |
| Water | 44.80 |

Example 11

In Vitro Release Dissolution Model

The in vitro release profile of a composition as prepared the examples was analysed using USP dissolution Apparatus 2 (paddle) Ph. Eur. 2.9.3 (as described herein). The following conditions were used: temperature 37.0±0.5° C.; paddle speed 75 rpm. The samples were analyzed for valproic acid by HPLC using a Phenomenex Luna C18 column, 150×4.6 mm, particle size 5 pm, column temperature 40° C., mobile phase acetonitrile/phosphate buffer (pH 3.0) 1:1, flow rate 1 mL/min.

The level of release was measured after 2 hours in acidic media (750 mL 0.1 M hydrochloric acid solution, pH 1); pH is then raised to 7.0 by adding 250 mL 0.2 M trisodium phosphate buffer. The level of release was generally measured at time points 30, 60, 120, 180, 240, 360 and 480 minutes in the buffer stage.

Example 12

Effect of Coating on Dissolution

Figure 5:
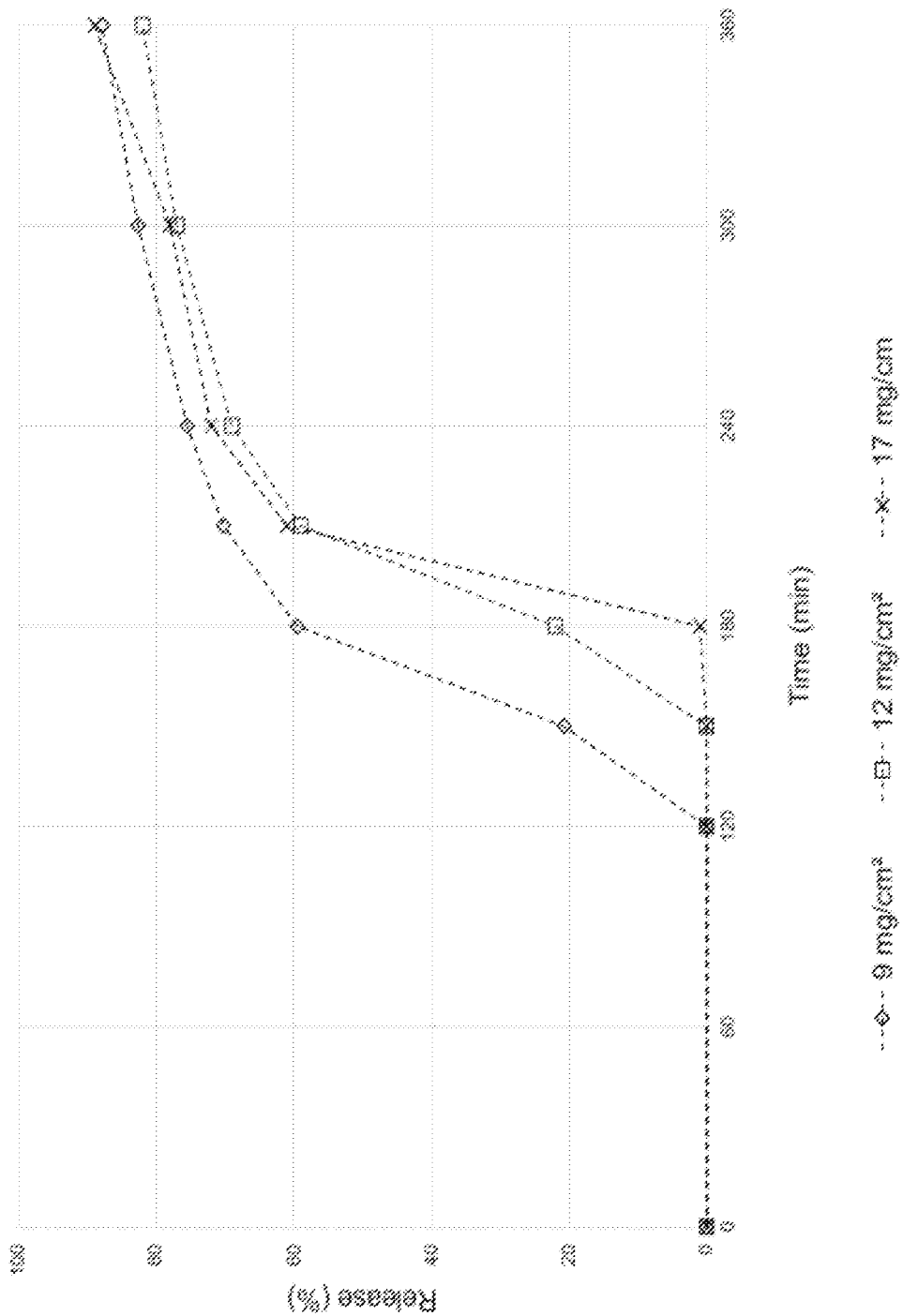
FIG. 5 shows the results of the in vitro release profile analysis of tablets (mini tablets) coated with Eudragit FS 30 D as described in Example 12 herein below.
Figure 6:
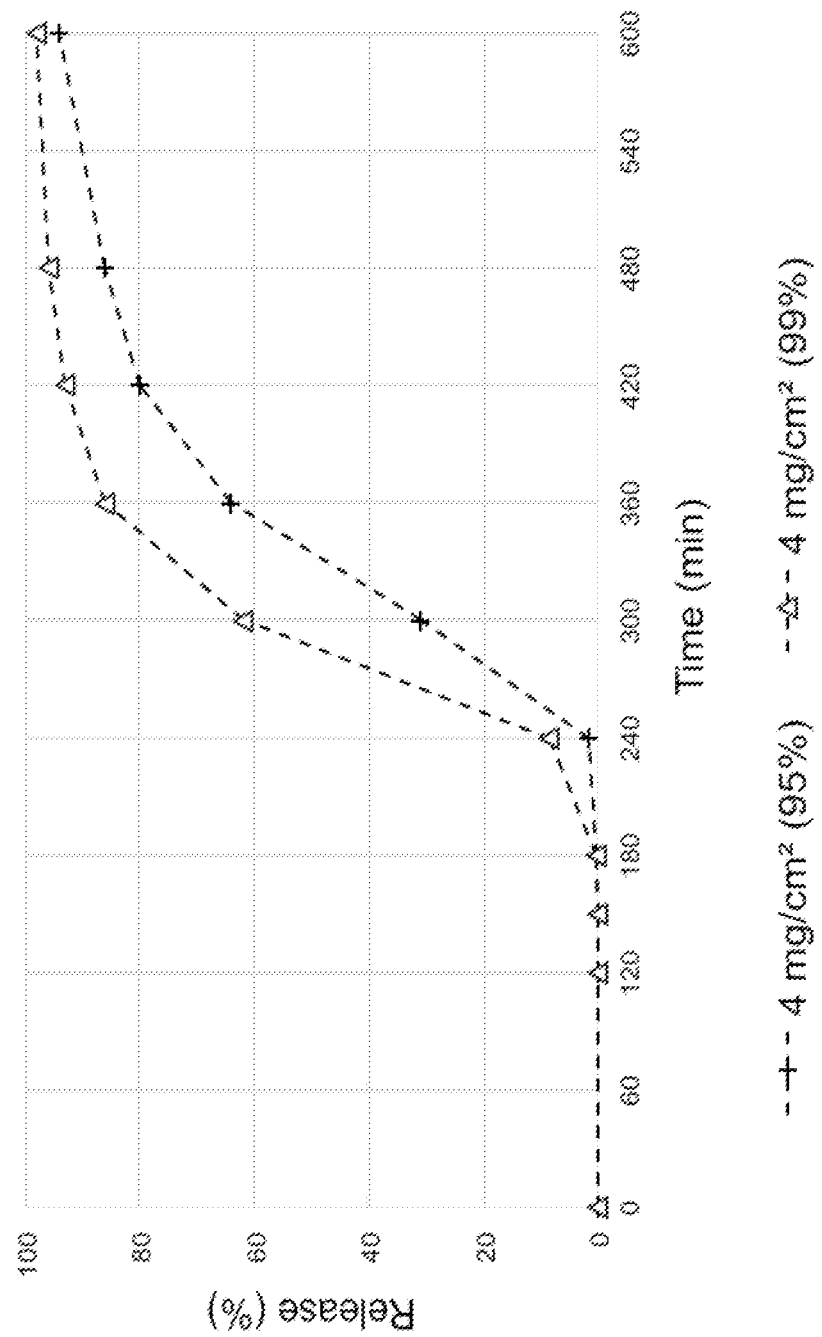
FIG. 6 shows the results of the in vitro release profile analysis of tablets (mini tablets) coated with Eudragit L 30 D-55 and Kollicoat SR 30 D/Kollicoat IR using different tablet cores and the same coating amount for the top coating as described in Example 12 herein below.
Figure 7:
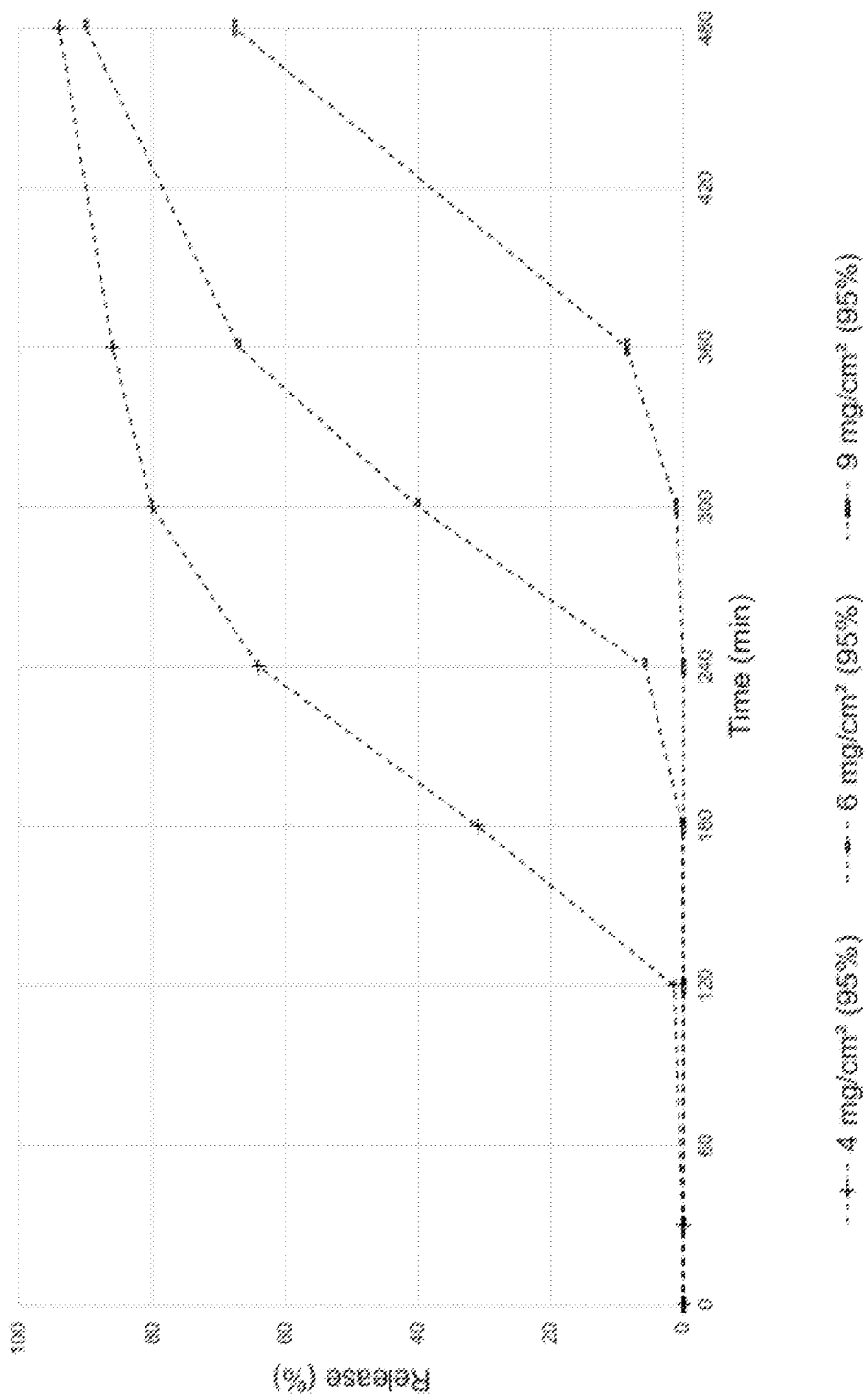
FIG. 7 shows the results of the in vitro release profile analysis of tablets (mini tablets) coated with Eudragit L 30 D-55 and Kollicoat SR 30 D/Kollicoat IR using the same tablet cores and varying coating amounts of the top coating as described in Example 12 herein below.

The coated tablets from Example 10 were analysed using the method described in Example 11. The results for the tablets coated with Eudragit FS 30 D are found in FIG. 5 and the results for the tablets coated with Eudragit L 30 D-55 and Kollicoat SR 30 D/Kollicoat IR are found in FIG. 6 (different cores, same coating amount) and FIG. 7 (same tablet cores, varying coating amounts).

Example 13

Effect of Core on Dissolution

Tablet cores with different combinations of sodium valproate and fumaric acid were produced according to the method described in Example 9, as described in the table below.

|  | Core type (%) | | | | |
| --- | --- | --- | --- | --- | --- |
|  | 50 | 75 | 95 | 99 | 100 |
| Sodium valproate | 46.08% | 66.03% | 83.64% | 87.16% | 88.04% |
| Fumaric acid | 46.08% | 22.01% | 4.40% | 0.88% | 0.00% |
| Aerosil 200 | 5.10% | 9.30% | 9.30% | 9.30% | 9.30% |
| Klucel LF | 1.75% | 1.67% | 1.67% | 1.67% | 1.67% |
| Magnesium stearate | 0.99% | 0.99% | 0.99% | 0.99% | 0.99% |
| Total | 100.00% | 100.00% | 100.00% | 100.00% | 100.00% |

Figure 4:
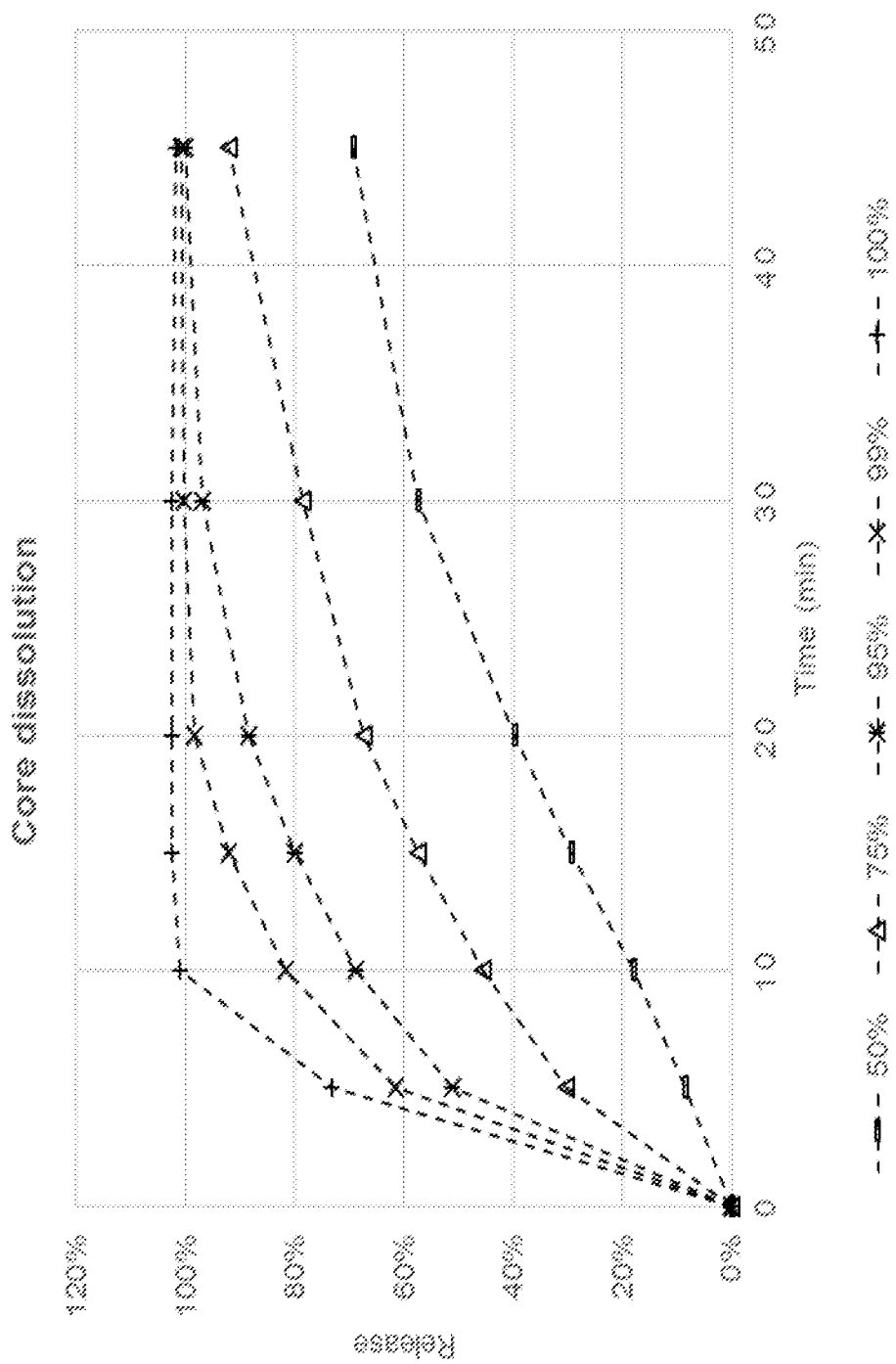
FIG. 4 shows the results of the in vitro release profile analysis as described in Example 13 herein below.

Tablet dissolution was measured in accordance with the procedure described in Example 9. Samples were pulled at 5, 10, 15, 20, 30 and 40 minutes and analysed according to the method described in Example 11 without the acidic pH stage (pH about 7.0 throughout the experiment). Results are shown in FIG. 4.

The invention claimed is:

1. A delayed release pharmaceutical formulation having two or more components comprising:
   (a) valproic acid (VPA) and/or a pharmaceutically acceptable salt thereof; and
   (b) one or more secondary acids selected from fumaric acid and/or succinic acid, and optionally comprising one or more pharmaceutically acceptable excipients,
   wherein the amount of secondary acid is from about 0.1% to about 5% of the weight of the VPA and/or a pharmaceutically acceptable salt thereof,
   wherein the pharmaceutical formulation comprises an enteric coating, and
   wherein upon oral administration to a subject:
   release of the VPA and/or pharmaceutically acceptable salt thereof from the pharmaceutical formulation is delayed for about four hours, and
   at least 60% of the VPA and/or pharmaceutically acceptable salt thereof is released during a period from about four to about eight hours after administration.

2. The pharmaceutical formulation of claim 1, wherein the one or more secondary acids in component (b) are in non-salt form.

3. The pharmaceutical formulation of claim 1, wherein the one or more secondary acids is fumaric acid.

4. The pharmaceutical formulation of claim 1, wherein the amount of secondary acid is from about 0.1% to about 3% of the weight of the VPA and/or a pharmaceutically acceptable salt thereof.

5. The pharmaceutical formulation of claim 1, wherein the formulation comprises one or more components having a solid core comprising component (a), wherein component (a) is present in an amount that is at least 50% by weight thereof, and optionally wherein said solid core further comprises component (b).

6. The pharmaceutical formulation of claim 5, wherein the solid core comprising components (a) and (b) is first coated with a sustained release coating and then an enteric coating.

7. The pharmaceutical formulation of claim 1, wherein the composition is in the form of a tablet or capsule for oral administration and is formulated such that at least 70% of the VPA and/or pharmaceutically acceptable salt thereof is released during a period from about four to about eight hours after administration.

8. The pharmaceutical formulation of claim 1, wherein at least 60% of the VPA and/or pharmaceutically acceptable salt thereof is released during a period from about six to about eight hours after administration.

9. The pharmaceutical formulation of claim 5, wherein the solid core comprising components (a) and (b) is first coated with an enteric coating and then a sustained release coating.

10. A delayed release pharmaceutical formulation having two or more components comprising:
    (a) valproic acid (VPA) and/or a pharmaceutically acceptable salt thereof; and
    (b) one or more secondary acids selected from fumaric acid and/or succinic acid, and optionally comprising one or more pharmaceutically acceptable excipients,
    wherein the amount of secondary acid is from about 0.1% to about 5% of the weight of the VPA and/or a pharmaceutically acceptable salt thereof,
    wherein the pharmaceutical formulation comprises an enteric coating, and
    wherein upon oral administration to a subject:
    release of the VPA and/or pharmaceutically acceptable salt thereof from the pharmaceutical formulation is delayed for about four hours to about six hours, and
    at least 60% of the VPA and/or pharmaceutically acceptable salt thereof is released during a period from about eight to about ten hours after administration.

11. The pharmaceutical formulation of claim 10, wherein the one or more secondary acids in component (b) are in non-salt form.

12. The pharmaceutical formulation of claim 10, wherein the one or more secondary acids is fumaric acid.

13. The pharmaceutical formulation of claim 10, wherein the amount of secondary acid is from about 0.1% to about 3% of the weight of the VPA and/or a pharmaceutically acceptable salt thereof.

14. The pharmaceutical formulation of claim 10, wherein the formulation comprises one or more components having a solid core comprising component (a), wherein component (a) is present in an amount that is at least 50% by weight thereof, and optionally wherein said solid core further comprises component (b).

15. The pharmaceutical formulation of claim 14, wherein the solid core comprising components (a) and (b) is first coated with a sustained release coating and then an enteric coating.

16. The pharmaceutical formulation of claim 14, wherein the solid core comprising components (a) and (b) is first coated with an enteric coating and then a sustained release coating.

17. The pharmaceutical formulation of claim 10, wherein at least 60% of the VPA and/or pharmaceutically acceptable salt thereof is released during a period from about six to about eight hours after administration.

18. A delayed release pharmaceutical for formulation having two or more components comprising:
    (a) valproic acid (VPA) and/or a pharmaceutically acceptable salt thereof; and
    (b) one or more secondary acids selected from fumaric acid and/or succinic acid, and optionally comprising one or more pharmaceutically acceptable excipients,
    wherein the amount of secondary acid is from about 0.1% to about 5% of the weight of the VPA and/or a pharmaceutically acceptable salt thereof,
    wherein the pharmaceutical formulation comprises an enteric coating, and
    wherein upon oral administration to a subject:
    release of the VPA and/or pharmaceutically acceptable salt thereof from the pharmaceutical formulation is delayed for about four hours to about six hours, and at least 60% of the VPA and/or pharmaceutically acceptable salt thereof is released during a period from about six to about eight hours after administration.

* * * * *

UNITED STATES PATENT AND TRADEMARK OFFICE
CERTIFICATE OF CORRECTION

PATENT NO. : 11,395,808 B2
APPLICATION NO. : 16/090664
DATED : July 26, 2022
INVENTOR(S) : Gustafsson et al.

It is certified that error appears in the above-identified patent and that said Letters Patent is hereby corrected as shown below:

On the Title Page

(30) Foreign Application Priority Data: delete "1606197" and insert --1606197.0--

In the Specification

Column 64, Line 37: delete "5 pm" and insert --5 µm--

In the Claims

Column 66, Line 52, Claim 18: delete "pharmaceutical for formulation" and insert --pharmaceutical formulation--

Signed and Sealed this
Fifteenth Day of November, 2022

Katherine Kelly Vidal
*Director of the United States Patent and Trademark Office*